US007897845B2

(12) United States Patent
Pozniak et al.

(10) Patent No.: US 7,897,845 B2
(45) Date of Patent: Mar. 1, 2011

(54) WHEAT PLANTS HAVING INCREASED RESISTANCE TO IMIDAZOLINONE HERBICIDES

(75) Inventors: Curtis J. Pozniak, Saskatoon (CA); Pierre Hucl, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 831 days.

(21) Appl. No.: 10/486,605

(22) PCT Filed: Jul. 10, 2002

(86) PCT No.: PCT/CA02/01051
§ 371 (c)(1),
(2), (4) Date: Feb. 9, 2004

(87) PCT Pub. No.: WO03/014357
PCT Pub. Date: Feb. 20, 2003

(65) Prior Publication Data
US 2004/0237134 A1 Nov. 25, 2004

Related U.S. Application Data

(60) Provisional application No. 60/311,282, filed on Aug. 9, 2001.

(51) Int. Cl.
*A01H 5/00* (2006.01)
*A01H 5/10* (2006.01)
(52) U.S. Cl. .................. 800/300; 800/298; 800/320.1
(58) Field of Classification Search .................. None
See application file for complete search history.

(56) References Cited

U.S. PATENT DOCUMENTS

| 4,761,373 | A | 8/1988 | Anderson et al. |
| 5,013,659 | A | 5/1991 | Bedbrook et al. |
| 5,304,732 | A | 4/1994 | Anderson et al. |
| 5,331,107 | A | 7/1994 | Anderson et al. |
| 5,731,180 | A | 3/1998 | Dietrich |
| 5,767,361 | A | 6/1998 | Dietrich |
| 5,853,973 | A | 12/1998 | Kakefuda et al. |
| 5,928,937 | A | 7/1999 | Kakefuda et al. |
| 6,211,438 | B1 | 4/2001 | Anderson et al. |
| 6,211,439 | B1 | 4/2001 | Anderson et al. |
| 6,222,100 | B1 | 4/2001 | Anderson et al. |
| 6,225,105 | B1 | 5/2001 | Sathasivan et al. |
| 6,339,184 | B1 * | 1/2002 | Smith ............... 800/276 |
| 6,613,963 | B1 * | 9/2003 | Gingera et al. ........ 800/306 |
| 6,696,294 | B1 * | 2/2004 | Konzak ............... 435/441 |

FOREIGN PATENT DOCUMENTS

| EP | 0 360 750 A2 | 3/1990 |
| EP | 0 375 875 | 7/1990 |
| EP | 0 508 161 A1 | 10/1992 |
| EP | 0 525 384 A2 | 2/1993 |
| WO | WO 90/14000 A1 | 11/1990 |
| WO | WO 00/53763 | 9/2000 |
| WO | WO 02/092820 A1 | 11/2002 |
| WO | WO 03/013225 A2 | 2/2003 |
| WO | WO 03/014356 A1 | 2/2003 |

OTHER PUBLICATIONS

White et al 2002, Weed Science 50: 432-437.*
Bernasconi et al 1995, Journal of Biological Chemistry 270(29): 17381-17385.*
Newhouse et al 1992, Plant Physiology 100: 882-886.*
Lee et al 1999, FEBS Letters 452: 341-345.*
Duggleby, R., et al., "Systematic Characterization of Mutations in Yeast Acetohydroxyacid Synthase," *Eur. J. Biochem.*, 2003, pp. 2895-2904, vol. 270.
Lee, Y., et al., "Effect of Mutagenesis at Serine 653 of *Arabidopsis thaliana* Acetohydroxyacid Synthase on the Sensitivity to Imidazolinone and Sulfonylurea Herbicides," *FEBS Letters*, 1999, pp. 341-345, vol. 452, Federation of European Biochemical Societies.
Barrett, M., "Protection of Grass Crops from Sulfonylurea and Imidazolinone Toxicity," *Crop Safeners for Herbicides*, 1989, pp. 195-220, Academic Press, Inc.
Brown, M., et al., "Hydrolytic Activation versus Oxidative Degradation of Assert Herbicide, an Imidazolinone Aryl-carboxylate, in Susceptible Wild Oat versus Tolerant Corn and Wheat," *Pesticide Biochemistry and Physiology*, 1987, pp. 24-29, vol. 27, Academic Press, Inc.
Chang, A., and R. Duggelby, "Herbicide-resistant Forms of *Arabidopsis thaliana* Acetohydroxyacid Synthase: Characterization of the Catalytic Properties and Sensitivity to Inhibitors of Four Defined Mutants," *Biochemistry J.*, 1998, pp. 765-777, vol. 333.
Chong C., and J. Choi, "Amino Acid Residues Conferring Herbicide Tolerance in Tobacco Acetolactate Synthase," *Biochemical and Biophysical Research Communications*, 2000, pp. 462-467, vol. 279, Academic Press.
Hattori, J., et al., "Multiple Resistance to Sulfonylureas and Imidazolinones Conferred by an Acetohydroxyacid Synthase Gene with Separate Mutations for Selective Resistance," *Molecular Genetics*, 1992, pp. 167-173, vol. 232.
Mourad, G., et al., "Isolation and Genetic Analysis of a Triazolopyrimidine-Resistant Mutant of *Arabidopsis*," *J. Heredity*, 1993, pp. 91-96, vol. 84. Newhouse, K., et al., "Mutations in corn (*Zea mays* L.) Conferring Resistance to Imidazolinone Herbicides," *Theor. Appl. Genet.*, 1991, pp. 65-70, vol. 83, Springer-Verlag.
Newhouse, K., et al., "Tolerance to Imidazolinone Herbicides in Wheat," *Plant Physiology*, 1992, pp. 882-886, vol. 100.
Odell, et al., "Comparison of Increased Expression of Wild-Type and Herbicide-Resistant Acetolactate Synthase Genes in Transgenic Plants, and Indication of Posttranscriptional Limitation on Enzyme Activity," *Plant Physiol.*, (1990), pp. 1647-1654, vol. 94.
Ott, K., et al., "Rational Molecular Design and Genetic Engineering of Herbicide Resistant Crops by Structure Modeling and Site-directed Mutagenesis of Acetohydroxyacid Synthase," *J. Mol. Biol.*, 1996, pp. 359-368, vol. 263, Academic Press Limited.
Repellin, A., et al., "Genetic Enrichment of Cereal Crops via Alien Gene Transfer: New Challenges," *Plant Cell, Tissue and Organ Culture*, 2001, pp. 159-183, vol. 64.

(Continued)

*Primary Examiner* — David H Kruse
(74) *Attorney, Agent, or Firm* — Womble Carlyle Sandridge & Rice PLLC

(57) ABSTRACT

The present invention is directed to wheat plants having increased resistance to an imidazolinone herbicide. More particularly, the present invention includes wheat plants containing one or more IMI nucleic acids such as a Teal IMI cultivar. The nucleic acids are preferably located on or derived from different genomes. The present invention also includes seeds produced by these wheat plants and methods of controlling weeds in the vicinity of these wheat plants.

22 Claims, 42 Drawing Sheets

OTHER PUBLICATIONS

Sathasivan, K., et al., "Nucleotide Sequence of a Mutant Acetolactate synthase Gene from an Imidaziolinone-resistant *Arabidopsis thaliana* var. Columbia," *Nucleic Acids Research*, 1990, pp. 2188, vol. 18(8), Oxford University Press.

Sathasivan, K., et al., "Molecular Basis of Imidazolinone Herbicide Resistance in *Arabidopsis thaliana* var Columbia," *Plant Physiol.*, 1991, pp. 1044-1050, vol. 97.

Sebastian, S., et al., "Semidominant Soybean Mutation for Resistance to Sulfonylurea Herbicides," *Crop. Sci.*, 1989, pp. 1403-1408, vol. 29.

Shaner, D., et al., "Imidazolinone-Resistant Crops: Selection, Characterization, and Management," *Herbicide-Resistant Crops: Agricultural, Environmental, Economic*, 1996, pp. 143-157.

Shaner, D. and P.A. Robson, "Absorption, Translocation, and Metabolism of AC 252 214 in Soybean (*Glycine max*), Common Cocklebur (*Xanthium strumarium*), and Velvetleaf (*Abutilon theophrasti*)," *Weed Sci.*, 1985, pp. 469-471, vol. 33.

Shaner, D., et al., "Imidazolinones: Potent Inhibitors of Acetohydroxyacid Synthase," *Plant Physiol.*, 1984, pp. 545-546, vol. 76.

Singh, B.K., "Biosynthesis of Valine, Leucine and Isoleucine," *Plant Amino Acids*, 1999, pp. 227-247, Marcel Dekker Inc., New York, NY.

Swanson, E., et al., "Microspore Mutagenesis and Selection: Canola Plants with Field Tolerance to the Imidazolinones," *Theor. Appl. Genet.*, 1989, pp. 525-530, vol. 78, Springer-Verlag.

Wright, T.R. and D. Penner, "Cell Selection and Inheritance of Imidazolinone Resistance in Sugarbeet (*Beta vulgaris*)," *Theor. Appl. Genet.*, 1998, pp. 612-620, vol. 96, Springer-Verlag.

GenBank Accession No. BE417248, created Jul. 4, 2000.

GenBank Accession No. BF200418, created Nov. 6, 2000.

EMBL Accession No. AF059600, created Apr. 27, 1998.

J. Andrew Kendig and M.S. DeFelice, "ALS Resistance Cocklebur (*Xanthium strumarium* L.) in Missouri", *WSSA Abstracts*, vol. 34, Feb. 7-10, 1994, 1994 Meeting of the Weed Science Society of America.

Paul R. Schmitzer et al., "Lack of Cross-Resistance of Imazaquin-Resistant *Xanthium strumarium* Acetolactate Synthase to Flumetsulam and Chlorimuron", *Plant Physiol.*, vol. 103, 1993, pp. 281-283.

* cited by examiner

Figure 1

| Cross | | Resistant (R) | Intermediate (I) | Susceptible (S) | Total F₁ screened | | |
|---|---|---|---|---|---|---|---|
| | | | | | R | I | S |
| Teal | | 0 | 0 | 334 | | | |
| 1A | | 59 | 0 | 0 | | | |
| | Teal x 1A | 0 | 5 | 0 | 0 | 10 | 0 |
| | 1A x Teal | 0 | 5 | 0 | | | |
| 9A | | 66 | 0 | 0 | | | |
| | Teal x 9A | 0 | 5 | 0 | 0 | 10 | 0 |
| | 9A x Teal | 0 | 5 | 0 | | | |
| 10A | | 66 | 0 | 0 | | | |
| | Teal x 10A | 0 | 5 | 0 | 0 | 11 | 0 |
| | 10A x Teal | 0 | 6 | 0 | | | |
| 11A | | 53 | 0 | 0 | | | |
| | Teal x 11A | 0 | 7 | 0 | 0 | 15 | 0 |
| | 11A x Teal | 0 | 8 | 0 | | | |
| 15A | | 48 | 0 | 0 | | | |
| | Teal x 15A | 7 | 0 | 0 | 14 | 0 | 0 |
| | 15A x Teal | 7 | 0 | 0 | | | |
| 16A | | 66 | 0 | 0 | | | |
| | Teal x 16A | 0 | 7 | 0 | 0 | 14 | 0 |
| | 16A x Teal | 0 | 7 | 0 | | | |

Figure 2

| Cross | F₂ Generation | | | | | BCF₁ Generation[c] | | | |
|---|---|---|---|---|---|---|---|---|---|
| | Resistant (R) | Susceptible (S) | Ratio tested (R:S) | P Value[a] | Homogeneity of reciprocal crosses[b] | R | S | Ratio tested (R:S)[d] | P Value[e] |
| Teal x 1A | 635 | 201 | 3:1 | 0.55 | 0.49 | 33 | 27 | 1:1 | 0.52 |
| Teal x 9A | 492 | 141 | 3:1 | 0.12 | 0.66 | 42 | 34 | 1:1 | 0.39 |
| Teal x 10A | 701 | 231 | 3:1 | 0.91 | 0.87 | 27 | 20 | 1:1 | 0.38 |
| Teal x 11A | 505 | 189 | 3:1 | 0.19 | 0.32 | 34 | 30 | 1:1 | 0.71 |
| Teal x 15A | 893 | 74 | 15:1 | 0.08 | 0.39 | 45 | 20 | 3:1 | 0.35 |
| Teal x 16A | 587 | 168 | 3:1 | 0.09 | 0.33 | 26 | 23 | 1:1 | 0.78 |

Figure 3

| Cross | Resistant (R) | Segregating (Seg) | Susceptible (S) | Ratio Tested (R:Seg:S)[a] | P Value[b] | Total # Families |
|---|---|---|---|---|---|---|
| Teal x 1A | 12 | 28 | 10 | 1:2:1 | 0.64 | 50 |
| Teal x 9A | 15 | 23 | 12 | 1:2:1 | 0.66 | 50 |
| Teal x 10A | 9 | 27 | 14 | 1:2:1 | 0.52 | 50 |
| Teal x 11A | 14 | 26 | 8 | 1:2:1 | 0.40 | 48 |
| Teal x 15A | 36 | 55 | 9 | 7:8:1 | 0.21 | 100 |
| Teal x 16A | 12 | 25 | 11 | 1:2:1 | 0.94 | 48 |

Figure 4

| Cross | Resistant (R) | Susceptible (S) | Ratio tested (R:S) | P Value[a] |
|---|---|---|---|---|
| 1A x 9A | 506 | 0 | - | - |
| 1A x 10A | 567 | 0 | - | - |
| 1A x 15A | 501 | 0 | - | - |
| 1A x 16A | 814 | 0 | - | - |
| 1A x SWP965001 | 309 | 0 | - | - |
| 9A x 10A | 603 | 0 | - | - |
| 9A x 15A | 424 | 0 | - | - |
| 9A x 16A | 336 | 0 | - | - |
| 9A x SWP965001 | 407 | 0 | - | - |
| 10A x 15A | 547 | 0 | - | - |
| 10A x 16A | 409 | 0 | - | - |
| 10A x SWP965001 | 686 | 0 | - | - |
| 15A x 16A | 298 | 0 | - | - |
| 15A x SWP965001 | 410 | 0 | - | - |
| 16A x SWP965001 | 509 | 0 | - | - |
| SWP965001 x 11A | 688 | 47 | 15:1 | 0.93 |
| 1A x 11A | 735 | 56 | 15:1 | 0.37 |
| 11A x 9A | 446 | 42 | 15:1 | 0.00 |
| 11A x 10A | 557 | 46 | 15:1 | 0.19 |
| 11A x 15A | 600 | 14 | 63:1 | 0.20 |
| 11A x 16A | 390 | 34 | 15:1 | 0.16 |

Figure 5

| Cross | Resistant (R) | Segregating (Seg) | Susceptible (S) | Ratio Tested (R:Seg:S)$^a$ | P Value$^b$ | Total # Families |
|---|---|---|---|---|---|---|
| SWP965001 x 11A | 32 | 42 | 7 | 7:8:1 | 0.57 | 81 |
| 1A x 11A | 33 | 58 | 9 | 7:8:1 | 0.07 | 100 |
| 11A x 9A | 36 | 49 | 5 | 7:8:1 | 0.77 | 90 |
| 11A x 10A | 34 | 59 | 7 | 7:8:1 | 0.14 | 100 |
| 11A x 16A | 45 | 47 | 7 | 7:8:1 | 0.86 | 99 |

Figure 6

| Imazamox Conc. (uM) | % Uninhibited AHAS Activity | | | |
|---|---|---|---|---|
| | Teal | 11A | BW755 | 15A |
| 0.8 | 71.1 | 84.8 | 90.0 | 92.6 |
| 1.6 | 55.2 | 71.2 | 76.9 | 88.4 |
| 3.1 | 41.8 | 59.7 | 65.7 | 84.3 |
| 6.3 | 30.9 | 50.3 | 56.6 | 80.3 |
| 12.5 | 22.3 | 42.9 | 49.6 | 76.3 |
| 25.0 | 16.2 | 37.6 | 44.5 | 72.5 |
| 50.0 | 12.6 | 34.3 | 41.4 | 68.8 |
| 100.0 | 11.4 | 33.1 | 40.4 | 65.2 |

Figure 7

| | 10X | | 30X | |
|---|---|---|---|---|
| Genotype | %Injured | %No Injury | %Injured | %No Injury |
| BW755 (one gene) | 100 | 0 | 100 | 0 |
| Teal 15A (two gene) | 0 | 100 | 100 | 0 |
| 15A/11A (three gene) | 33 | 67 | 48 | 52 |

Figure 8

| | | | | | | | | | | | | | | | | | | | | | SEQ ID NO: |
|---|---|---|---|---|---|---|---|---|---|---|---|---|---|---|---|---|---|---|---|---|---|
| M | A | T | T | A | A | A | A | A | A | L | S | A | A | A | T | A | K | T | G | R | K | N | H | Q | R | 14 |
| ATG | GCT | ACG | ACC | GCC | GCG | GCC | GCC | GCC | GCC | CTG | TCC | GCC | GCC | GCG | ACG | GCC | AAG | ACC | GGC | CGT | AAG | AAC | CAC | CAG | CGA | 13 |
| V | | | | | | | | | | | | | | | | | | | | | | | | | X | 16 |
| GT- | x | x | x | x | x | x | x | x | x | x | x | x | x | x | x | x | x | x | x | x | x | x | x | x | — | 15 |
| V | | | | | | | | | | | | | | | | | | | | | | | | | X | 18 |
| GT- | x | x | x | x | x | x | x | x | x | x | x | x | x | x | x | x | x | x | x | x | x | x | x | x | — | 17 |
| V | | | | | | | | | | | | | | | | | | | | | | | | | X | 20 |
| GT- | x | x | x | x | x | x | x | x | x | x | x | x | x | x | x | x | x | x | x | x | x | x | x | x | — | 19 |
| V | | | | | | | | | | | | | | | | | | | | | | | | | X | 22 |
| GT- | x | x | x | x | x | x | x | x | x | x | x | x | x | x | x | x | x | x | x | x | x | x | x | x | — | 21 |
| V | | | | | | | | | | | | | | | | | | | | | | | | | X | 24 |
| GT- | x | x | x | x | x | x | x | x | x | x | x | x | x | x | x | x | x | x | x | x | x | x | x | x | — | 23 |

| | | | | | | | | | | | | | | | | | | | | | SEQ ID NO: |
|---|---|---|---|---|---|---|---|---|---|---|---|---|---|---|---|---|---|---|---|---|---|
| H | V | L | P | A | R | G | R | V | G | A | A | A | V | R | C | S | A | V | S | P | V | T | P | P | S | 14 |
| CAC | GTC | CTT | CCC | GCT | CGA | GGC | CGG | GTG | GGG | GCG | GCG | GCG | GTC | AGG | TGC | TCG | GCG | GTG | TCC | CCG | GTC | ACC | CCG | CCG | TCC | 13 |
| x | x | x | x | x | x | x | x | x | x | x | x | x | x | x | x | x | x | x | x | x | x | x | x | x | x | 16 |
| x | — | | | | | | | | | | | | | | | | | | | | | | | | | 15 |
| x | x | x | x | x | x | x | x | x | x | x | x | x | x | x | x | x | x | x | x | x | x | x | x | x | x | 18 |
| x | — | | | | | | | | | | | | | | | | | | | | | | | | | 17 |
| x | x | x | x | x | x | x | x | x | x | x | x | x | x | x | x | x | x | x | x | x | x | x | x | x | x | 20 |
| x | — | | | | | | | | | | | | | | | | | | | | | | | | | 19 |
| x | x | x | x | x | x | x | x | x | x | x | x | x | x | x | x | x | x | x | x | x | x | x | x | x | x | 22 |
| x | — | | | | | | | | | | | | | | | | | | | | | | | | | 21 |
| x | x | x | x | x | x | x | x | x | x | x | x | x | x | x | x | x | x | x | x | x | x | x | x | x | x | 24 |
| x | — | | | | | | | | | | | | | | | | | | | | | | | | | 23 |

```
          380                390                400                                   430
           |                  |                  |                                     |
  K   Q   P   H   V   S   I   C   A   D   V   K   L   A   L   Q   L   N   A   L   L   Q   S   T   T
  AAG CAA CCA CAT GTG TCA ATT TGC GCA GAT GTT AAG CTT GCT TTA CAG TTG AAT GCT CTG CTA CAA AGC ACA ACA

K   Q   P   H   V   S   I   C   A   D   V   K   L   A   L   Q   L   N   D   L   L   Q   S   K   A
  AAG CAG CCA CAT GTC TCC ATT TGT GCA GAT GTT AAG CTT GCT TTA CAG TTG AAT GAT CTA TTA CAG AGC AAA GCA

K   Q   P   H   V   S   I   C   A   D   V   K   L   A   L   Q   L   N   D   L   L   Q   S   K   A
  AAG CAG CCA CAT GTC TCC ATT TGT GCA GAT GTT AAG CTT GCT TTA CAG TTG AAT GAT CTA TTA CAG AGC AAA GCA

K   Q   P   H   V   S   I   C   A   D   V   K   L   A   L   Q   L   N   D   L   L   Q   S   K   A
  AAN CAG CCA CAT GTC TCC ATT TGT GCA GAT GTT AAG CTT GCT TTA CAG TTG AAT GAT CTA TTA CAG AGC AAA GCA

K   Q   P   H   V   S   I   C   A   D   V   K   L   A   L   Q   L   N   D   L   L   Q   S   K   A
  AAG CAG CCA CAT GTC TCC ATT TGT GCC GAT GTT AAG CTT GCT TTA CAG TTG AAT GAT CTA TTA CAG AGC AAA GCA

K   Q   P   H   V   S   I   C   A   D   V   K   L   A   L   Q   L   N   D   L   L   Q   S   K   A
  AAG CAG CCA CAT GTC TCC ATT TGT GCA GAT GTT AAN CTT GCT TTA CAG TTG AAT GAT CTA TTA CAG AGC AAA GCA 410                    420                              430
                            |                      |                                |
  K   T   S   D   F   S   A   W   H   N   E   L   D   Q   K   R   E   F   P   L   G   Y   K   T   F
  AAG ACA AGT TCT GAT TTT AGT GCA TGG CAC AAT GAG TTG GAC CAG AAG AGG GAG TTT CCT CTG GGG TAC AAA ACT TTT

Q   Q   G   L   D   F   G   P   W   H   K   L   D   Q   K   R   E   F   P   L   G   F   K   T   F
  CAA CAG GGT CTG GAT TTT GGT CCA TGG CAC AAG TTG GAT CAG AAG AGG GAG TTT CCT CTA GGA TTC AAG ACT TTT

Q   Q   G   L   D   F   G   P   W   H   K   L   D   Q   K   R   E   F   P   L   G   F   K   T   F
  CAA CAG GGT CTG GAT TTT GGT CCA TGG CAC AAG TTG GAT CAG AAG AGG GAG TTT CCT CTA GGA TTC AAG ACT TTT

Q   Q   G   L   D   F   G   P   W   H   K   L   D   Q   K   R   E   F   P   L   G   F   K   T   F
  CAA CAG GGT CTG GAT TTT GGT CCA TGG CAC AAG TTG GAT CAG AAG AGG GAG TTT CCT CTA GGA TTC AAG ACT TTT

Q   Q   G   L   D   F   G   P   W   H   K   L   D   Q   K   R   E   F   P   L   G   F   K   T   F
  CAA CAG GGT CTG GAT TTT GGT CCA TGG CAC AAG TTG GAT CAG AAG AGG GAG TTT CCT CTA GGA TTC AAG ACT TTT

Q   Q   G   L   D   F   G   P   W   H   K   L   D   Q   K   R   E   F   P   L   G   F   K   T   F
  CAA CAG GGT CTG GAT TTT GGT CCA TGG CAC AAG TTG GAT CAG AAN AAN AGG GAG TTT CCT CTA GGA TTC AAG ACT TTT
```

```
        550                                                     560
---------+---------+---------+---------+---------+---------+---------+
 H   L   G   M   V   Q   W   E   D   R   F   Y   K   A   N   R   A   H   T   Y   L   G   N   P   E   C
CAT TTG GGT ATG GTG CAA TGG GAG GAT AGG TTT TAC AAG GCG AAT AGG GCG CAT ACA TAC TTG GGC AAC CCG GAA TGT

H   L   G   M   V   Q   W   E   D   R   F   Y   K   A   N   R   A   H   T   Y   L   G   N   P   E   N
CAT CTG GGA ATG GTG CAG TGG GAG GAT AGG TTT TAC AAG GCC AAT CGG GCG CAC ACA TAC CTT GGC AAC CCA GAA AAT

H   L   G   M   V   Q   W   E   D   R   F   Y   K   A   N   R   A   H   T   Y   L   G   N   P   E   N
CAT CTG GGA ATG GTG CAG TGG GAG GAT AGG TTT TAC AAG GCC AAT CGG GCG CAC ACA TAC CTT GGC AAC CCA GAA AAT

H   L   G   M   V   Q   W   E   D   R   F   Y   K   A   N   R   A   H   T   Y   L   G   N   P   E   N
CAT CTG GGA ATG GTG CAG TGG GAG GAT AGG TTT TAC AAG GCC AAT CGG GCG CAC ACA TAC CTT GGC AAC CCA GAA AAT

H   L   G   M   V   Q   W   E   D   R   F   Y   K   A   N   R   A   H   T   Y   L   G   N   P   E   N
CAT CTG GGA ATG GTG CAG TGG GAG GAT AGG TTT TAC AAG GCC AAT CGG GCG CAC ACA TAC CTT GGC AAC CCA GAA AAT

H   L   G   M   V   Q   W   E   D   R   F   Y   K   A   N   R   A   H   T   Y   L   G   N   P   E   N
CAT CTG GGA ATG GTG CAG TGG GAG GAT AGG TTT TAC AAG GCC AAT CGG GCG CAC ACA TAC CTT GGC AAC CCA GAA AAT

590
---------+---------+---------+---------+---------+---------+---------+
 E   S   E   I   Y   P   D   F   V   T   I   A   K   G   F   N   I   P   A   V   R   V   T   K   K   S   E
GAG AGC GAG ATA TAT CCA GAT TTT GTG ACT ATT GCT AAG GGG TTC AAT ATT CCT GCA GTC CGT GTA ACA AAG AGT GAA

E   S   E   I   Y   P   D   F   V   T   I   A   K   G   F   N   V   P   A   V   R   V   T   K   K   S   E
GAG AGT GAG ATA TAT CCA GAT TTT GTG ACG ATT GCT AAA GGA TTC AAC GTT CCA GCA GTT CGA GTG ACG AAG AGC GAA

E   S   E   I   Y   P   D   F   V   T   I   A   K   G   F   N   V   P   A   V   R   V   T   K   K   S   E
GAG AGT GAG ATA TAT CCA GAT TTT GTG ACG ATT GCT AAA GGA TTC AAC GTT CCA GCA GTT CGA GTG ACG AAG AGC GAA

E   S   E   I   Y   P   D   F   V   T   I   A   K   G   F   N   V   P   A   V   R   V   T   K   K   S   E
GAG AGT GAG ATA TAT CCA GAT TTT GTG ACG ATT GCT AAA GGA TTC AAC GTT CCA GCA GTT CGA GTG ACG AAG AGC GAA

E   S   E   I   Y   P   D   F   V   T   I   A   K   G   F   N   V   P   A   V   R   V   T   K   K   S   E
GAG AGT GAG ATA TAT CCA GAT TTT GTG ACG ATT GCT AAA GGA TTC AAC GTT CCA GCA GTT CGA GTG ACG AAG AGC GAA

E   S   E   I   Y   P   D   F   V   T   I   A   K   G   F   N   V   P   A   V   R   V   T   K   K   S   E
GAG AGT GAG ATA TAT CCA GAT TTT GTG ACG ATT GCT AAA GGA TTC AAC GTT CCA GCA GTT CGA GTG ACG AAG AGC GAA 570                                                     580
```

| | | | | | | | | | | | | | | | | | | | | | SEQ ID NO: |
|---|---|---|---|---|---|---|---|---|---|---|---|---|---|---|---|---|---|---|---|---|---|
| M | A | T | T | A | A | A | A | A | A | L | S | A | A | A | T | A | K | T | G | R | K | N | H | Q | R | |
| ATG | GCT | ACG | ACC | GCC | GCG | GCC | GCC | GCC | GCC | CTG | TCC | GCC | GCC | GCC | ACG | GCC | AAG | ACC | GGC | CGT | AAG | AAC | CAC | CAG | CGA | 14 13 |
| V | | | | | | | | | | | | | X | | | | | | | | | | | | | 26 |
| GT- | X | X | X | X | X | X | X | X | X | X | X | X | | X | X | X | X | X | X | X | X | X | X | X | X | 25 |
| V GT- | X | X | X | X | X | X | X | X | X | X | X | X | X | X | X | X | X | X | X | X | X | X | X | X | X | 28 27 |
| V GT- | X | X | X | X | X | X | X | X | X | X | X | X | X | X | X | X | X | X | X | X | X | X | X | X | X | 30 29 |
| V GT- | X | X | X | X | X | X | X | X | X | X | X | X | X | X | X | X | X | X | X | X | X | X | X | X | X | 32 31 |
| V GT- | X | X | X | X | X | X | X | X | X | X | X | X | X | X | X | X | X | X | X | X | X | X | X | X | X | 34 33 |
| H | H | V | L | P | A | R | G | V | G | A | A | A | V | R | C | S | A | V | S | P | V | T | P | P | S | |
| CAC | CAC | GTC | CTT | CCC | GCT | CGA | GGC | GTG | GGG | GCG | GCG | GCG | GTC | AGG | TGC | TCG | GCG | GTG | TCC | CCG | GTC | ACC | CCG | CCG | TCC | 14 13 |
| X | X | X | X | X | X | X | X | X | X | X | X | X | X | X | X | X | X | X | X | X | X | X | X | X | X | 26 25 |
| X | X | X | X | X | X | X | X | X | X | X | X | X | X | X | X | X | X | X | X | X | X | X | X | X | X | 28 27 |
| X | X | X | X | X | X | X | X | X | X | X | X | X | X | X | X | X | X | X | X | X | X | X | X | X | X | 30 29 |
| X | X | X | X | X | X | X | X | X | X | X | X | X | X | X | X | X | X | X | X | X | X | X | X | X | X | 32 31 |
| X | X | X | X | X | X | X | X | X | X | X | X | X | X | X | X | X | X | X | X | X | X | X | X | X | X | 34 33 |

```
         110                 120                 130
      ----+-------------------+-------------------+----
       V   I   T   N   H   L   F   R   H   E   Q   G   E   A   F   A   A   S   G   Y   A   R   A   S   G   R   V
      GTC ATC ACC AAC CAC CTC TTC CGC CAC GAG CAG GGG GAG GCG TTC GCG GCG TCC GGG TAC GCG CGC GCG TCC GGG CGC GTC

V   I   T   N   H   L   F   R   H   E   Q   G   E   A   F   A   A   S   G   Y   A   R   A   S   G   R   V
      GTC ATC ACC AAC CAC CTC TTC CGC CAC GAG CAG GGG GAG GCG TTC GCG GCG TCC GGG TAC GCG CGC GCG TCC GGG CGC GTC

V   I   T   N   H   L   F   R   H   E   Q   G   E   A   F   A   A   S   G   Y   A   R   A   S   G   R   V
      GTC ATC ACC AAC CAC CTC TTC CGC CAC GAG CAG GGG GAG GCG TTC GCG GCG TCC GGG TAC GCG CGC GCG TCC GGG CGC GTC

V   I   T   N   H   L   F   R   H   E   Q   G   E   A   F   A   A   S   G   Y   A   R   A   S   G   R   V
      GTC ATC ACC AAC CAC CTC TTC CGC CAC GAG CAG GGG GAG GCG TTC GCG GCG TCC GGG TAC GCG CGC GCG TCC GGG CGC GTC

V   I   T   N   H   L   F   R   H   E   Q   G   E   A   F   A   A   S   G   Y   A   R   A   S   G   R   V
      GTC ATC ACC AAC CAC CTC TTC CGC CAC GAG CAG GGG GAG GCG TTC GCG GCG TCC GGG TAC GCG CGC GCG TCC GGG CGC GTC

V   I   T   N   H   L   F   R   H   E   Q   G   E   A   F   A   A   S   G   Y   A   R   A   S   G   R   V
      GTC ATC ACC AAC CAC CTC TTC CGC CAC GAG CAG GGG GAG GCG TTC GCG GCG TCC GGG TAC GCG CGC GCG TCC GGG CGC GTC

V   I   T   N   H   L   F   R   H   E   Q   G   E   A   F   A   A   S   G   Y   A   R   A   S   G   R   V
      GTC ATC ACC AAC CAC CTC TTC CGC CAC GAG CAG GGG GAG GCG TTC GCG GCG TCC GGG TAC GCG CGC GCG TCC GGG CGC GTC 140                 150                 160
      ----+-------------------+-------------------+----
       G   V   C   V   A   T   S   G   P   G   A   T   N   L   V   S   A   L   A   D   A   L   L   D   S   V   P
      GGG GTC TGC GTC GCC ACC TCC GGC CCC GGG GCA ACC AAC CTC GTG TCC GCC GAC GCG CTG CTC GAC TCC GTC CCG

G   V   C   V   A   T   S   G   P   G   A   T   N   L   V   S   A   L   A   D   A   L   L   D   S   I   P
      GGC GTC TGC GTC GCC ACC TCC GGG CCG GGG GCC ACC AAC CTC GTC TCC GCC GAC GCT CTC CTC GAC TCC ATC CCC

G   V   C   V   A   T   S   G   P   G   A   T   N   L   V   S   A   L   A   D   A   L   L   D   S   I   P
      GGC GTC TGC GTC GCC ACC TCC GGG CCG GGG GCC ACC AAC CTC GTC TCC GCC GAC GCT CTC CTC GAC TCC ATC CCC

G   V   C   V   A   T   S   G   P   G   A   T   N   L   V   S   A   L   A   D   A   L   L   D   S   I   P
      GGC GTC TGC GTC GCC ACC TCC GGG CCG GGG GCC ACC AAC CTC GTC TCC GCC GAC GCT CTC CTC GAC TCC ATC CCC

G   V   C   V   A   T   S   G   P   G   A   T   N   L   V   S   A   L   A   D   A   L   L   D   S   I   P
      GGC GTC TGC GTC GCC ACC TCC GGG CCG GGG GCC ACC AAC CTC GTC TCC GCC GAC GCT CTC CTC GAC TCC ATC CCC

G   V   C   V   A   T   S   G   P   G   A   T   N   L   V   S   A   L   A   D   A   L   L   D   S   I   P
      GGC GTC TGC GTC GCC ACC TCC GGG CCG GGG GCC ACC AAC CTC GTC TCC GCC GAC GCT CTC CTC GAC TCC ATC CCC

G   V   C   V   A   T   S   G   P   G   A   T   N   L   V   S   A   L   A   D   A   L   L   D   S   I   P
      GGC GTC TGC GTC GCC ACC TCC GGG CCG GGG GCC ACC AAC CTC GTC TCC GCC GAC GCT CTC CTC GAC TCC ATC CCC
```

```
        380                                     390                                     400
         +-----------+-----------+-----------+-----------+-----------+-----------+
     K   Q   P   H   V   S   I   C   A   D   V   K   L   A   L   Q   G   L   N   A   L   L   Q   Q   S   K   T
    AAG CAA CCA CAT GTG TCA ATT TGC GCA GAT GTT AAG CTT GCT TTA CAG GGC TTG AAT GCT CTG CTA CAA CAG AGC ACA ACA

K   Q   P   H   V   S   I   C   A   D   V   K   L   A   L   Q   G   L   N   A   L   L   N   G   S   K   A
    AAG CAG CCA CAT GTC TCC ATT TGT GCA GAT GTT AAG CTT GCT TTA CAG GGG TTG AAT GCT CTA TTA AAT GGG AGC AAA GCA

K   Q   P   H   V   S   I   C   A   D   V   K   L   A   L   Q   G   L   N   A   L   L   N   G   S   K   A
    AAG CAG CCA CAT GTC TCC ATT TGT GCA GAT GTT AAG CTT GCT TTA CAG GGG TTG AAT GCT CTA TTA AAT GGG AGC AAA GCA

K   Q   P   H   V   S   I   C   A   D   V   K   L   A   L   Q   G   L   N   A   L   L   N   G   S   K   A
    AAG CAG CCA CAT GTC TCC ATT TGT GCA GAT GTT AAG CTT GCT TTA CAG GGG TTG AAT GCT CTA TTA AAT GGG AGC AAA GCA

K   Q   P   H   V   S   I   C   A   D   V   K   L   A   L   Q   G   L   N   A   L   L   N   G   S   K   A
    AAG CAG CCA CNT GTC TCC ATT TGT GCA GAT GTT AAN CTT GCT TTA CAG GGG TTG AAT GCN CTA TTA AAT GGG AGC AAA GCA

K   Q   P   H   V   S   I   C   A   D   V   K   L   A   L   Q   G   L   N   A   L   L   N   G   S   K   A
    AAG CAG CCA CAT GTC TCC ATT TGT GCA GAT GTT AAG CTT GCT TTA CAG GGG TTG AAT GCT CTA TTA AAT GGG AGC AAA GCA

K   Q   P   H   V   S   I   C   A   D   V   K   L   A   L   Q   G   L   N   A   L   L   N   G   S   K   A
    AAG CAG CCA CAT GTC TCC ATT TGT GCA GAT GTT AAG CTT GCT TTA CAG GGG TTG AAT GCT CTA TTA AAT GGG AGC AAA GCA
                                410                                     420                                     430
         +-----------+-----------+-----------+-----------+-----------+-----------+
     K   T   S   D   F   S   A   W   H   N   E   L   D   Q   L   Q   K   R   E   F   P   L   G   Y   K   T   F
    AAG ACA AGT TCT GAT TTT AGT GCA TGG CAC AAT GAG TTG GAC CAG TTA CAG AAG AGG GAG TTT CCT CTG GGG TAC AAA ACT TTT

Q   Q   G   L   D   F   G   P   W   H   K   E   L   D   Q   L   Q   K   R   E   F   P   L   G   F   K   F
    CAA CAG GGT CTG GAT TTT GGT CCA TGG CAC AAG GAG TTG GAT CAG CAG AAG AAG AGG GAG TTC CCT CTA GGA TTC AAG ACT TTT

Q   Q   G   L   D   F   G   P   W   H   K   E   L   D   Q   L   Q   K   R   E   F   P   L   G   F   K   F
    CAA CAG GGT CTG GAT TTT GGT CCA TGG CAC AAG GAG TTG GAT CAG CAG AAG AAG AGG GAG TTC CCT CTA GGA TTC AAG ACT TTT

Q   Q   G   L   D   F   G   P   W   H   K   E   L   D   Q   L   Q   K   R   E   F   P   L   G   F   K   F
    CAA CAG GGN CTG GAT TTT GGT CCA TGG CNC AAG GAG TTG GAT CAA CAG AAG ANG AGG GAG TTC CCT CTA GGA TTC AAN ACT TTT

Q   Q   G   L   D   F   G   P   W   H   K   E   L   D   Q   L   Q   K   R   E   F   P   L   G   F   K   F
    CAA CAG GGT CTG GAT TTT GGT CCA TGG CAC AAG GAG TTG GAT CAG CAG AAG AAG AGG GAG TTC CCT CTA GGA TTC AAG ACT TTT

Q   Q   G   L   D   F   G   P   W   H   K   E   L   D   Q   L   Q   K   R   E   F   P   L   G   F   K   F
    CAA CAG GGT CTG GAT TTT GGT CCA TGG CAC AAG GAG TTG GAT CAG CAG AAG AAG AGG GAG TTC CCT CTA GGA TTC AAG ACT TTT
```

```
                600              610              620
                  +----------------+----------------+----------------+
V   R   A   A   I   K   M   L   E   T   P   G   Y   L   D   I   I   V   P   H   Q   E   H   V
GTC CGT GCC GCC ATC AAG ATG CTC GAG ACT CCA GGG TAC TTG GAT ATC ATC GTC CCG CAC CAG GAG CAT GTG

V   T   A   A   I   K   M   L   E   T   P   G   Y   L   D   I   H   I   V   P   H   Q   E   H   V
GTC ACT GCA GCA ATC AAG ATG CTT GAG ACC CCA GGG TAC TTG GAT ATT GTC CCG CAT CAG GAG CAC GTG

V   T   A   A   I   K   M   L   E   T   P   G   Y   L   D   I   I   V   P   H   Q   E   H   V
GTC ACT GCA GCA ATC AAG ATG CTT GAG ACC CCA GGG TAC TTG GAT ATC ATT GTC CCG CAT CAG GAG CAC GTG

V   T   A   A   I   K   M   L   E   T   P   G   Y   L   D   I   I   V   P   H   Q   E   H   V
GTC ACT GCA GCA ATC AAG ATG CTT GAG ACC CCA GGG TAC TTG GAT ATC ATT GTC CCG CAT CAG GAG CAC GTG

V   T   A   A   I   K   M   L   E   T   P   G   Y   L   D   I   I   V   P   H   Q   E   H   V
GTC ACT GCA GCA ATC AAG ATG CTT GAG ACC CCA GGG TAC TTG GAT ATC ATT GTC CCG CAT CAG GAG CAC GTG

V   T   A   A   I   K   M   L   E   T   P   G   Y   L   D   I   I   V   P   H   Q   E   H   V
GTC ACT GCA GCA ATC AAG ATG CTT GAG ACC CCA GGG TAC TTG GAT ATC ATT GTC CCG CAT CAG GAG CAC GTG 630              640
                  +----------------+----------------+----------------+
L   P   M   I   P   S   G   G   A   F   K   D   M   I   L   D   G   D   G   R   T   V   Y
CTG CCT ATG ATC CCA AGT GGG GGC GCA TTC AAG GAC ATG ATC CTG GAT GGT GAT GGC AGG ACT GTG TAT TAA

L   P   M   I   P   S   G   G   A   F   K   D   M   I   M   E   G   D   G   R   T   S
CTG CCT ATG ATC CCA AGC GGT GGT GCT TTT AAG GAC ATG ATC ATG GAG GGT GAT GGC AGG ACC TCG TAC

L   P   M   I   P   S   G   G   A   F   K   D   M   I   M   E   G   D   G   R   T   S
CTG CCT ATG ATC CCA AGC GGT GGT GCT TTT AAG GAC ATG ATC ATG GAG GGT GAT GGC AGG ACC TCG TAC

L   P   M   I   P   S   G   G   A   F   K   D   M   I   M   E   G   D   G   R   T   S
CTG CCT ATG ATC CCA AGC GGT GGT GCT TTT AAG GAC ATG ATC ATG GAG GGT GAT GGC AGG ACC TCG TAC

L   P   M   I   P   N   G   G   A   F   K   D   M   I   M   E   G   D   G   R   T   S
CTG CCT ATG ATC CCA AAC GGT GGT GCT TTT AAG GAC ATG ATC ATG GAG GGT GAT GGC AGG ACC TCG TAC

L   P   M   I   P   S   G   G   A   F   K   D   M   I   M   E   G   D   G   R   T   S
CTG CCT ATG ATC CCA AGC GGT GGT GCT TTT AAG GAC ATG ATC ATG GAG GGT GAT GGC AGG ACC TCG TAC
```

Figure 10

Partial DNA sequence and deduced amino acid sequence of TealMI115A

SEQ ID NO:2             D   V   F   A   Y   P   G   G   A   S   M   E   I   H   Q   A   L   T   R   S   P
SEQ ID NO:1           C GAC GTC TTC GCC TAC CCC GGC GGG GCC TCC ATG GAG ATC CAC CAG GCG CTG ACG CGC TCG CCC

V   I   T   N   H   L   F   R   H   E   Q   G   G   E   A   F   A   A   S   G   Y   A   R   A   S   G   R   V
GTC ATC ACC AAC CAC CTC TTC CGC CAC GAG CAG GGG GAG GCG TTC GCG GCG TCC GGC TAC GCC CGC GCG TCC GGC CGC GTC

G   V   C   V   A   T   S   G   P   G   A   T   N   L   V   S   A   L   A   D   A   L   L   D   S   I   P
GGC GTC TGC GTC GCC ACC TCC GGC CCG GGG GCC ACC AAC CTC GTC TCC GCG CTC GCC GAC GCC CTC CTC GAC TCC ATC CCC

M   V   A   I   T   G   Q   V   P   R   M   I   G   T   D   A   F   Q   E   T   P   I   V   E   V   T
ATG GTC GCC ATC ACG GGC CAG GTC CCC CGC ATG ATC GGC ACG GAC GCG TTC CAG GAG ACG CCC ATA GTG GAG GTC ACG

R   S   I   T   K   H   N   Y   L   V   L   D   V   E   D   I   P   R   V   I   Q   E   A   F   F   L   A
CGC TCC ATC ACC AAG CAC AAC TAC CTG GTC CTT GAC GTC GAG GAT ATC CCC CGC GTC ATC CAG GAA GCC TTC TTC CTT GCA

S   S   G   R   P   G   P   V   L   V   D   I   P   K   D   I   Q   Q   M   A   V   P   V   W   D   T
TCC TCT GGC CGC CCG GGG CCG GTG CTA GTT GAT ATC CCC AAG GAC ATC CAG CAG ATG GCT GTG CCC GTC TGG GAC ACT

P   M   S   L   P   G   Y   I   A   R   L   P   K   P   P   S   T   E   S   L   E   Q   V   L   R   L   V
CCA ATG AGT TTG CCA GGG TAC ATC GCC CGC CTG CCC AAG CCA CCA TCT ACT GAA TCG CTT GAG CAG GTC CTG CGT CTG GTT

G   E   S   R   R   P   I   L   Y   V   G   G   G   C   A   A   S   G   E   E   L   R   R   F   V   E   L
GGC GAG TCA CGG CGC CCA ATT CTG TAT GTT GGT GGC GGT TGC GCT GCG TCT GCG GAG GAG TTG CGC CGC TTT GTT GAG CTT

T   G   I   P   V   T   T   T   L   M   G   L   G   N   F   P   S   D   D   P   L   S   L   R   M   L   G
ACT GGG ATT CCA GTT ACA ACT ACT CTG ATG GGC CTT GGC AAC TTC CCC AGC GAC GAC CCA CTG TCT CTG CGC ATG CTT GGG

Figure 10 continued

```
  M   H   G   T   V   Y   A   N   Y   A   V   D   K   A   D   L   L   I   A   F   G   V   R   F   D   D   R
 ATG CAT GGC ACT GTG TAT GCA AAT TAT GCA GTA GAT AAG GCT GAC CTG TTG NTC GCA TTT GGT GTG CGG TTT GAT GAT CGT

V   T   G   K   I   E   A   F   A   S   R   S   K   I   E   H   I   D   P   A   E   I   G   K   N
 GTG ACT GGG AAA ATC GAG GCT TTT GCA AGC AGG TCC AAG ATT GNG CAC ATT GAC CCA GCT GAG ATT GGC AAG AAC

K   Q   P   H   V   S   I   C   A   D   V   K   L   A   L   Q   L   N   D   L   N   G   S   K   A
 AAG CAG CCA CAT GTC TCC ATT TGT GCA GAT GTT AAN CTT GCT CTT TTA CAG GGG TTG AAT GAT CTA AAT GGG AGC AAA GCA

Q   Q   G   L   D   F   L   I   D   Q   K   E   L   D   Q   R   E   F   P   L   G   F   K   T   F
 CAA CAG GGT CTG GAT TTT CTG ATT GAT CAG AAG GAG TTG GAT CAG AGG GAG TTT CCT CTA GGA TTC AAG ACT TTT

G   E   A   I   P   P   Q   Y   A   I   Q   V   L   D   E   L   T   K   G   E   A   I   A   T   G   V
 GGC GAG GCC ATC CCG CCA CAA TAT GCT ATC CAG GTA CTG GAT GAG CTG ACA AAA GGG GAG GCG ATT GCC ACT GGT GTT

G   Q   H   Q   M   W   A   Q   Y   T   Y   K   R   P   R   Q   W   L   S   G   L   G   A
 GGG CAG CAC CAG ATG TGG GCG CAG TAT TAC ACT TAC AAG CGG CCA CGG CAG TGG CTG TCT GGT TTG GGG GCA

M   G   F   L   M   N   I   Q   E   L   A   L   I   R   N   P   G   V   T   V   K   V   M   I   L   N   N   Q
 ATG GGG TTT CTC ATG AAC ATT CAG GAG TTG GCG TTG ATC CGC AAC CCA GGT GTT ACA GTT AAG GTG ATG ATA TTG AAC AAC CAG

S   F   G   M   V   V   Q   W   E   D   R   F   Y   K   A   N   R   A   H   T   Y   L   G   N   P   E   N
 AGT TTC GGA ATG GTG GTG CAG TGG GAG GAT AGG TTT TAC AAG GCC AAT CGG CAC ACA TAC CTT GGC AAC CCA GAA AAT

H   L   G   M   V   Q   V   Q   W   E   D   R   F   Y   K   A   N   R   A   H   T   Y   L   G   D   G
 CAT CTG GGA ATG GTG GTG CAG TGG GAG GAT AGG TTT TAC AAG GCC AAT CGG CAC ACA TAC CTT GAT GGT

S   E   I   Y   P   D   F   V   T   I   A   K   G   P   N   V   P   A   V   R   V   T   K   S   E
 AGT GAG ATA TAT CCA GAT TTT GTG ACG ATT GCT AAA GGA CCA AAC GTT CCA GCA GTT CGA GTG ACG AAG AGC GAA
```

Figure 10 continued

```
V   T   A   A   I   K   K   M   L   E   T   P   G   P   Y   L   L   D   I   I   V   P   H   Q   E   H   V
GTC ACT GCA GCA ATC AAG AAG ATG CTT GAG ACC CCA GGG CCA TAC TTG TTG GAT ATC ATA GTC CCG CAT CAG GAG CAC GTG

L   P   M   I   P   N   G   G   A   F   K   D   M   I   M   E   G   D   G   R   T   S   Y
CTG CCT ATG ATC CCA AAC GGT GGT GCT TTC AAG GAC ATG ATC ATG GAG GGT GAT GGC AGG ACC TCG TAC TGA
```

Figure 11

Partial DNA sequence and deduced amino acid sequence of TealIMI2 11A

```
SEQ ID NO:4           D   V   F   A   Y   P   G   G   A   S   M   E   I   H   Q   A   L   T   R   S   P
SEQ ID NO:3         C GAC GTC TTC GCC TAC CCT GGC GGC GCG TCC ATG GAG ATC CAC CAG GCG CTG ACG CGC TCG CCA

V   I   T   N   H   L   F   R   H   E   Q   E   A   F   A   A   S   G   Y   A   R   A   S   G   R   V
    GTC ATC ACC AAC CAC CTC TTC CGC CAC GAG CAG GAG GCG TTC GCG GCG TCC GGG TAC GCG CGC GCG TCC GGC CGC GTC

G   V   C   V   A   T   S   G   P   G   A   T   N   L   V   S   A   L   A   D   A   L   L   D   S   I   P
    GGC GTC TGC GTC GCC ACC TCC GGC CCG GGG GCC ACC AAC CTC GTC TCC GCC CTC GCC GAC GCT CTC CTC GAC TCC ATC CCC

M   V   A   I   T   G   Q   V   P   R   R   M   I   G   T   D   A   F   Q   E   T   P   I   V   E   V   T
    ATG GTC GCC ATC ACG GGC CAG GTC CCC CGC CGC ATG ATC GGC ACG GAT GCG TTC CAG GAG ACG CCC ATC GTG GAG GTC ACG

R   S   I   T   K   H   N   Y   L   V   D   V   E   D   I   P   R   V   I   Q   E   A   F   F   L   A
    CGC TCC ATC ACC AAG CAC AAC TAC CTG GTC GTC GAC GTG GAG GAT ATC CCC CGC GTC ATC CAG GAA GCC TTC TTC CTC GCA

S   G   R   P   G   P   V   L   V   D   I   P   K   D   I   Q   Q   M   A   V   P   V   W   D   T
    TCC TCT GGC CGC CCG GGG CCG GTG CTG GTT GAT ATC CCC AAG GAC ATC CAG CAG ATG GCT GTG CCT GTC TGG GAC ACG

P   M   S   L   P   G   Y   I   A   R   L   P   P   K   P   P   S   T   E   S   L   E   Q   V   R   L   V
    CCG ATG AGT TTG CCA GGG TAC ATC GCC CGC CTG CCC CCC AAG CCA CCA TCT ACT GAA TCG CTT GAG CAG GTC CTG CGT GTT

G   E   S   R   R   P   I   L   Y   V   G   G   G   C   A   A   S   G   E   E   L   R   R   F   V   E   L
    GGC GAG TCA CGG CGC CCA ATT CTG TAT GGT GGT GGC TGC GCT GCA TCT GCA TCT GGT GAG GAG TTG CGC CGC TTT GTT GAG CTC

T   G   I   P   V   T   T   T   L   M   G   L   G   N   F   P   S   D   D   P   L   S   L   R   M   L   G
    ACT GGG ATT CCA GTT ACA ACT ACT CTT ATG GGC CTT GGC AAC TTC CCC AGT GAC GAC CCA CTG TCT CTG CGC ATG CTG GGG
```

Figure 11 continued

```
M   H   G   T   V   Y   A   N   Y   A   V   D   K   A   D   L   L   L   A   F   G   V   R   F   D   D   R
ATG CAT GGC ACT GTG TAT GCA AAT TAT GCA GTA GAT AAG GCT GAC CTG TTG CTT GCA TTT GGT GTG CGG TTT GAT GAT CGT

V   T   G   K   I   E   A   F   A   S   R   S   K   I   V   H   I   D   P   A   E   I   G   K   N
GTG ACC GGG AAA ATC GAG GCT TTT GCA AGC AGG TCC AAG ATT GTG CAC ATT GAC CCA GCT GAG ATT GGC AAG AAC

K   Q   P   H   V   S   I   C   A   D   V   K   L   A   L   N   A   L   N   G   S   K   A
AAG CAG CCA CAT GTC TCC ATT TGT GCA GAT GTT AAG CTT GCT TTA CAG GGG TTG AAT GGG AGC AAA GCA

Q   Q   G   L   D   F   G   P   W   H   K   E   L   D   Q   Q   K   R   E   F   P   L   G   F   K   T   F
CAA CAG GGT GGT CTG GAT TTT GGT CCA TGG CAC AAG GAG TTG GAT CAG CAG AAG AGG GAG TTT CCT CTA GGA TTC AAG ACT TTT

G   E   A   I   P   P   Q   Y   A   I   Q   V   L   D   E   L   T   K   G   E   A   I   A   T   G   V
GGT GAG GCC ATC CCG CAA TAT GCT ATC CAG GTA CTG GAT GAG CTG ACA AAA GGG ATC GCC ATT GCC ACC GGT GTT

G   Q   H   Q   M   W   A   A   Q   Y   Y   T   Y   K   R   P   R   Q   W   L   S   S   G   L   G   A
GGG CAG CAT CAG ATG TGG GCT GCG CAG TAT TAC ACT TAC AAG CGG CCA CGG CAG TGG CTG TCT TCA GGT TTG GGT GCA

M   G   F   G   L   P   A   A   A   G   A   V   A   N   P   G   V   T   V   D   I   D   G   D   G
ATG GGA TTT GGG TTG CCA GCA GCT GCA GCT GGC GTG GCC AAC CCA GGT GTT ACA GTT GAC ATT GAT GGG GAT GGT

S   F   L   M   N   I   Q   E   L   A   L   I   R   I   E   N   L   P   V   K   V   M   I   L   N   Q
AGT TTC CTC ATG AAC ATT CAG GAG TTG GCG TTG ATT CGT ATC GAG AAC CTC CCA GTG AAG GTG ATG ATA TTG AAC CAG

H   L   Q   M   V   V   Q   W   E   D   R   F   Y   K   A   N   R   A   H   T   Y   L   G   N   P   E   N
CAT CTG CAG ATG GTG GTG CAG TGG GAG GAT CGT TTT TAC AAG GCC AAC CGG GCG CAC ACA TAC CTT GGC AAC CCA GAA AAT

E   S   E   I   Y   P   D   F   V   T   I   A   K   G   F   N   V   P   A   V   R   V   T   K   S   E
GAG AGT GAG ATA TAT CCA GAT TTT GTG ACG ATT GCT AAA GGA TTC AAC GTT CCG GCA GTT CGT GTG ACG AAG AGC GAA
```

Figure 11 continued

```
V   T   A   A   I   K   K   M   L   E   T   P   G   P   Y   L   L   D   I   I   V   P   H   Q   E   H   V
GTC ACT GCA GCA ATC AAG AAG ATG CTT GAG ACC CCA GGG CCA TAC TTG TTG GAT ATC ATT GTC CCG CAT CAG GAG CAC GTG

L   P   M   I   P   N   G   G   A   F   K   D   M   I   M   E   G   D   G   R   T   S
CTG CCT ATG ATC CCA AAC GGT GGT GCT TTT AAG GAC ATG ATC ATG GAG GGT GAT GGC AGG ACC TCG TAC
```

Figure 12

```
Als1_ORF_Teal  (SEQ ID NO:5)
Als2_ORF_Teal  (SEQ ID NO:6)
Als3_ORF_Teal  (SEQ ID NO:7)
               Consensus Als1_ORF_Teal    (1) GTCTGCGTCGCCACCTCCGGCCGGGGGCCACCAACCTCGTCTCCGCGCT
Als2_ORF_Teal    (1) GTCTGCGTCGCCACCTCCGGCCGGGGGCCACCAACCTCGTCTCCGCGCT
Als3_ORF_Teal    (1) GTCTGCGTCGCCACCTCCGGCCGGGGGCCACCAACCTCGTCTCCGCGCT
     Consensus   (1) GTCTGCGTCGCCACCTCCGGCCGGGGGCCACCAACCTCGTCTCCGCGCT
                                                                    100

Als1_ORF_Teal   (51) CGCCGACGTCCCTCCTCGACTCCATCCCCATGGTCGCCATCACGGGCCAGG
Als2_ORF_Teal   (51) CGCCGACGTCTCTCCTCGACTCCATCCCCATGGTCGCCATCACGGGCCAGG
Als3_ORF_Teal   (51) CGCTGACGCCCCTCCTCGACTCCATCCCCATGGTCGCCATCACGGGCCAG
     Consensus  (51) CGCCGACGCCCCTCCTCGACTCCATCCCCATGGTCGCCATCACGGGCCAG
                                                                    150

Als1_ORF_Teal  (101) TCCCCCGCCGCATGATCGGCACGACGCGTTCAGGAGACGCCCATAGTG
Als2_ORF_Teal  (101) TCCCCCGCCGCATGATCGGCACGACGATGCGTTCAGGAGACGCCCATCGTG
Als3_ORF_Teal  (101) TCCCCCGCCGCATGATCGGCACGACGCGTTCAGGAGACGCCCATAGTG
     Consensus (101) TCCCCCGCCGCATGATCGGCACGACGCGTTCAGGAGACGCCCATAGTG
                                                                    200

Als1_ORF_Teal  (151) GAGGTCACGCGCTCCATCACCAAGCACAACTACCTGGTCTTGACGTGGA
Als2_ORF_Teal  (151) GAGGTCACGCGCTCCATCACCAAGCACAACTACCTGTCCTTGACGTGGA
Als3_ORF_Teal  (151) GAGGTCACGCGCTCCATCACCAAGCACAACTACCTGGTCTTGACGTGGA
     Consensus (151) GAGGTCACGCGCTCCATCACCAAGCACAACTACCTGGTCTTGACGTGGA
                                                                    250

Als1_ORF_Teal  (201) GGATATCCCCGCGTCATCCAGGAAGCCTTCTTCCTTGCATCCTCTGGCC
Als2_ORF_Teal  (201) GGATATCCCCGCGTCATCCAGGAAGCCTTCTTCCTTGCATCCTCTGGCC
Als3_ORF_Teal  (201) GGATATCCCCGCGTCATCCAGGAAGCCTTCTTCCTCGCGTCCTCTGGCC
     Consensus (201) GGATATCCCCGCGTCATCCAGGAAGCCTTCTTCCTTGCATCCTCTGGCC
                                                                    300

Als1_ORF_Teal  (251) GCCCGGGGCCGGTGCTAGTTGATATCCCAAGGACATCCAGCAGCAGATG
Als2_ORF_Teal  (251) GCCCGGGGCCGGTGCTGGTTGATATCCCAAGGACATCCAGCAGCAGAGATG
Als3_ORF_Teal  (251) GCCCGGGGCCGGTGCTGGTTGATATCCCAAGGACATATCCAGCAGCAGATG
     Consensus (251) GCCCGGGGCCGGTGCTGGTTGATATCCCAAGGACATCCAGCAGCAGATG
```

Figure 12 Continued

```
             301                                                  350
Als1_ORF_Teal      GCTGTGCCCGTCTGGGACACTCCAATGAGTTTGCCAGGGTACATCGCCCG
Als2_ORF_Teal      GCTGTGCCTGTCTGGGACACGCCGATGAGTTTGCCAGGGTACATCGCCCG
Als3_ORF_Teal      GCCGTGCCTATCTGGGACACGCCGATGAGTTTGCCAGGGTACATCGCCCG
Consensus          GCTGTGCCTGTCTGGGACACGCCGATGAGTTTGCCAGGGTACATCGCCCG
             351                                                  400
Als1_ORF_Teal      CCTGCCCAAGCCACCATCTACTGAATCGCTTGAGCAGGTCCTGCGTCTGG
Als2_ORF_Teal      CCTGCCCAAGCCACCATCTACTGAATCGCTTGAGCAGGTCCTGCGTCTGG
Als3_ORF_Teal      CCTGCCCAAGCCACCATCTACTGAATCGCTTGAGCAGGTCCTGCGTCTGG
Consensus          CCTGCCCAAGCCACCATCTACTGAATCGCTTGAGCAGGTCCTGCGTCTGG
             401                                                  450
Als1_ORF_Teal      TTGGGCGAGTCACGGCGCCCAATTCTGTATGTTGGTGGTGGCTGCGCTGCG
Als2_ORF_Teal      TTGGGCGAGTCACGGCGCCCAATTCTGTATGTTGGTGGTGGCTGCGCTGCA
Als3_ORF_Teal      TTGGGCGAGTCACGGCGCCCAATTCTGTATGTTGGTGGTGGCTGCGCTGCA
Consensus          TTGGGCGAGTCACGGCGCCCAATTCTGTATGTTGGTGGTGGCTGCGCTGCA
             451                                                  500
Als1_ORF_Teal      TCTGGGCGAGGAGTTGCGCGCCGCTTGTTGAGCTTACTGGGATTCCAGTTAC
Als2_ORF_Teal      TCTGGGCGAGGAGTTGCGCGCCGCTTGTTGAGCTCACTGGGATTCCAGTTAC
Als3_ORF_Teal      TCCGGGCGAGGAGTTGCGCGCCGCTTGTTGAGCTCACTGGGATTCCAGTTAC
Consensus          TCTGGGCGAGGAGTTGCGCGCCGCTTGTTGAGCTCACTGGGATTCCAGTTAC
             501                                                  550
Als1_ORF_Teal      AACTACTCTGATGGGCCTTGGCAACTTCCCCAGCGACGACCCACTGTCTC
Als2_ORF_Teal      AACTACTCTTATGGGCCTTGGCAACTTCCCCAGCGACGACCCACTGTCTC
Als3_ORF_Teal      AACTACTCTGATGGGCCTTGGCAACTTCCCCAGCGACGACCCACTGTCTC
Consensus          AACTACTCTGATGGGCCTTGGCAACTTCCCCAGCGACGACCCACTGTCTC
             551                                                  600
Als1_ORF_Teal      TGCGCATGCTTGGGATGCATGGCACTGTATGCAAATTATGCAGTAGAT
Als2_ORF_Teal      TGCGCATGCTGGGGATGCATGGCACTGTATGCAAATTATGCAGTAGAT
Als3_ORF_Teal      TGCGCATGCTTGGGATGCATGGCACTGTATGCAAATTATGCAGTCGAT
Consensus          TGCGCATGCTTGGGATGCATGGCACTGTATGCAAATTATGCAGTAGAT
```

Figure 12 Continued

```
              601                                                    650
Als1_ORF_Teal  (601) AAGGCTGACCTGTGCTGCTTGCTTGCATTTGGTGTGCGGTTTGATGATCGTGTGAC
Als2_ORF_Teal  (601) AAGGCTGACCTGTGCTGCTTGCTTGCATTTGGTGTGCGGTTTGATGATCGTGTGAC
Als3_ORF_Teal  (601) AAGGCTGACCTGTGCTGCTTGCTTGCATTTGGTGTGCGGTTTGATGATCGCGTGAC
    Consensus  (601) AAGGCTGACCTGTGCTGCTTGCTTGCATTTGGTGTGCGGTTTGATGATCGTGTGAC
              651                                                    700
Als1_ORF_Teal  (651) TGGGAAAATCGAGGCTTTTGCAAGCAGGTCCAAGATTGTGCACATTGACA
Als2_ORF_Teal  (651) CGGGAAAATCGAGGCTTTTGCAAGCAGGTCCAAGATTGTGCACATTGACA
Als3_ORF_Teal  (651) TGGGAAAATCGAGGCCTTTGCAAGCAGGTCCAAGATTGTGCACATTGACA
    Consensus  (651) TGGGAAAATCGAGGCTTTTGCAAGCAGGTCCAAGATTGTGCACATTGACA
              701                                                    750
Als1_ORF_Teal  (701) TTGACCCAGCTGAGATTGGCAAGAACAAGCAGCCACATGTCTCCATTTGT
Als2_ORF_Teal  (701) TTGACCCAGCTGAGATTGGCAAGAACAAGCAGCCACATGTCTCCATTTGT
Als3_ORF_Teal  (701) TTGACCCAGCTGAGATTGGCAAGAACAAGCAGCCACATGTCTCCATTTGT
    Consensus  (701) TTGACCCAGCTGAGATTGGCAAGAACAAGCAGCCACATGTCTCCATTTGT
              751                                                    800
Als1_ORF_Teal  (751) GCAGATGTTAAGCTTGCTTTACAGGGGTTGAATGATCTATTAAATGGGAG
Als2_ORF_Teal  (751) GCAGATGTTAAGCTTGCTTTACAGGGGTTGAATGCTCTATTAAATGGGAG
Als3_ORF_Teal  (751) GCAGATGTTAAGCTTGCTTTACAGGGGTTGAATGCTCTATTAAATGGGAG
    Consensus  (751) GCAGATGTTAAGCTTGCTTTACAGGGGTTGAATGCTCTATTAAATGGGAG
              801                                                    850
Als1_ORF_Teal  (801) CAAAGCACAACACAGGGTCTGGATTTTGGTCCATGCACAAGGAGTTGGATC
Als2_ORF_Teal  (801) CAAAGCACAACACAGGGTCTGGATTTTGGTCCATGCACAAGGAGTTGGATC
Als3_ORF_Teal  (801) CAAAGCACAACACAGGGTCTGGATTTTGGTCCATGCACAAGGAGTTGGATC
    Consensus  (801) CAAAGCACAACACAGGGTCTGGATTTTGGTCCATGCACAAGGAGTTGGATC
              851                                                    900
Als1_ORF_Teal  (851) AGCAGAAGAGGGAGTTTCCTCTAGAGATTCAAGACTTTTGGCGAGGCCATC
Als2_ORF_Teal  (851) AGCAGAAGAGGGAGTTTCCTCTAGAGATTCAAGACTTTTGGCGAGGCCATC
Als3_ORF_Teal  (851) AGCAGAAGAGGGAGTTTCCTCTAGAGATTCAAGACTTTTGGCGAGGCCATC
    Consensus  (851) AGCAGAAGAGGGAGTTTCCTCTAGAGATTCAAGACTTTTGGCGAGGCCATC
```

Figure 12 Continued

```
                        901                                                              950
Als1_ORF_Teal   ( 901)  CCGCCGCAATATGCTATCCAGGTACTGGATGAGCTGACAAAAGGGGAGGC
Als2_ORF_Teal   ( 901)  CCGCCGCAATATGCTATCCAGGTACTGGATGAGCTGACAAAAGGGGAGGC
Als3_ORF_Teal   ( 901)  CCGCCGCAATATGCTATCCAGGTACTGGATGAGCTGACAAAAGGGGAGGC
      Consensus  ( 901)  CCGCCGCAATATGCTATCCAGGTACTGGATGAGCTGACAAAAGGGGAGGC
                        951                                                             1000
Als1_ORF_Teal   ( 951)  GATCATTGCCACTGGTGTTGGGCAGCACCAGATGTGGCGGCTCAGTATT
Als2_ORF_Teal   ( 951)  GATCATTGCCACCGGTGTTGGGCAGCATCAGATGTGGCGGCTCAGTATT
Als3_ORF_Teal   ( 951)  GATCATTGCTACTGGTGTTGGGCAGCACCAGATGTGGCGGCTCAGTATT
      Consensus  ( 951)  GATCATTGCCACTGGTGTTGGGCAGCACCAGATGTGGCGGCTCAGTATT
                       1001                                                             1050
Als1_ORF_Teal   (1001)  ACACTTACAAGCGGCCACGGCAGTGGCTGTCTTCGTCTGTTTGGGGGCA
Als2_ORF_Teal   (1001)  ACACTTACAAGCGGCCACGGCAGTGGCTGTCTTCATCCGGTTTGGGTGCA
Als3_ORF_Teal   (1001)  ACACTTACAAGCGGCCACGGCAGTGGCTGTCTTCGTCTGTTTGGGGGCA
      Consensus  (1001)  ACACTTACAAGCGGCCACGGCAGTGGCTGTCTTCGTCTGTTTGGGGGCA
                       1051                                                             1100
Als1_ORF_Teal   (1051)  ATGGGATTTGGGTTGCCAGCTGCCAGCTGCAGCTGGCGCTGCTGGCCAACCCAGG
Als2_ORF_Teal   (1051)  ATGGGATTTGGGTTGCCAGCTGCCAGCTGCAGCTGGCGCTGCTGGCCAACCCAGG
Als3_ORF_Teal   (1051)  ATGGGATTTGGGTTACCAGCTGCAGCTGCAGCTGGCGCTGCTGGCCAACCCAGG
      Consensus  (1051)  ATGGGATTTGGGTTACCAGCTGCCAGCTGCAGCTGGCGCTGCTGGCCAACCCAGG
                       1101                                                             1150
Als1_ORF_Teal   (1101)  TGTTACAGTTGTTGTTGACATTGATGTGATGGTAGTTTCCTCATGAACATTC
Als2_ORF_Teal   (1101)  TGTTACAGTTGTTGTTGACATTGATGATGGGATGGTAGTTTCCTCATGAACATTC
Als3_ORF_Teal   (1101)  TGTTACAGTTGTTGTTGACATTGATGGAGATGGTAGTTTCCTCATGAACATTC
      Consensus  (1101)  TGTTACAGTTGTTGTTGACATTGATGG GATGGTAGTTTCCTCATGAACATTC
                       1151                                                             1200
Als1_ORF_Teal   (1151)  AGGAGTTGGCGTTGATCCGCATTGAGAACCTCCCAGTGAAGGTGATGATA
Als2_ORF_Teal   (1151)  AGGAGTTGGCGTTGATCCGTATTGAGAACCTCCAGTGAAGGTGATGATA
Als3_ORF_Teal   (1151)  AGGAGTTGGCATTGATCCGTATTGAGAACCTCCCTGTGAAGGTGATGATA
      Consensus  (1151)  AGGAGTTGGCGTTGATCCGTATTGAGAACCTCCCAGTGAAGGTGATGATA
```

Figure 12 Continued

```
            1250
       1201 TTGAACAACCAGCATCTGGGAATGGTGGTGCAGTGGGAGGATAGGTTTTA
Als1_ORF_Teal (1201) TTGAACAACCAGCATCTGGGAATGGTGGTGCAGTGGGAGGATAGGTTTTA
Als2_ORF_Teal (1201) TTGAACAACCAGCATCTGGGAATGGTGGTGCAGTGGGAGGATAGGTTTTA
Als3_ORF_Teal (1201) TTGAACAACCAGCATCTGGGAATGGTGGTGCAGTGGGAGGATAGGTTTTA
    Consensus (1201) TTGAACAACCAGCATCTGGGAATGGTGGTGCAGTGGGAGGATAGGTTTTA
            1300
       1251 CAAGGCCAATCGGGCGCACACATACCTTGGCAACCCAGAAAATGAGAGTG
Als1_ORF_Teal (1251) CAAGGCCAACCGGGCGCACACATACCTTGGCAACCCAGAAAATGAGAGTG
Als2_ORF_Teal (1251) CAAGGCCAATCGGGCGCACACATACCTTGGCAACCCAGAAAATGAGAGTG
Als3_ORF_Teal (1251) CAAGGCCAATCGGGCGCACACATACCTTGGCAACCCAGAAAATGAGAGTG
    Consensus (1251) CAAGGCCAATCGGGCGCACACATACCTTGGCAACCCAGAAAATGAGAGTG
            1350
       1301 AGATATATCCAGATTTTGTGACGATTGCTAAAGGATTCAACGTTCCAGCA
Als1_ORF_Teal (1301) AGATATATCCAGATTTTGTGACGATTGCTAAAGGATTCAACGTTCCGGCA
Als2_ORF_Teal (1301) AGATATATCCAGATTTTGTGACGATTGCTAAAGGATTCAACGTTCCGGCA
Als3_ORF_Teal (1301) AGATATATCCAGATTTTGTGACGATTGCTAAAGGATTCAACGTTCCGGCA
    Consensus (1301) AGATATATCCAGATTTTGTGACGATTGCTAAAGGATTCAACGTTCCGGCA
            1400
       1351 GTTCGTGTGACGAAGAAGAGCGAAGTCACTGCAGCAATCAAGAAGATGCT
Als1_ORF_Teal (1351) GTTCGTGTGACGAAGAAGAGAGCGAAGTCACTGCAGCAATCAAGAAGATGCT
Als2_ORF_Teal (1351) GTTCGTGTGACGAAGAAGAGAGCGAAGTCACTGCAGCAATCAAGAAGATGCT
Als3_ORF_Teal (1351) GTTCGTGTGACGAAGAAGAGAGCGAAGTCACTGCAGCAATCAAGAAGATGCT
    Consensus (1351) GTTCGTGTGACGAAGAAGAGAGCGAAGTCACTGCAGCAATCAAGAAGATGCT
            1450
       1401 TGAGACCCCAGGGCCATACTTGTTGGATATCATTGTCCCGCATCAGGAGC
Als1_ORF_Teal (1401) TGAGACCCCAGGGCCATACTTGTTGGATATCATTGTCCCGCATCAGGAGC
Als2_ORF_Teal (1401) TGAGACCCCAGGGCCATACTTGTTGGATATCATTGTCCCGCATCAGGAGC
Als3_ORF_Teal (1401) TGAGACCCCAGGGCCATACTTGTTGGATATCAT GTCCCGCATCAGGAGC
    Consensus (1401) TGAGACCCCAGGGCCATACTTGTTGGATATCATTGTCCCGCATCAGGAGC
            1500
       1451 ACGTGCTGCCTATGATCCCAAGCGGTGGTGCTTTCAAGGACATGATCATG
Als1_ORF_Teal (1451) ACGTGCTGCCTATGATCCCAAGCGGTGGTGCTTTTAAGGACATGATCATG
Als2_ORF_Teal (1451) ACGTGCTGCCTATGATCCCAAGCGGTGGTGCTTTCAAGGACATGATCATG
Als3_ORF_Teal (1451) ACGTGCTGCCTATGATCCCAAGCGGTGGTGCTTTCAAGGACATGATCATG
    Consensus (1451) ACGTGCTGCCTATGATCCCAAGCGGTGGTGCTTTCAAGGACATGATCATG
```

Figure 12 Continued

```
                    1501                         1524
Als1_ORF_Teal  (1501) GAGGGTGATGGCAGGAGGACCTCGTAC
Als2_ORF_Teal  (1501) GAGGGTGATGGCAGGAGGACCTCGTAC
Als3_ORF_Teal  (1501) GAGGGTGATGGCAGGAGGACCTCGTAC
Consensus      (1501) GAGGGTGATGGCAGGAGGACCTCGTAC
```

WHEAT PLANTS HAVING INCREASED RESISTANCE TO IMIDAZOLINONE HERBICIDES

CROSS-REFERENCE TO RELATED APPLICATIONS

This application is the U.S. National Stage of International Application No. PCT/CA02/01051, filed Jul. 10, 2002, which published in English on Feb. 20, 2003 and designates the U.S., and which claims the priority benefit of U.S. Provisional Application Ser. No. 60/311,282 filed Aug. 9, 2001.

FIELD OF THE INVENTION

The present invention relates in general to plants having an increased resistance to imidazolinone herbicides. More specifically, the present invention relates to wheat plants obtained by mutagenesis and cross-breeding and transformation that have an increased resistance to imidazolinone herbicides.

BACKGROUND OF THE INVENTION

Acetohydroxyacid synthase (AHAS; EC 4.1.3.18) is the first enzyme that catalyzes the biochemical synthesis of the branched chain amino acids valine, leucine and isoleucine (Singh B. K., 1999 Biosynthesis of valine, leucine and isoleucine in: Singh B. K. (Ed) Plant amino acids. Marcel Dekker Inc. New York, N.Y. Pg 227-247). AHAS is the site of action of four structurally diverse herbicide families including the sulfonylureas (LaRossa R A and Falco S C, 1984 Trends Biotechnol 2:158-161), the imidazolinones (Shaner et al., 1984 Plant Physiol 76:545-546), the triazolopyrimidines (Subramanian and Gerwick, 1989 Inhibition of acetolactate synthase by triazolopyrimidines in (ed) Whitaker J R, Sonnet P E Biocatalysis in agricultural biotechnology. ACS Symposium Series, American Chemical Society. Washington, D.C. Pg 277-288), and the pyrimidyloxybenzoates (Subramanian et al., 1990 Plant Physiol 94: 239-244.). Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfiron, primisulfiron methyl, cinosulfuron, amidosulifiron, fluzasulfuron, imazosuifiron, pyrazosulfuiron ethyl and halosulfuron.

Due to their high effectiveness and low-toxicity, imidazolinone herbicides are favored for application by spraying over the top of a wide area of vegetation. The ability to spray an herbicide over the top of a wide range of vegetation decreases the costs associated with plantation establishment and maintenance and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone resistant species of the desired vegetation in the spray over area.

Among the major agricultural crops, some leguminous species such as soybean are naturally resistant to imidazolinone herbicides due to their ability to rapidly metabolize the herbicide compounds (Shaner and Robinson, 1985 Weed Sci. 33:469-471). Other crops such as corn (Newhouse et al., 1992 Plant Physiol. 100:882-886) and rice (Barrette et al., 1989 Crop Safeners for Herbicides, Academic Press New York, pp. 195-220) are somewhat susceptible to imidazolinone herbicides. The differential sensitivity to the imidazolinone herbicides is dependent on the chemical nature of the particular herbicide and differential metabolism of the compound from a toxic to a non-toxic form in each plant (Shaner et at., 1984 Plant Physiol. 76:545-546; Brown et al., 1987 Pestic. Biochm. Physiol. 27:24-29). Other plant physiological differences such as absorption and translocation also play an important role in sensitivity (Shaner and Robinson, 1985 Weed Sci. 33:469-471).

Crop cultivars resistant to imidazolinones, sulfonylureas and triazolopyrimidines have been successfully produced using seed, microspore, pollen, and callus mutagenesis in *Zea mays, Arabidopsis thaliana, Brassica napus, Glycine max*, and *Nicotiana tabacum* (Sebastian et al., 1989 Crop Sci. 29:1403-1408; Swanson et al., 1989 Theor. Appl. Genet. 78:525-530; Newhouse et al., 1991 Theor. Appl. Genet. 83:65-70; Sathasivan et al., 1991 Plant Physiol. 97:1044-1050; Mourand et al., 1993 J. Heredity 84: 91-96). In all cases, a single, partially dominant nuclear gene conferred resistance. Four imidazolinone resistant wheat plants were also previously isolated following seed mutagenesis of *Triticum aestivum* L. cv Fidel (Newhouse et al., 1992 Plant Physiol. 100:882-886). Inheritance studies confirmed that a single, partially dominant gene conferred resistance. Based on allelic studies, the authors concluded that the mutations in the four identified lines were located at the same locus. One of the Fidel cultivar resistance genes was designated FS-4 (Newhouse et al., 1992 Plant Physiol. 100:882-886).

Computer-based modeling of the three dimensional conformation of the AHAS-inhibitor complex predicts several amino acids in the proposed inhibitor binding pocket as sites where induced mutations would likely confer selective resistance to imidazolinones (Ott et al., 1996 J. Mol. Biol. 263: 359-368) Wheat plants produced with some of these rationally designed mutations in the proposed binding sites of the AHAS enzyme have in fact exhibited specific resistance to a single class of herbicides (Ott et al., 1996 J. Mol. Biol. 263: 359-368).

Plant resistance to imidazolinone herbicides has also been reported in a number of patents. U.S. Pat. Nos. 4,761,373, 5,331,107, 5,304,732, 6,211,438, 6,211,439 and 6,222,100 generally describe the use of an altered AHAS gene to elicit herbicide resistance in plants, and specifically discloses certain imidazolinone resistant corn lines. U.S. Pat. No. 5,013, 659 discloses plants exhibiting herbicide resistance possessing mutations in at least one amino acid in one or more conserved regions. The mutations described therein encode either cross-resistance for imidazolinones and sulfonylureas or sulfonylurea-specific resistance, but imidazolinone-specific resistance is not described. Additionally, U.S. Pat. Nos. 5,731,180 and 5,767,361 discuss an isolated gene having a single amino acid substitution in a wild-type monocot AHAS amino acid sequence that results in imidazolinone-specific resistance.

To date, the prior art has not described imidazolinone resistant wheat plants containing more than one altered AHAS gene. Nor has the prior art described imidazolinone resistant wheat plants containing mutations on genomes other than the genome from which the FS-4 gene is derived. Therefore, what is needed in the art is the identification of imidazolinone resistance genes from additional genomes. What are also needed in the art are wheat plants having increased resistance to herbicides such as imidazolinone and containing more than one altered AHAS gene. Also needed are methods for controlling weed growth in the vicinity of such wheat plants. These compositions and methods would allow for the use of spray over techniques when applying herbicides to areas containing wheat plants.

SUMMARY OF THE INVENTION

The present invention provides wheat plants comprising IMI nucleic acids, wherein the wheat plant has increased resistance to an imidazolinone herbicide as compared to a wild-type variety of the plant. The wheat plants can contain one, two, three or more IMI nucleic acids. In one embodiment, the wheat plant comprises multiple IMI nucleic acids located on different genomes. Preferably, the IMI nucleic acids encode proteins comprising a mutation in a conserved amino acid sequence selected from the group consisting of a Domain A, a Domain B, a Domain C, a Domain D and a Domain E. More preferably, the mutation is in a conserved Domain E or a conserved Domain C. Also provided are plant parts and plant seeds derived from the wheat plants described herein. In another embodiment, the wheat plant comprises an IMI nucleic acid that is not an IMI nucleic acid. The IMI nucleic acid can be an Imi2 or Imi3 nucleic acid, for example.

The IMI nucleic acids of the present invention can comprise a nucleotide sequence selected from the group consisting of: a polynucleotide of SEQ ID NO:1; a polynucleotide of SEQ ID NO:3; a polynucleotide sequence encoding a polypeptide of SEQ ID NO:2; a polynucleotide sequence encoding a polypeptide of SEQ ID NO:4, a polynucleotide comprising at least 60 consecutive nucleotides of any of the aforementioned polynucleotides; and a polynucleotide complementary to any of the aforementioned polynucleotides.

The plants of the present invention can be transgenic or non-transgenic. Examples of non-transgenic wheat plants having increased resistance to imidazolinone herbicides include a wheat plant having an ATCC Patent Deposit Designation Number PTA-3953 or PTA-3955; or a mutant, recombinant, or genetically engineered derivative of the plant with ATCC Patent Deposit Designation Number PTA-3953 or PTA-3955; or of any progeny of the plant with ATCC Patent Deposit Designation Number PTA-3953 or PTA-3955; or a plant that is a progeny of any of these plants.

In addition to the compositions of the present invention, several methods are provided. Described herein are methods of modifying a plant's tolerance to an imidazolinone herbicide comprising modifying the expression of an IMI nucleic acid in the plant. Also described are methods of producing a transgenic plant having increased tolerance to an imidazolinone herbicide comprising, transforming a plant cell with an expression vector comprising one or more IMI nucleic acids and generating the plant from the plant cell. The invention further includes a method of controlling weeds within the vicinity of a wheat plant, comprising applying an imidazolinone herbicide to the weeds and to the wheat plant, wherein the wheat plant has increased resistance to the imidazolinone herbicide as compared to a wild type variety of the wheat plant and wherein the plant comprises one or more IMI nucleic acids. In some preferred embodiments of these methods, the plants comprise multiple IMI nucleic acids that are located on different wheat genomes.

BRIEF DESCRIPTION OF THE DRAWINGS

FIG. 1 is a table showing the results of single plant evaluation of imazamox resistance in parental and $F_1$ populations resulting from reciprocal crosses between resistant lines and CDC Teal. The numbers presented represent the number of plants scored into each phenotypic class. Parental lines are indicated in bold. The number of parental lines scored include those scored with the $F_2$ populations.

FIG. 2 is a table showing the reaction to imazamox in $F_2$ and $BCF_1$ populations resulting from crosses between resistant lines and CDC Teal and Chi-square tests of single locus and two locus models (15A×Teal) for control of resistance. The symbols used in FIG. 2 indicate the following: a—Chi-square P value (1 df) represents the probability that deviations from the tested ratio are due to chance alone. Chi-square P values greater than 0.05 indicate that observed values were not significantly different from expected values; b—Chi-square P value representing the probability that deviations between $F_2$ populations resulting from reciprocal crosses between CDC Teal and resistant lines are due to chance alone. Chi-square values greater than 0.05 indicate that reciprocal $F_2$ populations were homogeneous, and data from the two reciprocal populations was pooled; c—CDC Teal was used as the recurrent parent; d—Ratios tested were based on the results of the $F_2$ generation; and e—Chi-square P value (1 df) for $BCF_1$ ratio.

FIG. 3 is a table showing the results of an evaluation of resistance to imazamox in $F_{2:3}$ families resulting from crosses between resistant lines and CDC Teal and Chi-square tests of single-locus and two locus models (15A×Teal) for control of resistance. The symbols used in FIG. 3 indicate the following: a—Family segregation ratios tested were based on the results of the $F_2$ and $BCF_1$ populations; b—Chi-square P value (2 df) representing the probability that deviations from the tested ratio are due to chance alone. Chi-square P values greater than 0.05 indicate that observed values were not significantly different from expected values.

FIG. 4 is a table showing the results of a single plant evaluation of imazaamox resistance in $F_2$ populations resulting from inter-crosses between resistant lines. Chi-square ratios tested were based on the results of the $F_2$ and $F_{2:3}$ family results obtained from crosses between resistant lines and CDC Teal. The 15:1 ratio tested is for a two locus model and the 63:1 ratio tested is for a three locus model. The "a" symbol used in FIG. 4 indicates the following: Chi-square P value (1 df) representing the probability that deviations from the tested ratio are due to chance alone. Chi-square P values greater than 0.05 indicate that observed values were not significantly different from expected values.

FIG. 5 is a table showing the results of an evaluation of imazamox resistance in $F_{2:3}$ families resulting from segregating inter-crosses between resistant lines. The symbols used in FIG. 5 indicate the following: a—Family segregation ratios tested were based on the results of the $F_2$ populations examined; b—Chi-square P value (2 df) representing the probability that deviations from the tested ratio are due to chance alone. Chi-square P values greater than 0.05 indicate that observed values were not significantly different from expected values.

FIG. 6 is a table comparing the percent uninhibited in vitro AHAS activity in four wheat lines in the presence of increasing concentrations of the imidazolinone herbicide imazamox.

Teal is a wild type line with no tolerance to imidazolinone herbicides while BW755 contains the FS4 mutant gene.

FIG. 7 is a table comparing injury sustained by three wheat genotypes when treated with either a 10× or 30× rate of imazamox. The 1× rate is 20 g/ha. BW755 contains the FS4 mutant gene. 15A/11A is a bulk of selfed progeny from the cross of Teal11A and Teal15A. The population was not yet homozygous at all three non-allelic loci.

Figure 8:
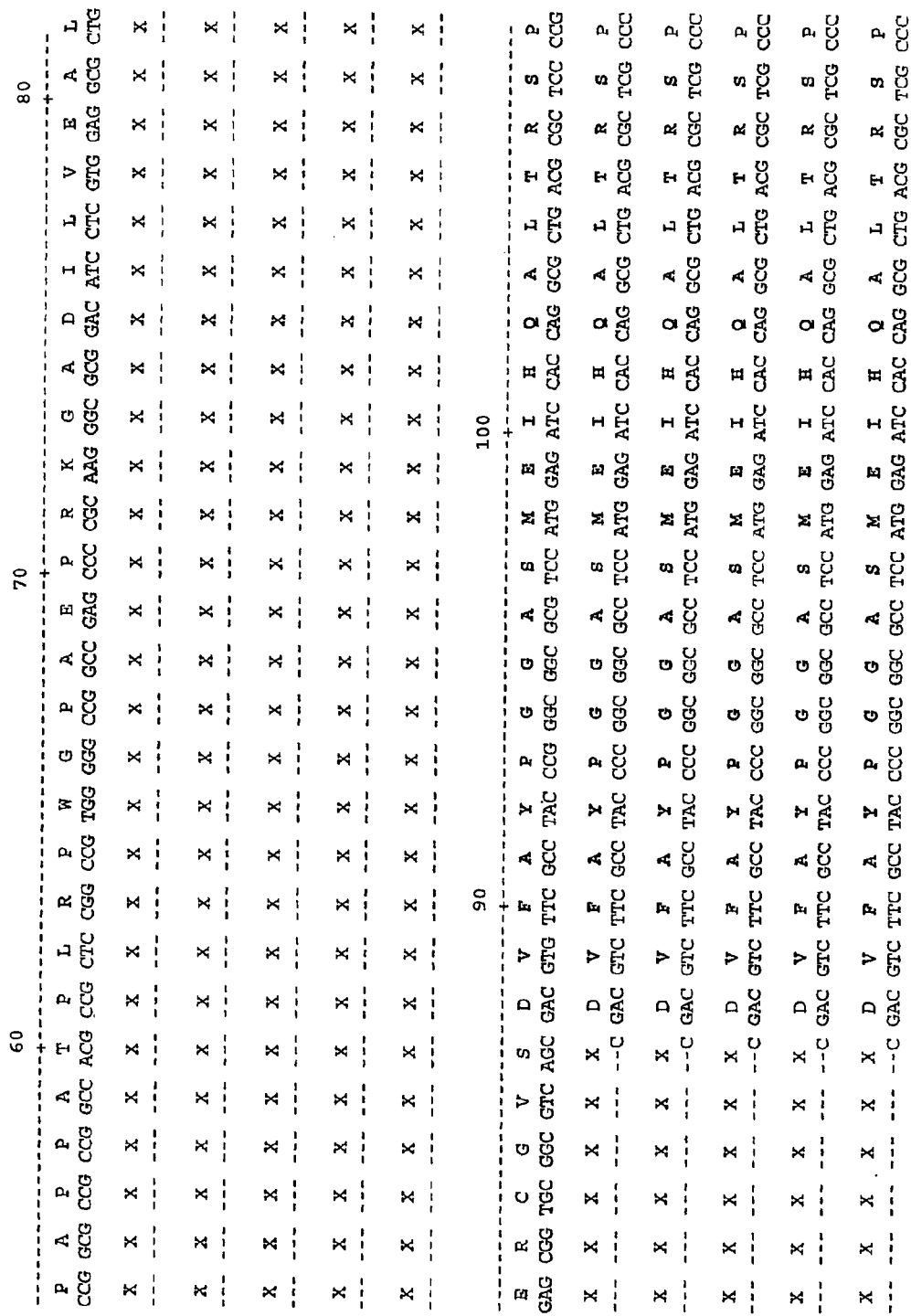

FIG. 8 shows a DNA sequence alignment of partial Als1 and Imi1 wheat genes amplified from genomic DNA: CDC Teal (row 2; SEQ ID NO:15 and SEQ ID NO:16), BW755 (row 3; SEQ ID NO:17 and SEQ ID NO:18), TealIMI 10A (row 4; SEQ ID NO:19 and SEQ ID NO:20), TealIMI 11A (row 5; SEQ ID NO:21 and SEQ ID NO:22), and TealIMI 15A (row 6; SEQ ID NO:23 and SEQ ID NO:24). Partial sequences were aligned with a complete rice ALS gene sequence (row 1; SEQ ID NO:13 and SEQ ID NO:14) derived from Genbank (Accession no. ABO49822) and translated to protein sequences (presented on top of the DNA sequences). The five highly conserved amino acid domains known to house mutations that confer resistance to AHAS inhibitors are indicated in bold. Note the guanine to adenine substitutions in BW755, TealIMI 10A, and TealIMI 15A result in a serine to asparagine substitution (serine627 in rice) in the IPSGG domain (Domain E) of the Als1 gene. Accordingly, the resistance genes present in the BW755, TealIMI 10A, and TealIMI 15A plants have been designated as part of the Imi1 class. These Teal resistance genes are referred to herein as TealIMI1 10A and TealIMI1 15A.

Figure 9:
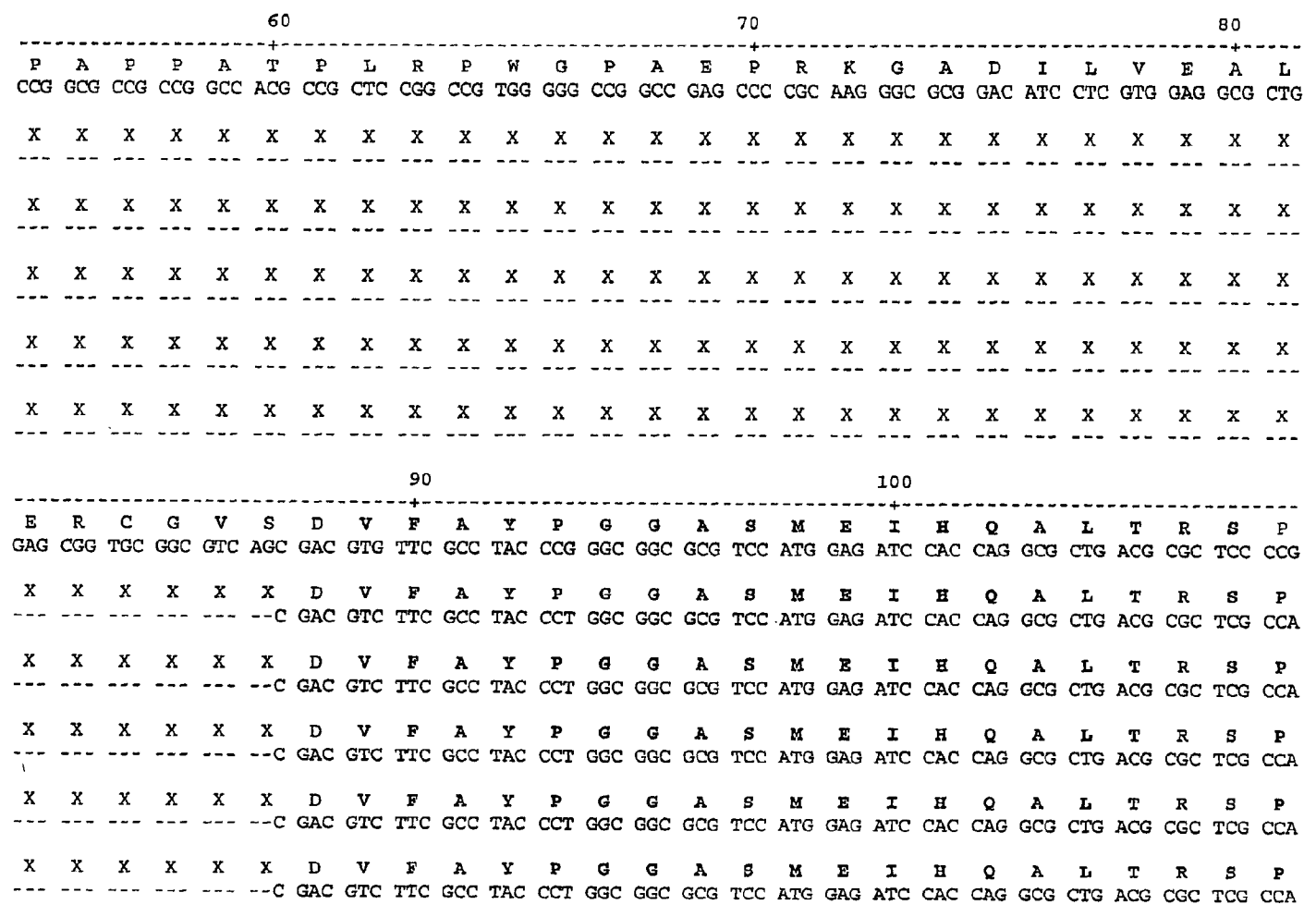
Figure 9:
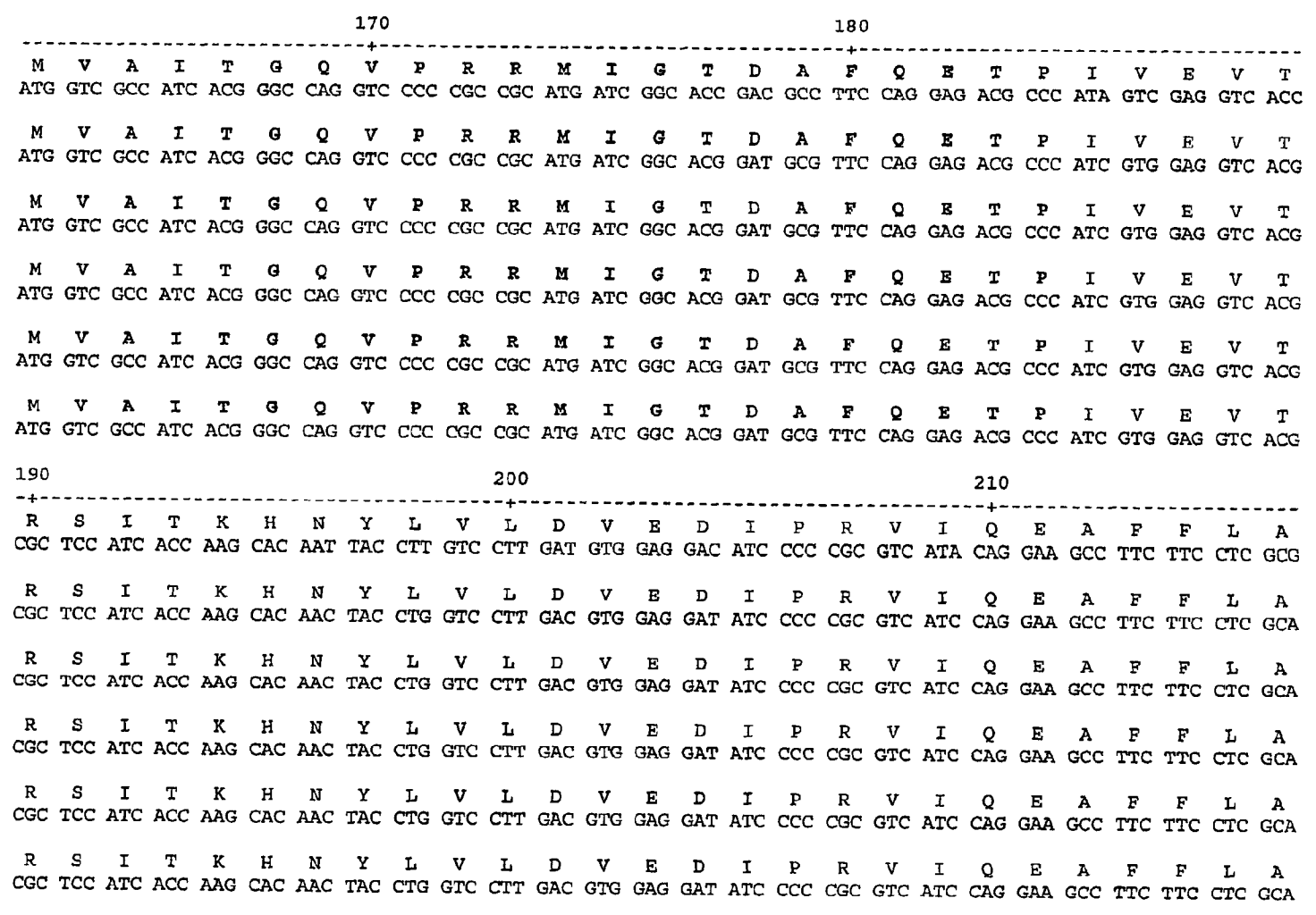
Figure 9:
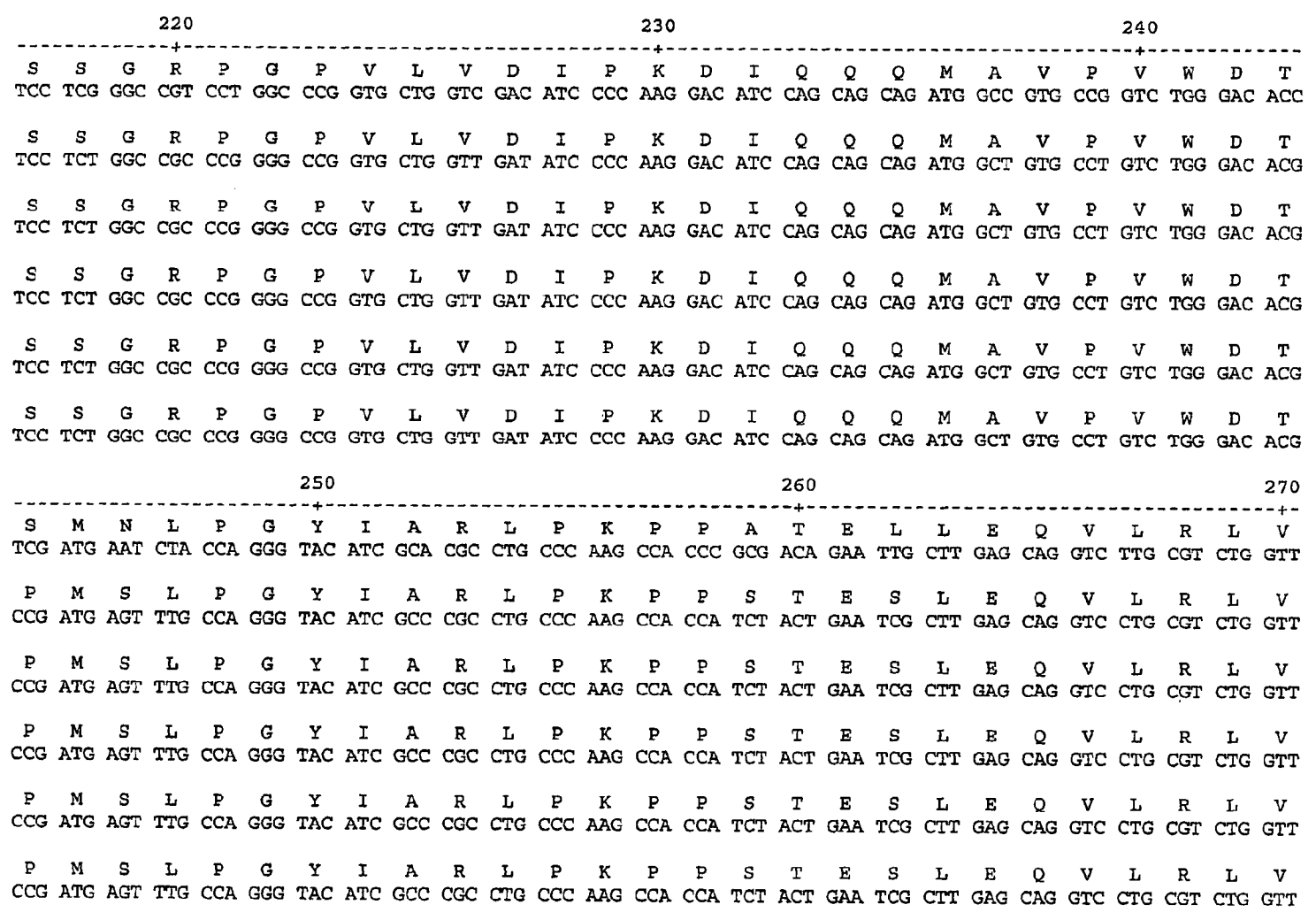
Figure 9:
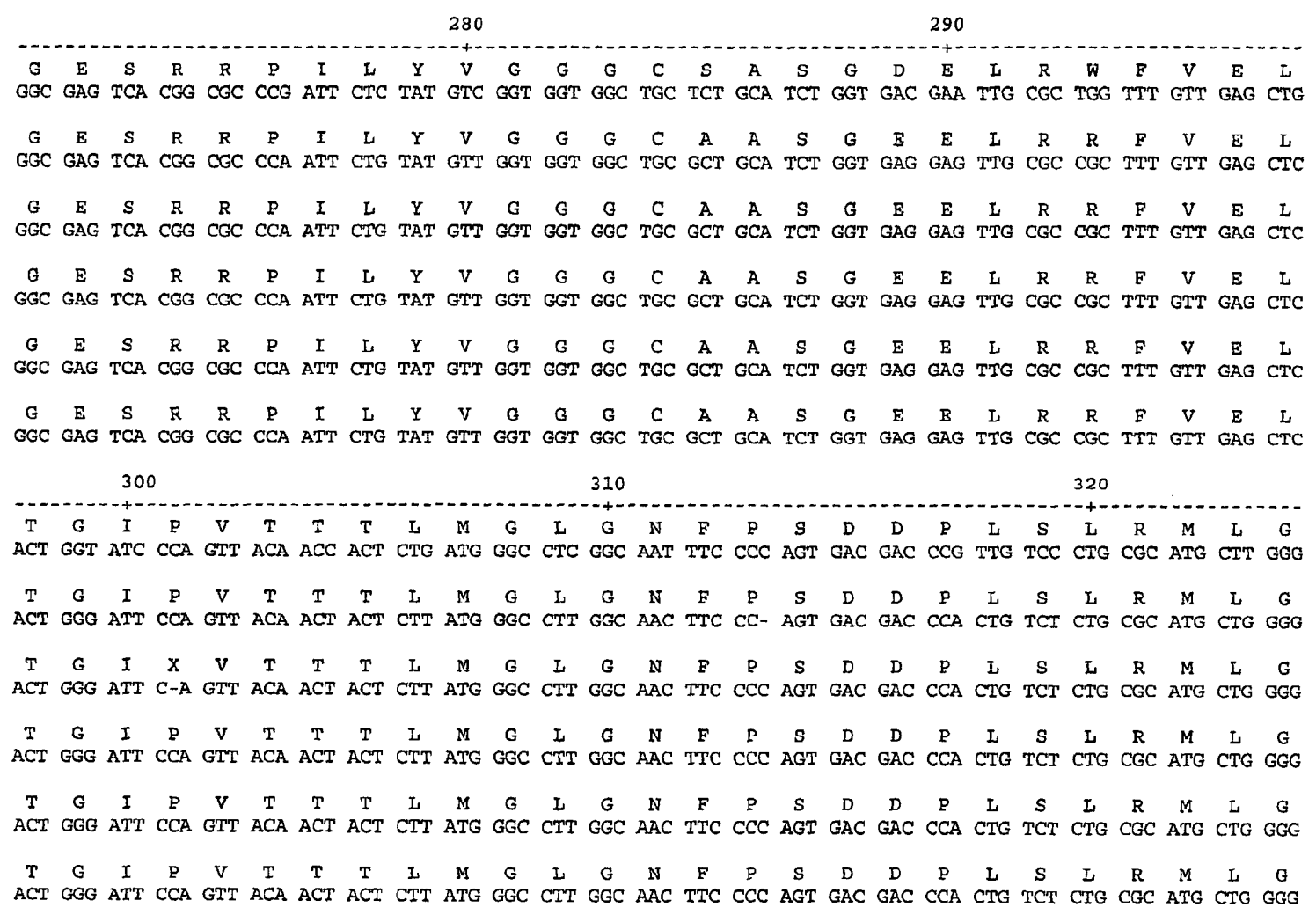
Figure 9:
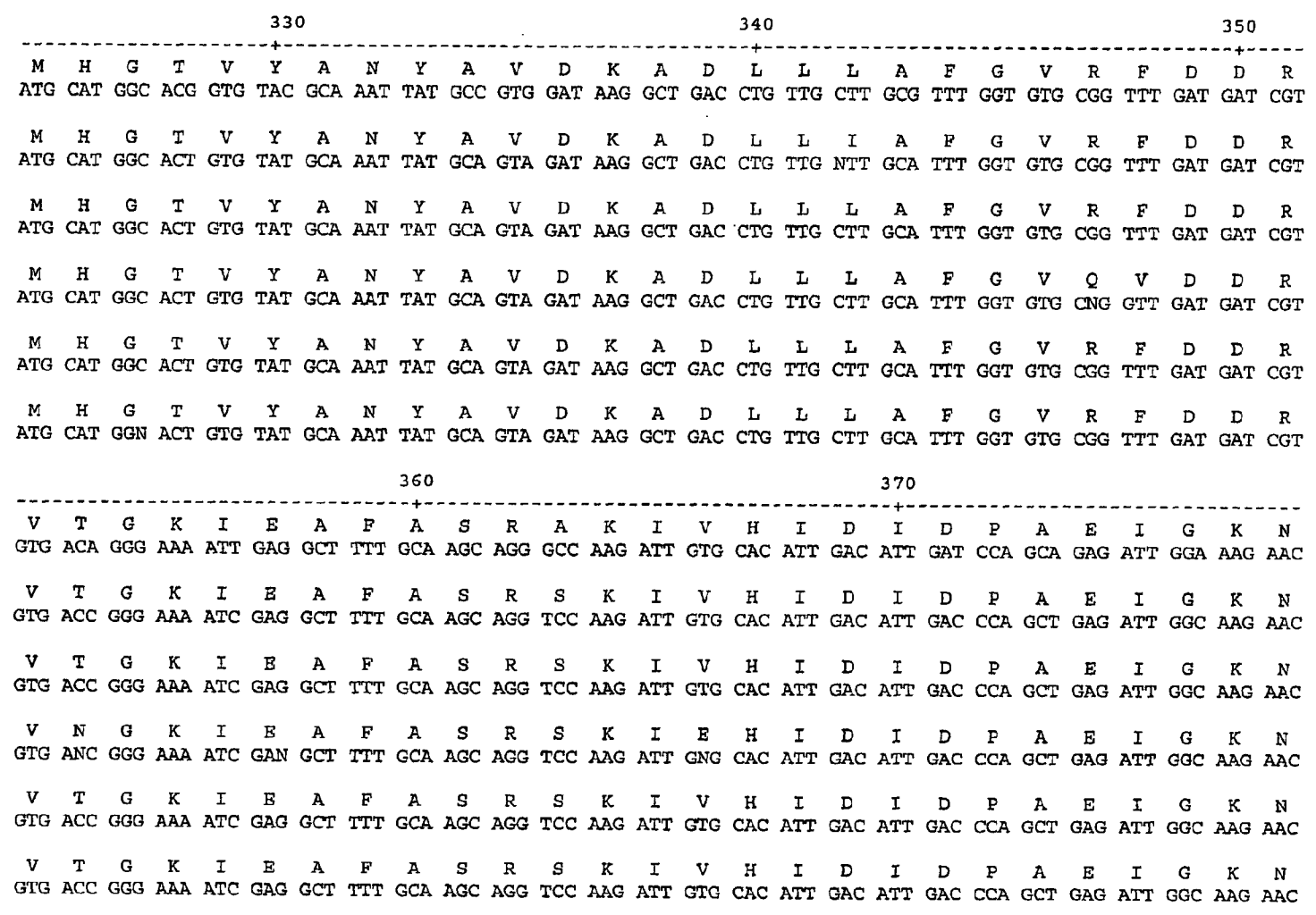
Figure 9:
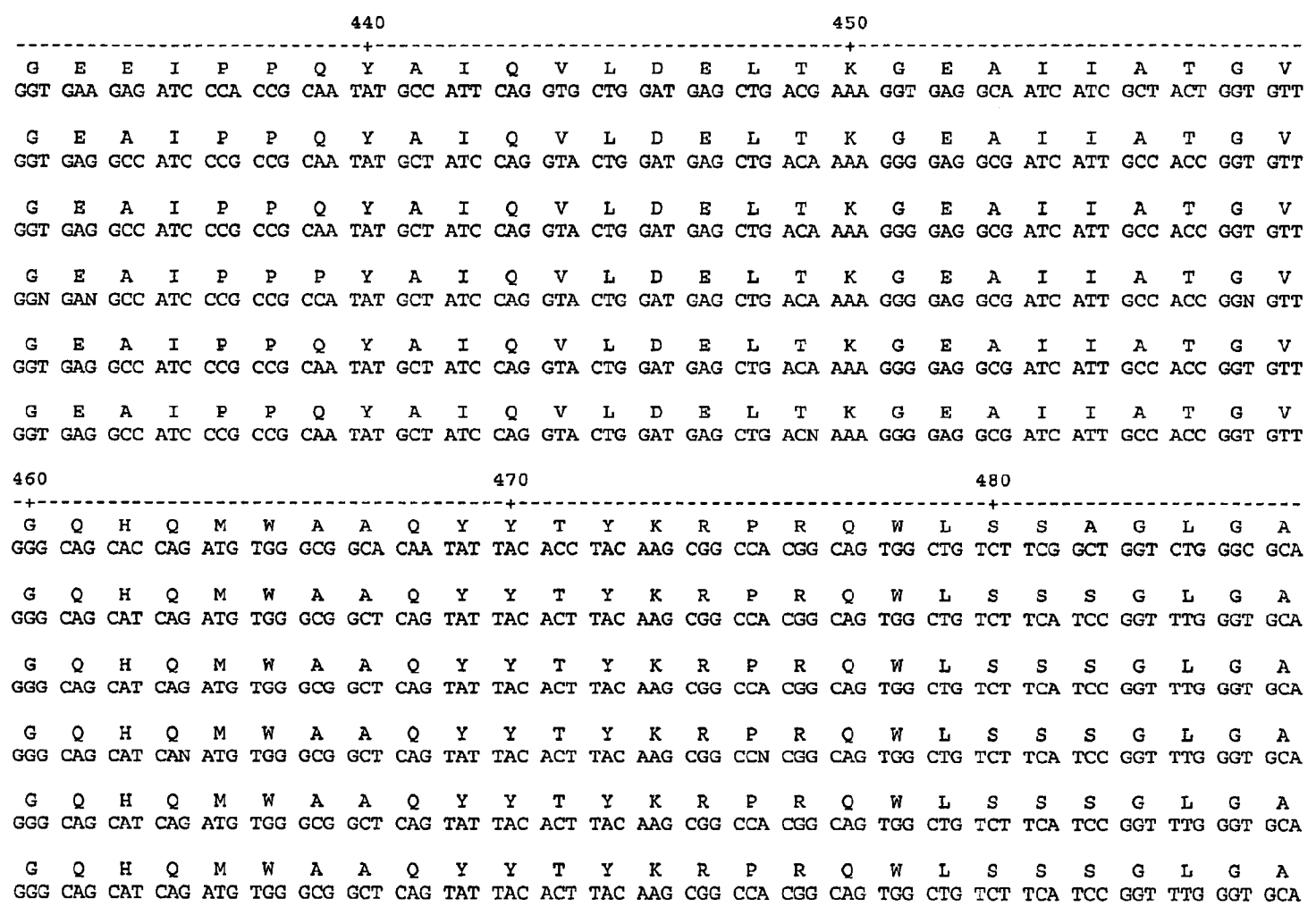
Figure 9:
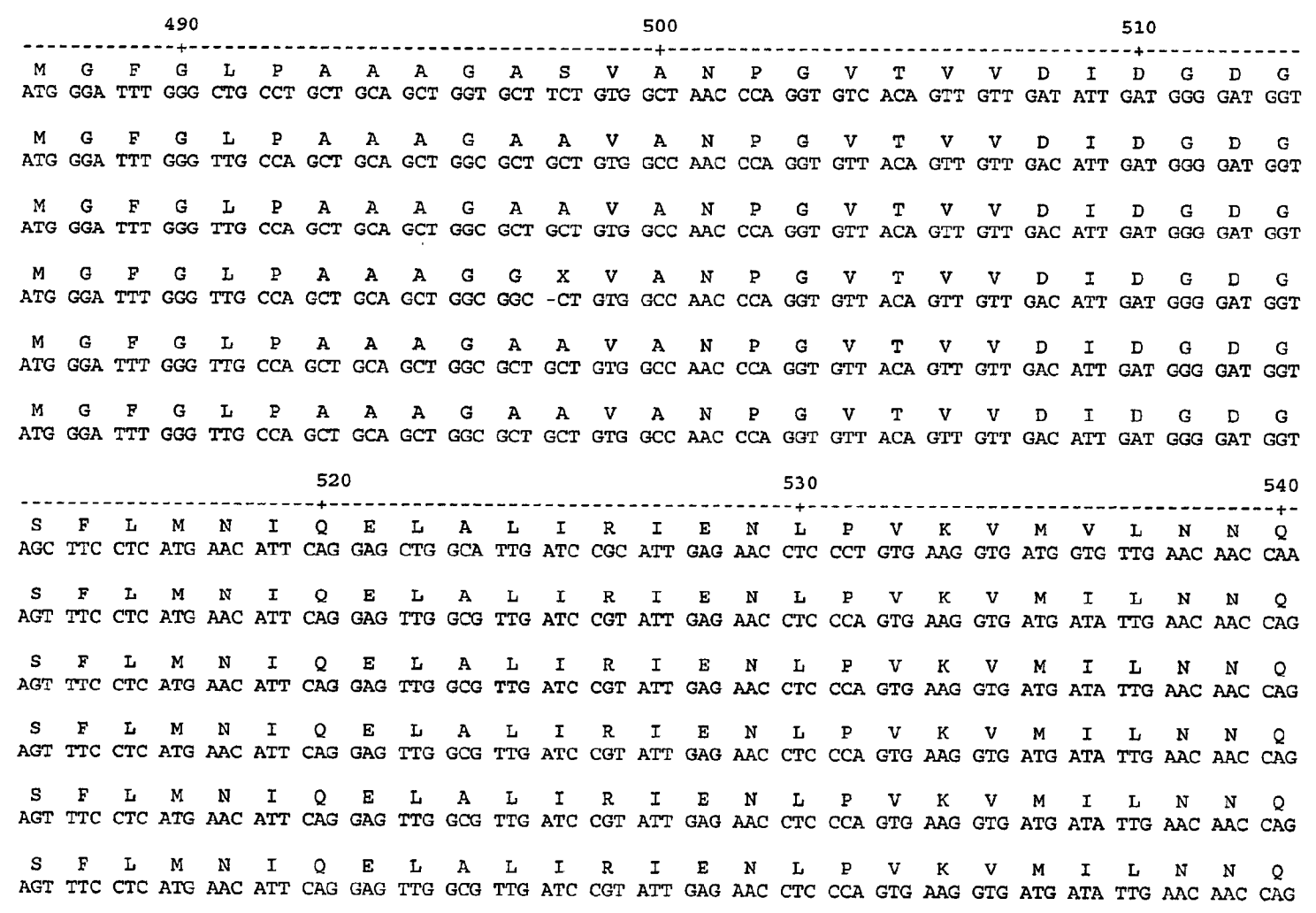
Figure 9:
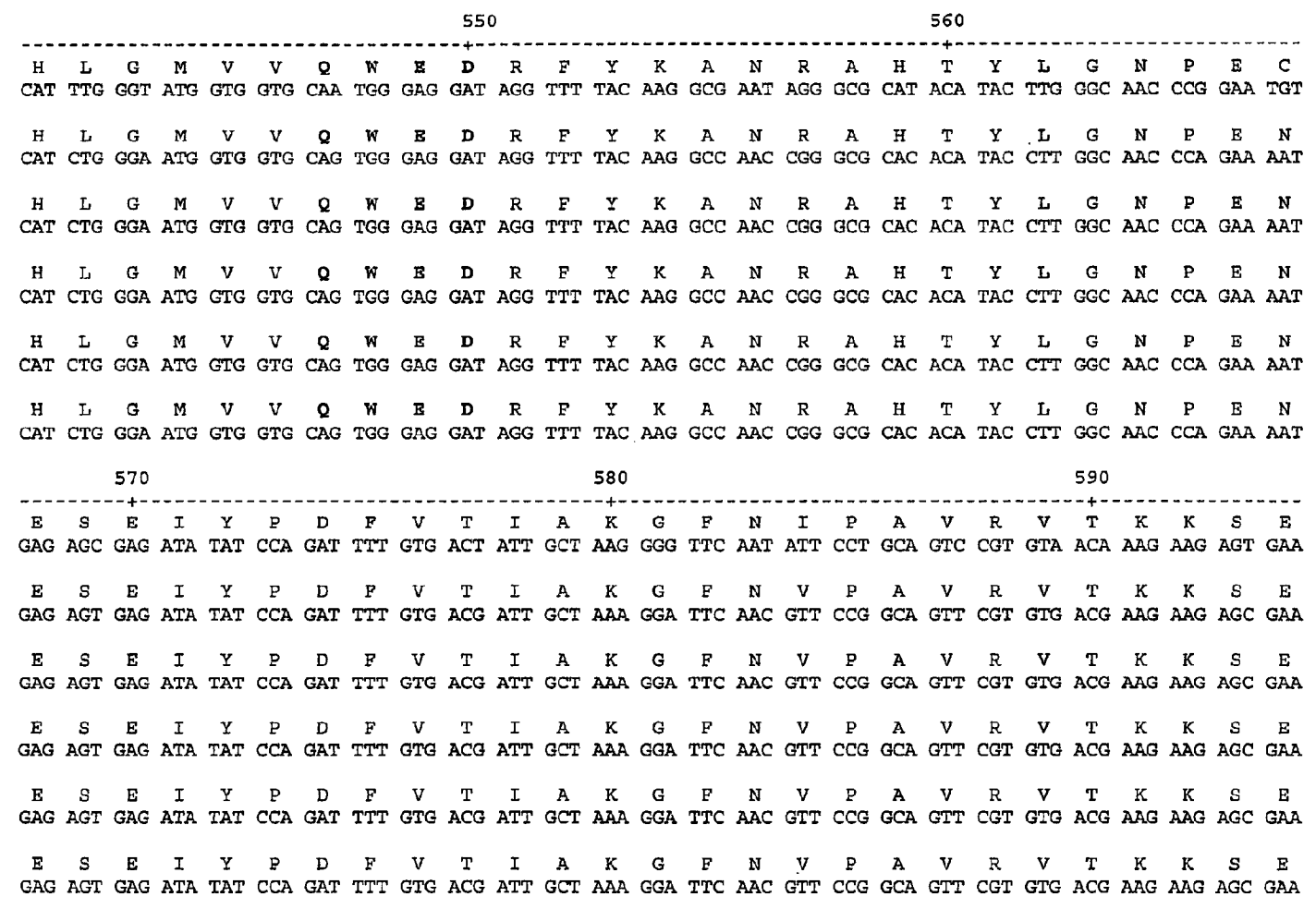

FIG. 9 shows a DNA sequence alignment of partial Als2 and Imi2 wheat genes amplified from genomic DNA: CDC Teal (row 2; SEQ ED NO: 25 and SEQ ID NO:26), BW755 (row 3; SEQ ID NO:27 and SEQ ID NO:28), TealIMI 10A (row 4; SEQ ID NO:29 and SEQ ID NO:30), TealIMI 11A (row 5; SEQ ID NO:31 and SEQ ID NO:32) and TealIMI 15A (row 6; SEQ ID NO:33 and SEQ ID NO:34). Partial AHAS sequences were aligned with a complete rice AHAS sequence (row 1; SEQ ID NO:13 and SEQ ID NO:14) derived from GenBank (Accession no. AB049822) and translated into protein sequences (presented above the DNA sequences). The five highly conserved domains known to house mutations that confer resistance to AHAS inhibitors are indicated in bold. Note the guanine to adenine substitution in TealIMI 11A, resulting in a serine to asparagine substitution (serine627 in rice) in the IPSGG domain of the Als2 gene. Accordingly, the resistance gene present in TealIMI 11A plant has been designated as part of the Imi2 class of nucleic acids. This Teal resistance gene is referred to herein as TealIMI2 11A.

FIG. 10 shows the partial DNA sequence of TealIMI1 15A (SEQ ID NO:1) and the deduced amino acid sequence of the same (SEQ ID NO:2).

FIG. 11 shows the partial DNA sequence of TealIMI2 11A (SEQ ID NO:3) and the deduced amino acid sequence of the same (SEQ ID NO:4).

FIG. 12 shows the wild type nucleic acid sequence of the Teal ALS1 ORF (SEQ ID NO:5), the Teal ALS2 ORF (SEQ ID NO:6) the Teal ALS3 ORF (SEQ ID NO:7).

Figure 13:
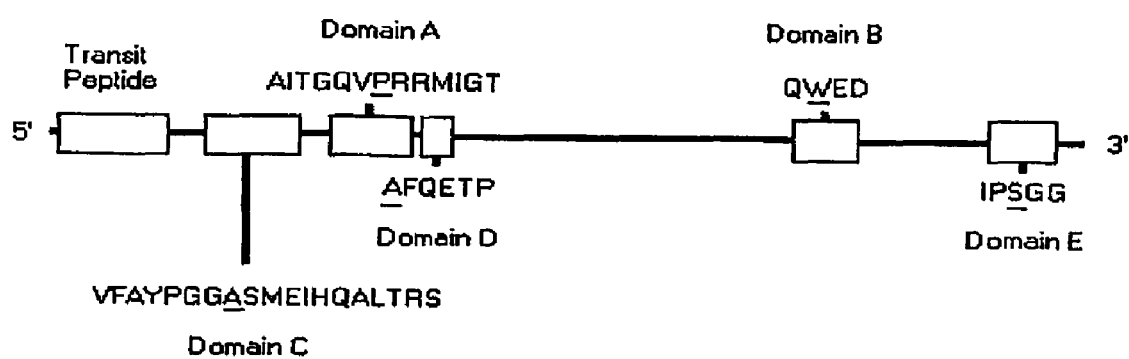

FIG. 13 is a schematic representation of the conserved amino acid sequences in the AHAS genes implicated in resistance to various AHAS inhibitors. The specific amino acid site responsible for resistance is indicated by an underline. (Modified from Devine, M. D. and Eberlein, C. V., 1997 Physiological, biochemical and molecular aspects of herbicide resistance based on altered target sites in Herbicide Activity: Toxicity, Biochemistry, and Molecular Biology, IOS Press Amsterdam, p. 159-185).

DETAILED DESCRIPTION

The present invention is directed to wheat plants, wheat plant parts and wheat plant cells having increased resistance to imidazolinone herbicides. The present invention also includes seeds produced by the wheat plants described herein and methods for controlling weeds in the vicinity of the wheat plants described herein. It is to be understood that as used in the specification and in the claims, "a" or "an" can mean one or more, depending upon the context in which it is used. Thus, for example, reference to "a cell" can mean that at least one cell can be utilized.

As used herein, the term "wheat plant" refers to a plant that is a member of the *Triticum* genus. The wheat plants of the present invention can be members of a *Triticum* genus including, but not limited to, *T. aestivum, T. turgidum, T. timopheevii, T. monococcum, T. zhukovskyi* and *T. urartu* and hybrids thereof. Examples of *T. aestivum* subspecies included within the present invention are *aestivum* (common wheat), *compactum* (club wheat), *macha* (macha wheat), *vavilovi* (vavilovi wheat), *spelta* and *sphaerococcum* (shot wheat). Examples of *T. turgidum* subspecies included within the present invention are *turgidum, carthlicum, dicoccon, durum, paleocolchicumt, polonicum, turanicum* and *dicoccoides*. Examples of *T. monococcum* subspecies included within the present invention are *monococcum* (einkorn) and *aegilopoides*. In one embodiment of the present invention, the wheat plant is a member of the *Triticum aestivum* species, and more particularly, the CDC Teal cultivar.

The term "wheat plant" is intended to encompass wheat plants at any stage of maturity or development as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts and the like. The present invention also includes seeds produced by the wheat plants of the present invention. In one embodiment, the seeds are true breeding for an increased resistance to an imidazolinone herbicide as compared to a wild type variety of the wheat plant seed.

The present invention describes a wheat plant comprising one or more IMI nucleic acids, wherein the wheat plant has increased resistance to an imidazolinone herbicide as compared to a wild-type variety of the plant. As used herein, the term "IMI nucleic acid" refers to a nucleic acid that is mutated from an AHAS nucleic acid in a wild type wheat plant that confers increased imidazolinone resistance to a plant in which it is transcribed. Wild type Teal AHAS nucleic acids are shown in SEQ ID NO:5 (Teal ALS1 ORF), SEQ ED NO:6 (Teal ALS2 ORF) and SEQ ID NO:7 (Teal ALS3 ORF). In one embodiment, the wheat plant comprises multiple IMI nucleic acids. As used when describing the IMI nucleic acids, the term "multiple" refers to IMI nucleic acids that have different nucleotide sequences and does not refer to a mere increase in number of the same IMI nucleic acid. For example, the IMI nucleic acids can be different due to the fact that they are derived from or located on different wheat genomes.

It is possible for the wheat plants of the present invention to have multiple IMI nucleic acids from different genomes since these plants can contain more than one genome. For example, a *Triticum aestivum* wheat plant contains three genomes sometimes referred to as the A, B and D genomes. Because AHAS is a required metabolic enzyme, it is assumed that each genome has at least one gene coding for the AHAS enzyme, commonly seen with other metabolic enzymes in hexaploid wheat that have been mapped. The AHAS nucleic acid on each genome can, and usually does, differ in its nucleotide sequence from an AHAS nucleic acid on another genome. One of skill in the art can determine the genome of origin of each AHAS nucleic acid through genetic crossing and/or either sequencing methods or exonuclease digestion methods known to those of skill in the art and as also described in Example 2 below. For the purposes of this invention, IMI nucleic acids derived from one of the A, B or D genomes are distinguished and designated as Imi1, Imi2 or Imi3 nucleic acids.

It is not stated herein that any particular Imi nucleic acid class correlates with any particular A, B or D genome. For example, it is not stated herein that the Imi1 nucleic acids correlate to A genome nucleic acids, that Imi2 nucleic acids correlate to B genome nucleic acids, etc. The Imi1, Imi2 and Imi3 designations merely indicate that the IMI nucleic acids within each such class do not segregate independently, whereas two M nucleic acids from different classes do segregate independently and may therefore be derived from different wheat genomes. The Imi1 class of nucleic acids includes the FS-4 gene as described by Newhouse et al. (1992 Plant Physiol. 100:882-886) and the TealIMI1 15A gene described in more detail below. The Imi2 class of nucleic acids includes the TealIMI2 11A gene described below. Each Imi class can include members from different wheat species. Therefore, each Imi class includes IMI nucleic acids that differ in their nucleotide sequence but that are nevertheless designated as originating from, or being located on, the same wheat genome using inheritance studies as described in the Examples below and known to those of ordinary skill in the art.

Accordingly, the present invention includes a wheat plant comprising one or more IMI nucleic acids, wherein the wheat plant has increased resistance to an imidazolinone herbicide as compared to a wild-type variety of the plant and wherein the one or more IMI nucleic acids are selected from a group consisting of an Imi1, Imi2 and Imi3 nucleic acid. In one embodiment, the plant comprises an Imi1 nucleic and an Imi3 nucleic acid. In a preferred embodiment, the Imi1 nucleic acid comprises the polynucleotide sequence shown in SEQ ID NO:1. In another embodiment, the plant comprises an Imi2 nucleic acid. In a preferred embodiment, the Imi2 nucleic acid comprises the polynucleotide sequence shown in SEQ ID NO:3.

As used herein with regard to nucleic acids, the term "from" refers to a nucleic acid "located on" or "derived from" a particular genome. The term "located on" refers to a nucleic acid contained within that particular genome. As also used herein with regard to a genome, the term "derived from" refers to a nucleic acid that has been removed or isolated from that genome. The term "isolated" is defined in more detail below.

In another embodiment, the wheat plant comprises an IMI nucleic acid, wherein the nucleic acid is a non-Imi1 nucleic acid. The term "non-Imi1", refers to an IMI nucleic acid that is not a member of the Imi1 class as described above. Examples of nucleic acids from the Imi1 class are shown in rows 3, 4 and 5 of FIG. 8. One example of non-Imi1 nucleic acid is shown in row 5 of FIG. 8.

Accordingly, in a preferred embodiment, the wheat plant comprises an IMI nucleic acid comprising the polynucleotide sequence encoding the polypeptide of SEQ ID NO:4. The polynucleotide sequence can comprise the sequence shown in SEQ ID NO:3.

The present invention includes wheat plants comprising one, two, three or more IMI nucleic acids, wherein the wheat plant has increased resistance to an imidazolinone herbicide as compared to a wild-type variety of the plant. The IMI nucleic acids can comprise a nucleotide sequence selected from the group consisting of a polynucleotide of SEQ ID NO:1; a polynucleotide of SEQ ID NO:3; a polynucleotide sequence encoding a polypeptide of SEQ ID NO:2; a polynucleotide sequence encoding a polypeptide of SEQ ID NO:4, a polynucleotide comprising at least 60 consecutive nucleotides of any of the aforementioned polynucleotides; and a polynucleotide complementary to any of the aforementioned polynucleotides.

The imidazolinone herbicide can be selected from, but is not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, or a mixture of two or more of the aforementioned herbicides, for example, imazapyr/imazamox (ODYSSEY®). More specifically, the imidazolinone herbicide can be selected from, but is not limited to, 2-(4-isopropyl-4-methyl-5-oxo-2-imidiazolin-2-yl)-nicotinic acid, 2-(4-isopropyl)-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate. The use of 5-ethyl-2-(4-isopropyl-4-methyl-5-oxo-2-imidazolin-2-yl)-nicotinic acid and 2-(4-isopropyl-4-methyl-5-oxo-2-imidazolin-2-yl)-5-(methoxymethyl)-nicotinic acid is preferred. The use of 2-(4-isopropyl-4-methyl-5-oxo-2-imidazolin-2-yl)-5-(methoxymethyl)-nicotinic acid is particularly preferred.

In one embodiment, the wheat plant comprises two IMI nucleic acids, wherein the nucleic acids are derived from or located on different wheat genomes. Preferably, one of the two nucleic acids is an Imi1 nucleic acid, and more preferably comprises the polynucleotide sequence of SEQ ID NO: 1. In another embodiment, the wheat plant comprises one IMI nucleic acid, wherein the nucleic acid comprises the polynucleotide sequence of SEQ ID NO:1 or SEQ ID NO:3. In yet another embodiment, the wheat plant comprises three or more IMI nucleic acids wherein each nucleic acid is from a different genome. Preferably, at least one of the three IMI nucleic acids comprises a polynucleotide sequence selected from the group consisting of SEQ ID NO:1 and SEQ ID NO:3.

In a preferred embodiment of the present invention, the one or more IMI nucleic acids contained within the plant encode an amino acid sequence comprising a mutation in a domain that is conserved among several AHAS proteins. These conserved domains are referred to herein as Domain A, Domain B, Domain C, Domain D and Domain E. FIG. 13 shows the general location of each domain in an AHAS protein. As used herein, Domain A contains the amino acid sequence AIT-GQVPRRMIGT (SEQ ID NO:8); Domain B contains the amino acid sequence QWED (SEQ ID NO:9); Domain C contains the amino acid sequence VFAYPGGASMEIHQAL-TRS (SEQ ID NO:10); Domain D contains the amino acid sequence AFQETP (SEQ ID NO:1 1); Domain E contains the amino acid sequence IPSGG (SEQ ID NO:12). The present invention also contemplates that there may be slight variations in the conserved domains, for example, in cockleberry plants, the serine residue in Domain E is replaced by an alanine residue.

Accordingly, the present invention includes a wheat plant comprising an IMI nucleic acid that encodes an amino acid sequence having a mutation in a conserved domain selected from the group consisting of a Domain A, a Domain B, a Domain C, a Domain D and a Domain E. In one embodiment, the wheat plant comprises an IMI nucleic acid that encodes an amino acid sequence having a mutation in a Domain E. In further preferred embodiments, the mutations in the conserved domains occur at the locations indicated by the following underlining: AITGQVPRRMIGT (SEQ ID NO:8); Q WED (SEQ ID NO:9); VFAYPGGASMEIHQALTRS (SEQ ID NO:10); AFQETP (SEQ ID NO:11) and IPSGG (SEQ ID NO:12). One preferred substitution is asparagine for serine in Domain E (SEQ ID NO: 12).

The wheat plants described herein can be either transgenic wheat plants or non-transgenic wheat plants. As used herein, the term "transgenic" refers to any plant, plant cell, callus, plant tissue or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding. Plants containing mutations arising due to non-spontaneous mutagenesis and selective breeding are referred to herein as non-transgenic plants and are included in the present invention. In embodiments wherein the wheat plant is transgenic and comprises multiple IMI nucleic acids, the nucleic acids can be derived from different genomes or the same genome. Alternatively, in embodiments wherein the wheat plant is non-transgenic and comprises multiple IMI nucleic acids, the nucleic acids are located on different genomes.

An example of a non-transgenic wheat plant cultivar comprising one IMI nucleic acid is the plant cultivar deposited with the ATCC under Patent Deposit Designation Number PTA-3953 and designated herein as the TealIMI 11A wheat cultivar. The TealIMI 11A wheat cultivar contains an Imi2 nucleic acid. The partial nucleotide and deduced amino acid sequences corresponding to the TealIMI2 11A gene are shown in SEQ ID NO:3 and SEQ ID NO:4, respectively. The only portion of the sequences not included in SEQ ID NO:3 and SEQ ID NO:4 are those sequences encoding and corresponding to a signal sequence that is cleaved from the mature TealIMI2 11A protein. Accordingly, SEQ ID NO:4 represents the full deduced sequence of the mature TealIMI2 11A protein.

An example of a wheat plant cultivar comprising two IMI nucleic acids on different genomes is the plant cultivar deposited with the ATCC under Patent Deposit Designation Number PTA-3955 and designated herein as the TealIMI 15A wheat cultivar. The TealIMI 15A wheat cultivar contains Imi1 and Imi3 nucleic acids. The Imi1 nucleic acid comprises a mutation that results in a serine to asparagine change in the IMI protein encoded thereby. The mutated AHAS genes are designated herein as TealIMI1 15A and TealIMI3 15A. The partial nucleotide and deduced amino acid sequences corresponding to the TealIMI1 15A gene are shown in SEQ ID NO: 1 and SEQ ID NO:2, respectively. The only portion of the sequences not included in SEQ ID NO:1 and SEQ ID NO:2 are those sequences encoding and corresponding to approximately 100-150 base pairs at the 5' end and approximately 5 base pairs at the 3' end of the coding region.

Separate deposits of 2500 seeds of the TealIMI 11A and TealIMI 15A wheat cultivars were made with the American Type Culture Collection, Manassas, Va. on Jan. 3, 2002. These deposits were made in accordance with the terms and provisions of the Budapest Treaty relating to the deposit of microorganisms. The deposits were made for a term of at least thirty years and at least five years after the most recent request for the furnishing of a sample of the deposit is received by the ATCC. The deposited seeds were accorded Patent Deposit Designation Numbers PTA-3953 (TealIMI 11A) and PTA-3955 (TealIMI 15A).

The present invention includes the wheat plant having a Patent Deposit Designation Number PTA-3953 or PTA-3955; a mutant, recombinant, or genetically engineered derivative of the plant with Patent Deposit Designation Number PTA-3953 or PTA-3955; any progeny of the plant with Patent Deposit Designation Number PTA-3953 or PTA-3955; and a plant that is the progeny of any of these plants. In a preferred embodiment, the wheat plant of the present invention additionally has the herbicide resistance characteristics of the plant with Patent Deposit Designation Number PTA-3953 or PTA-3955.

Also included in the present invention are hybrids of the TealIMI 11A and TealIMI 15A wheat cultivars described herein. Example 5 demonstrates TealIMI 11A/TealIMI 15A hybrids having increased resistance to an imidazolinone herbicide. The present invention further includes hybrids of the TealIMI 11A or TealIMI 15A wheat cultivars and another wheat cultivar. The other wheat cultivar includes, but is not limited to, T. aestivurn L. cv Fidel and any wheat cultivar harboring a mutant gene FS-1, FS-2, FS-3 or FS-4. (See U.S. Pat. No. 6,339,184 and U.S. patent application Ser. No. 08/474,832). In a preferred embodiment, the wheat plant is a hybrid between a TealIMI 11A cultivar and a Fidel FS-4 cultivar. The TealIMI 11A/FS-4 hybrids comprise an Imi1 nucleic acid and an Imi2 nucleic acid. A hybrid of TealIMI 11A and a Fidel cultivar harboring the FS-4 gene is included in the present invention and was deposited with the American Type Culture Collection, Manassas, Va. on Jan. 3, 2002. This deposit was made in accordance with the terms and provisions of the Budapest Treaty relating to the deposit of microorganisms. The deposit was made for a term of at least thirty years and at least five years after the most recent request for the furnishing of a sample of the deposit is received by the ATCC. The deposited seeds were accorded Patent Deposit Designation Number PTA-3954.

The terms "cultivar" and "variety" refer to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. In the present invention, the trait arises from a mutation in an AHAS gene of the wheat plant or seed.

It is to be understood that the wheat plant of the present invention can comprise a wild type or non-mutated AHAS gene in addition to an IMI gene. As described in Example 4, it is contemplated that wheat cultivar TealIMI 11A contains a mutation in only one of multiple AHAS isoenzymes and that wheat cultivar TealIMI 15A contains a mutation in only two of multiple AHAS isoenzymes. Therefore, the present invention includes a wheat plant comprising one or more IMI nucleic acids in addition to one or more wild type or non-mutated AHAS nucleic acids.

In addition to wheat plants, the present invention encompasses isolated IMI proteins and nucleic acids. The nucleic acids comprise a polynucleotide selected from the group consisting of a polynucleotide of SEQ ID NO: 1; a polynucleotide of SEQ ID NO:3; a polynucleotide sequence encoding a polypeptide of SEQ ID NO:2; a polynucleotide sequence encoding a polypeptide of SEQ ID NO:4, a polynucleotide comprising at least 60 consecutive nucleotides of any of the aforementioned polynucleotides; and a polynucleotide complementary to any of the aforementioned polynucleotides. In a preferred embodiment, the IMI nucleic acid comprises a polynucleotide sequence encoding a polypeptide of SEQ ID NO:2 or SEQ ID NO:4. In a further preferred embodiment, the IMI nucleic acid comprises a polynucleotide sequence of SEQ ID NO:1 or SEQ ID NO:3.

The term "AHAS protein" refers to an acetohydroxyacid synthase protein and the term "IMI protein" refers to any AHAS protein that is mutated from a wild type AHAS protein and that confers increased imidazolinone resistance to a plant, plant cell, plant part, plant seed or plant tissue when it is expressed therein. In a preferred embodiment, the IMI protein comprises a polypeptide of SEQ ID NO:2 or SEQ ID NO:4. As also used herein, the terms "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences that naturally flank the nucleic acid (i.e., sequences located at the 5' and 3' ends of the nucleic acid) in its naturally occurring replicon. For example, a cloned nucleic acid is considered isolated. In various embodiments, the isolated IMI nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Triticum aestivum* cell). A nucleic acid is also considered isolated if it has been altered by human intervention, or placed in a locus or location that is not its natural site, or if it is introduced into a cell by agroinfection or biolistics. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule containing a nucleotide sequence of SEQ ID NO:1, SEQ ID NO:3 or a portion thereof, can be isolated using standard molecular biology techniques and the sequence information provided herein. For example, a *T. aestivum* IMI cDNA can be isolated from a *T. aestivum* library using all or a portion of the sequence of SEQ ID NO:1 or SEQ ID NO:3. Moreover, a nucleic acid molecule encompassing all or a portion of SEQ ID NO:1 or SEQ ID NO:3 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1 or SEQ ID NO:3. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an IMI nucleotide sequence can be prepared by standard synthetic techniques, e.g., using an automated DNA synthesizer.

The IMI nucleic acids of the present invention can comprise sequences encoding an IMI protein (i.e., "coding regions"), as well as 5' untranslated sequences and 3' untranslated sequences: Alternatively, the nucleic acid molecules of the present invention can comprise only the coding regions of an IMI gene, or can contain whole genomic fragments isolated from genomic DNA. A coding region of these sequences is indicated as an "ORF position". Moreover, the nucleic acid molecule of the invention can comprise a portion of a coding region of an IMI gene, for example, a fragment that can be used as a probe or primer. The nucleotide sequences determined from the cloning of the IMI genes from *T. aestivum* allow for the generation of probes and primers designed for use in identifying and/or cloning IMI homologs in other cell types and organisms, as well as IMI homologs from other wheat plants and related species. The portion of the coding region can also encode a biologically active fragment of an IMI protein.

As used herein, the term "biologically active portion of" an IMI protein is intended to include a portion, e.g., a domain/motif, of an IMI protein that, when produced in a plant increases the plant's resistance to an imidazolinone herbicide as compared to a wild-type variety of the plant. Methods for quantitating increased resistance to imidazolinone herbicides are provided in the Examples provided below. Biologically active portions of an IMI protein include peptides encoded by polynucleotide sequences comprising SEQ ID NO:1 or SEQ ID NO:3 which include fewer amino acids than a full length IMI protein and impart increased resistance to an imidazolinone herbicide upon expression in a plant. Typically, biologically active portions (e.g., peptides which are, for example, 5, 10, 15, 20, 30, 35, 36, 37, 38, 39, 40, 50, 100 or more amino acids in length) comprise a domain or motif with at least one activity of an IMI protein. Moreover, other biologically active portions in which other regions of the polypeptide are deleted, can be prepared by recombinant techniques and evaluated for one or more of the activities described herein. Preferably, the biologically active portions of an IMI protein include one or more conserved domains selected from the group consisting of a Domain A, a Domain B, a Domain C, a Domain D and a Domain E, wherein the conserved domain contains a mutation.

The invention also provides IMI chimeric or fusion polypeptides. As used herein, an IMI "chimeric polypeptide" or "fusion polypeptide" comprises an IMI polypeptide operatively linked to a non-IMI polypeptide. A "non-IMI polypeptide" refers to a polypeptide having an amino acid sequence that is not substantially identical to an IMI polypeptide, e.g., a polypeptide that is not an IMI isoenzyme, which peptide performs a different function than an IMI polypeptide. Within the fusion polypeptide, the term "operatively linked" is intended to indicate that the IMI polypeptide and the non-IMI polypeptide are fused to each other so that both sequences fulfill the proposed function attributed to the sequence used. The non-IMI polypeptide can be fused to the N-terminus or C-terminus of the IMI polypeptide. For example, in one embodiment, the fusion polypeptide is a GST-IMI fusion polypeptide in which the IMI sequence is fused to the C-terminus of the GST sequence. Such fusion polypeptides can facilitate the purification of recombinant IMI polypeptides. In another embodiment, the fusion polypeptide is an IMI polypeptide containing a heterologous signal sequence at its N-terminus. In certain host cells (e.g., mammalian host cells), expression and/or secretion of an IMI polypeptide can be increased through use of a heterologous signal sequence.

An isolated nucleic acid molecule encoding an IMI polypeptide having sequence identity to a polypeptide encoded by a polynucleotide sequence of SEQ ID NO:1 or SEQ ID NO:3 can be created by introducing one or more nucleotide substitutions, additions or deletions into a nucleotide sequence of SEQ ID NO:1 or SEQ ID NO:3 such that one or more amino acid substitutions, additions or deletions are introduced into the encoded polypeptide. Mutations can be introduced into a sequence of SEQ ID NO:1 or SEQ ID NO:3 by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an IMI polypeptide is preferably replaced with another amino acid residue from the same side chain family. Alternatively, in another embodiment, mutations can be introduced randomly along all or part of an IMI coding sequence, such as by saturation mutagenesis, and the resultant mutants can be screened for an IMI activity described herein to identify mutants that retain IMI activity. Following mutagenesis of the sequence of SEQ ID NO:1 or SEQ ID NO:3, the encoded polypeptide can be expressed recombinantly and the activity of the polypeptide can be determined by analyzing the imidazolinone resistance of a plant expressing the polypeptide as described in the Examples below.

To determine the percent sequence identity of two amino acid sequences (e.g., SEQ ID NO:2 or SEQ ID NO:4 and a mutant form thereof), the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence (e.g., SEQ ID NO:2 or SEQ ID NO:4) is occupied by the same amino acid residue as the corresponding position in the other sequence (e.g., a mutant form of SEQ ID NO:2 or SEQ ID NO:4), then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. It is to be understood that for the purposes of determining sequence identity, when comparing a DNA sequence to an RNA sequence, a thymidine nucleotide is equivalent to a uracil nucleotide. Preferably, the isolated IMI polypeptides included in the present invention are at least about 50-60%, preferably at least about 60-70%, and more preferably at least about 70-75%, 75-80%, 80-85%, 85-90% or 90-95%, and most preferably at least about 96%, 97%, 98%, 99% or more identical to an entire amino acid sequence encoded by a polynucleotide sequence shown in SEQ ID NO:1 or SEQ ID NO:3. In another embodiment, the isolated IMI polypeptides included in the present invention are at least about 50-60%, preferably at least about 60-70%, and more preferably at least about 70-75%, 75-80%, 80-85%, 85-90% or 90-95%, and most preferably at least about 96%, 97%, 98%, 99% or more identical to an entire amino acid sequence shown in SEQ ID NO:2 or SEQ ID NO:4.

Additionally, optimized IMI nucleic acids can be created. Preferably, an optimized IMI nucleic acid encodes an IMI polypeptide that modulates a plant's tolerance to imidazolinone herbicides, and more preferably increases a plant's tolerance to an imidazolinone herbicide upon its over-expression in the plant. As used herein, "optimized" refers to a nucleic acid that is genetically engineered to increase its expression in a given plant or animal. To provide plant optimized IMI nucleic acids, the DNA sequence of the gene can be modified to 1) comprise codons preferred by highly expressed plant genes; 2) comprise an A+T content in nucleotide base composition to that substantially found in plants; 3) form a plant initiation sequence, 4) eliminate sequences that cause destabilization, inappropriate polyadenylation, degradation and termination of RNA, or that form secondary structure hairpins or RNA splice sites. Increased expression of IMI nucleic acids in plants can be achieved by utilizing the distribution frequency of codon usage in plants in general or a particular plant. Methods for optimizing nucleic acid expression in plants can be found in EPA 0359472; EPA 0385962; PCT Application No. WO 91/16432; U.S. Pat. Nos. 5,380,831; 5,436,391; Perlack et al., 1991 Proc. Natl. Acad. Sci. USA 88:3324-3328; and Murray et al., 1989 Nucleic Acids Res. 17:477-498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation 1A=n=1 $ZX_n-Y_nX_n$ times 100 Z where $X_n$=frequency of usage for codon n in the host cell; $Y_n$=frequency of usage for codon n in the synthetic gene, n represents an individual codon that specifies an amino acid and the total number of codons is Z. The overall deviation of the frequency of codon usage, A, for all amino acids should preferably be less than about 25%, and more preferably less than about 10%.

Hence, an IMI nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized IMI nucleic acids of this invention also preferably have CG and TA doublet avoidance indices closely approximating those of the chosen host plant (i.e., *Triticum aestivum*). More preferably these indices deviate from that of the host by no more than about 10-15%.

In addition to the nucleic acid molecules encoding the IMI polypeptides described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation and/or stability of the target polynucleotide. Methods are described in the prior art for targeting the antisense polynucleotide to the chromosomal DNA, to a primary RNA transcript or to a processed mRNA. Preferably, the target regions include splice sites, translation initiation codons, translation termination codons, and other sequences within the open reading frame.

The term "antisense", for the purposes of the invention, refers to a nucleic acid comprising a polynucleotide that is sufficiently complementary to all or a portion of a gene, primary transcript or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide encoded by the polynucleotide sequence of SEQ ID NO:1 or SEQ ID NO:3.

In addition to the IMI nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of the sequence set forth in SEQ ID NO:1 or SEQ ID NO:3, an anti-sense sequence of the sequence set forth in SEQ ID NO:1 or SEQ ID NO:3, or naturally occurring mutants thereof Primers based on a nucleotide sequence of SEQ ID NO:1 or SEQ ID NO:3 can be used in PCR reactions to clone IMI homologs. Probes based on the IMI nucleotide sequences can be used to detect transcripts or genomic sequences encoding the same or homologous polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an IMI polypeptide, such as by measuring a level of an IMI-encoding nucleic acid, in a sample of cells, e.g., detecting IMI mRNA levels or determining whether a genomic IMI gene has been mutated or deleted.

The invention further provides an isolated recombinant expression vector comprising an IMI nucleic acid as described above, wherein expression of the vector in a host cell results in increased resistance to an imidazolinone herbicide as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/ translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., IMI polypeptides, fusion polypeptides, etc.).

In a preferred embodiment of the present invention, the IMI polypeptides are expressed in plants and plants cells such as unicellular plant cells (such as algae) (see Falciatore et al., 1999 Marine Biotechnology 1(3):239-251 and references therein) and plant cells from higher plants (e.g., the spermatophytes, such as crop plants). An IMI polynucleotide may be "introduced" into a plant cell by any means, including transfection, transformation or transduction, electroporation, particle bombardment, biolistics, agroinfection and the like. One transformation method known to those of skill in the art is the dipping of a flowering plant into an Agrobacteria solution, wherein the Agrobacteria contains the IMI nucleic acid, followed by breeding of the transformed gametes.

Other suitable methods for transforming or transfecting host cells including plant cells can be found in Sambrook, et al. (Molecular Cloning: A Laboratory Manual. $2^{nd}$, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As increased resistance to imidazolinone herbicides is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, *Vicia* species, pea, alfalffa, bushy plants (coffee, cacao, tea), *Salix* species, trees (oil palm, coconut), perennial grasses and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover and Sweet Clover.

In one embodiment of the present invention, transfection of an IMI polynucleotide into a plant is achieved by *Agrobacterium* mediated gene transfer. *Agrobacterium* mediated plant transformation can be performed using for example the GV3101(pMP90) (Konoz and Schell, 1986 Mol. Gen. Genet. 204:383-396) or LBA4404 (Clontech) *Agrobacterium tumefaciens* strain. Transformation can be performed by standard transformation and regeneration techniques (Deblaere et al., 1994 Nucl. Acids. Res. 13:4777-4788; Gelvin, Stanton B. and Schilperoort, Robert A, Plant Molecular Biology Manual, $2^{nd}$ Ed.—Dordrecht : Kluwer Academic Publ., 1995.—in Sect., Ringbuc Zentrale Signatur: BT11-P ISBN 0-7923-2731-4; Glick, Bernard R. and Thompson, John E., Methods in Plant Molecular Biology and Biotechnology, Boca Raton : CRC Press, 1993 360 S., ISBN 0-8493-5164-2). For example, rapeseed can be transformed via cotyledon or hypocotyl transformation (Moloney et al., 1989 Plant cell Report 8:238-242; De Block et al., 1989 Plant Physiol. 91:694-701). Use of antibiotica for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994 Plant Cell Report 13:282-285. Additionally, transformation of soybean can be performed using, for example, a technique described in European Patent No. 0424 047, U.S. Pat. No. 5,322,783, European Patent No. 0397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is fotmd in U.S. Pat. No. 5,990,387 and a specific example of wheat transformation can be found in PCT Application No. WO 93/07256.

According to the present invention, the introduced IMI polynucleotide may be maintained in the plant cell stably if it is incorporated into a non-chromosomal autonomous replicon or integrated into the plant chromosomes. Alternatively, the introduced IMI polynucleotide may be present on an extra-chromosomal non-replicating vector and be transiently expressed or transiently active. In one embodiment, a homologous recombinant microorganism can be created wherein the IMI polynucleotide is integrated into a chromosome, a vector is prepared which contains at least a portion of an AHAS gene into which a deletion, addition or substitution has been introduced to thereby alter, e.g., functionally disrupt, the endogenous AHAS gene and to create an IMI gene. To create a point mutation via homologous recombination, DNA-RNA hybrids can be used in a technique known as chimeraplasty (Cole-Strauss et al., 1999 Nucleic Acids Research 27(5):1323-1330 and Kmiec, 1999 Gene therapy American Scientist 87(3):240-247). Other homologous recombination procedures in *Triticum* species are also well known in the art and are contemplated for use herein.

In the homologous recombination vector, the IMI gene can be flanked at its 5' and 3' ends by an additional nucleic acid molecule of the AHAS gene to allow for homologous recombination to occur between the exogenous IMI gene carried by the vector and an endogenous AHAS gene, in a microorganism or plant. The additional flanking AHAS nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95(8):4368-4373 for cDNA based recombination in *Physcomitrella patens*). However, since the IMI gene normally differs from the AHAS gene at very few amino acids, a flanking sequence is not always necessary. The homologous recombination vector is introduced into a microorganism or plant cell (e.g., via polyethylene glycol mediated DNA), and cells in which the introduced IMI gene has homologously recombined with the endogenous AHAS gene are selected using art-known techniques.

In another embodiment, recombinant microorganisms can be produced that contain selected systems that allow for regulated expression of the introduced gene. For example, inclusion of an IMI gene on a vector placing it under control of the lac operon permits expression of the IMI gene only in the presence of IPTG. Such regulatory systems are well known in the art.

Whether present in an extra-chromosomal non-replicating vector or a vector that is integrated into a chromosome, the IMI polynucleotide preferably resides in a plant expression cassette. A plant expression cassette preferably contains regulatory sequences capable of driving gene expression in plant cells that are operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof, but also all other terminators functionally active in plants are suitable. As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the polypeptide per RNA ratio (Gallie et al., 1987 Nucl. Acids Research 15:8693-8711). Examples of plant expression vectors include those detailed in: Becker, D. et al., 1992 New plant binary vectors with selectable markers located proximal to the left border, Plant Mol. Biol. 20:1195-1197; Bevan, M. W., 1984 Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operably linked to an appropriate promoter conferring gene expression in a timely, cell or tissue specific manner. Promoters useful in the expression cassettes of the invention include any promoter that is capable of initiating transcription in a plant cell. Such promoters include, but are not limited to those that can be obtained from plants, plant viruses and bacteria that contain genes that are expressed in plants, such as *Agrobacterium* and *Rhizobium*.

The promoter may be constitutive, inducible, developmental stage-preferred, cell type-preferred, tissue-preferred or organ-preferred. Constitutive promoters are active under most conditions. Examples of constitutive promoters include the CaMV 19S and 35 S promoters (Odell et al. 1985 Nature 313:810-812), the sX CaMV 35S promoter (Kay et al. 1987 Science 236:1299-1302) the Sep1 promoter, the rice actin promoter (McElroy et al. 1990 Plant Cell 2:163-171), the *Arabidopsis* actin promoter, the ubiquitan promoter (Christensen et al. 1989 Plant Molec Biol. 18:675-689); pEmu (Last et a. 1991 Theor Appl Genet. 81:581-588), the figwort mosaic virus 35S promoter, the Smas promoter (Velten et al. 1984 EMBO J. 3:2723-2730), the GRP1-8 promoter, the cinnamyl alcohol dehydrogenase promoter (U.S. Pat. No. 5,683,439), promoters from the T-DNA of Agrobacterium, such as mannopine synthase, nopaline synthase, and octopine synthase, the small subunit of ribulose biphosphate carboxylase (ssu-RUBISCO) promoter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock, the PPDK promoter is induced by light, the PR-1 promoter from tobacco, *Arabidopsis* and maize are inducible by infection with a pathogen, and the Adh1 promoter is induced by hypoxia and cold stress. Plant gene expression can also be facilitated via an inducible promoter (for review see Gatz, 1997 Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992 Plant J. 2:397-404) and an ethanol inducible promoter (PCT Application No. WO 93/21334).

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stempreferred, root-preferred promoters and the like. Seed preferred promoters are preferentially expressed during seed development and/or germination. For example, seed preferred promoters can be embryo-preferred, endosperm preferred and seed coat-preferred. See Thompson et al. 1989 BioEssays 10:108. Examples of seed preferred promoters include, but are not limited to cellulose synthase (celA), Cim1, gamma-zein, globulin-1, maize 19 kD zein (cZ19B1) and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991 Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980) or the legumin B4 promoter (LeB4; Baeumlein et al., 1992 Plant Journal, 2(2): 233-9) as well as promoters conferring seed specific expression in monocot plants like maize, barley, wheat, rye, rice, etc. Suitable promoters to note are the 1pt2 or 1pt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene and rye secalin gene).

Other promoters useful in the expression cassettes of the invention include, but are not limited to, the major chlorophyll a/b binding protein promoter, histone promoters, the Ap3 promoter, the -conglycin promoter, the napin promoter, the soy bean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086,169), the maize polygalacturonase promoters (PG) (U.S. Pat. Nos. 5,412,085 and 5,545,546) and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, Cell 43:729-736 (1985)).

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an IMI polynucleotide can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) an IMI polynucleotide. Accordingly, the invention further provides methods for producing IMI polypeptides using the host cells of the invention. In one embodiment, the method comprises culturing the host cell of invention (into which a recombinant expression vector encoding an IMI polypeptide has been introduced, or into which genome has been introduced a gene encoding a wild-type or IMI polypeptide) in a suitable medium until IMI polypeptide is produced. In another embodiment, the method further comprises isolating IMI polypeptides from the medium or the host cell.

Another aspect of the invention pertains to isolated IMI polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of IMI polypeptide in which the polypeptide is separated from some of the cellular components of the cells in which it is naturally or recombinantly produced. In one embodiment, the language "substantially free of cellular material" includes preparations of an IMI polypeptide having less than about 30% (by dry weight) of non-IMI material (also referred to herein as a "contaminating polypeptide"), more preferably less than about 20% of non-IMI material, still more preferably less than about 10% of non-IMI material, and most preferably less than about 5% non-IMI material.

When the IMI polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of IMI polypeptide in which the polypeptide is separated from chemical precursors or other chemicals that are involved in the synthesis of the polypeptide. In one embodiment, the language "substantially free of chemical precursors or other chemicals" includes preparations of an IMI polypeptide having less than about 30% (by dry weight) of chemical precursors or non-IMI chemicals, more preferably less than about 20% chemical precursors or non-IMI chemicals, still more preferably less than about 10% chemical precursors or non-IMI chemicals, and most preferably less than about 5% chemical precursors or non-IMI chemicals. In preferred embodiments, isolated polypeptides, or biologically active portions thereof, lack contaminating polypeptides from the same organism from which the IMI polypeptide is derived. Typically, such polypeptides are produced by recombinant expression of, for example, a *Triticum aestivum* IMI polypeptide in plants other than Triticum aestivum or microorganisms such as *C. glutamicum*, ciliates, algae or fungi.

The IMI polynucleotide and polypeptide sequences of the invention have a variety of uses. The nucleic acid and amino acid sequences of the present invention can be used to transform plants, thereby modulating the plant's resistance to imidazolinone herbicides. Accordingly, the invention provides a method of producing a transgenic plant having increased tolerance to an imidazolinone herbicide comprising, (a) transforming a plant cell with one or more expression vectors comprising one or more IMI nucleic acids, and (b) generating from the plant cell a transgenic plant with an increased resistance to an imidazolinone herbicide as compared to a wild type variety of the plant. In one embodiment, the multiple IMI nucleic acids are derived from different genomes. Also included in the present invention are methods of producing a transgenic plant having increased tolerance to an imidazolinone herbicide comprising, (a) transforming a plant cell with an expression vector comprising an IMI nucleic acid, wherein the nucleic acid is a non-Imi1 nucleic acid and (b) generating from the plant cell a transgenic plant with an increased resistance to an imidazolinone herbicide as compared to a wild type variety of the plant.

The present invention includes methods of modifying a plant's tolerance to an imidazolinone herbicide comprising modifying the expression of one or more IMI nucleic acids. Preferably, the nucleic acids are located on or derived from different genomes. The plant's resistance to the imidazolinone herbicide can be increased or decreased as achieved by increasing or decreasing the expression of an IMI polynucleotide, respectively. Preferably, the plant's resistance to the imidazolinone herbicide is increased by increasing expression of an IMI polynucleotide. Expression of an IMI polynucleotide can be modified by any method known to those of skill in the art. The methods of increasing expression of IMI polynucleotides can be used wherein the plant is either transgenic or not transgenic. In cases when the plant is transgenic, the plant can be transformed with a vector containing any of the above described IMI coding nucleic acids, or the plant can be transformed with a promoter that directs expression of endogenous IMI polynucleotides in the plant, for example. The invention provides that such a promoter can be tissue specific or developmentally regulated. Alternatively, non-transgenic plants can have endogenous IMI polynucleotide expression modified by inducing a native promoter. The expression of polynucleotides comprising SEQ ID NO:1 or SEQ ID NO:3 in target plants can be accomplished by, but is not limited to, one of the following examples: (a) constitutive promoter, (b) chemical-induced promoter, and (c) engineered promoter over-expression with for example zinc-finger derived transcription factors (Greisman and Pabo, 1997 Science 275:657).

In a preferred embodiment, transcription of the IMI polynucleotide is modulated using zinc-finger derived transcription factors (ZFPs) as described in Greisman and Pabo, 1997 Science 275:657 and manufactured by Sangamo Biosciences, Inc. These ZFPs comprise both a DNA recognition domain and a functional domain that causes activation or repression of a target nucleic acid such as an IMI nucleic acid. Therefore, activating and repressing ZFPs can be created that specifically recognize the IMI polynucleotide promoters described above and used to increase or decrease IMI polynucleotide expression in a plant, thereby modulating the herbicide resistance of the plant.

As described in more detail above, the plants produced by the methods of the present invention can be monocots or dicots. The plants can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass and forage crops, for example. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover and Sweet Clover. In a preferred embodiment, the plant is a wheat plant. In each of the methods described above, the plant cell includes, but is not limited to, a protoplast, gamete producing cell, and a cell that regenerates into a whole plant. As used herein, the term "transgenic" refers to any plant, plant cell, callus, plant tissue or plant part, that contains all or part of at least one recombinant polynucleotide. In many cases, all or part of the recombinant polynucleotide is stably integrated into a chromosome or stable extra-chromosomal element, so that it is passed on to successive generations.

As described above, the present invention teaches compositions and methods for increasing the imidazolinone resistance of a wheat plant or seed as compared to a wild-type variety of the plant or seed. In a preferred embodiment, the imidazolinone resistance of a wheat plant or seed is increased such that the plant or seed can withstand an imidazolinone herbicide application of preferably approximately 10-400 g ai ha$^{-1}$, more preferably 20-160 g ai ha$^{-1}$, and most preferably 40-80 g ai ha$^{-1}$. As used herein, to "withstand" an imidazolinone herbicide application means that the plant is either not killed or not injured by such application.

Additionally provided herein is a method of controlling weeds within the vicinity of a wheat plant, comprising applying an imidazolinone herbicide to the weeds and to the wheat plant, wherein the wheat plant has increased resistance to the imidazolinone herbicide as compared to a wild type variety of the wheat plant, and wherein the plant comprises one or more IMI nucleic acids. In one embodiment, the plant comprises multiple IMI nucleic acids located on or derived from different genomes. In another embodiment, the plant comprises a non-Imi1 nucleic acid. By providing for wheat plants having increased resistance to imidazolinone, a wide variety of formulations can be employed for protecting wheat plants from weeds, so as to enhance plant growth and reduce competition for nutrients. An imidazolinone herbicide can be used by itself for pre-emergence, post-emergence, pre-planting and at-planting control of weeds in areas surrounding the wheat plants described herein or an imidazolinone herbicide formulation can be used that contains other additives. The imidazolinone herbicide can also be used as a seed treatment. Additives found in an imidazolinone herbicide formulation include other herbicides, detergents, adjuvants, spreading agents, sticking agents, stabilizing agents, or the like. The imidazolinone herbicide formulation can be a wet or dry preparation and can include, but is not limited to, flowable powders, emulsifiable concentrates and liquid concentrates. The imidazolinone herbicide and herbicide formulations can be applied in accordance with conventional methods, for example, by spraying, irrigation, dusting, or the like.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Mutagenesis and Selection of Resistant Wheat Lines

Approximately 40,000 seeds of *Triticum aestivum* L. cv CDC Teal (Hughes and Hucl, 1993 Can. J. Plant Sci. 73:193-197) were mutagenized using modified procedures described by Washington and Sears (1970). Seeds were pre-soaked in distilled water for four hours, followed by treatment with 0.3% EMS for six hours. Seeds were rinsed continually with tap water for seven hours and allowed to dry for approximately four hours before being planted in the field. The $M_1$ plants were selfed and the seed was harvested in bulk. Approximately $2 \times 10^6$ $M_2$ plants were grown in the field the following year and were sprayed at the two leaf stage with imazamox at a rate of 40 g ai ha$^{-1}$ in a spray volume of 100 L ha$^{-1}$. Merge 0.05% (v/v) adjuvant was added to the spray solution. Six lines resistant to imazamox were selected and designated as lines 1A, 9A, 10A, 11A, 15A, and 16A. The $M_3$ and $M_4$ generations were grown in a walk-in growth chamber and plants resistant to imazamox were selected using rates of 20 g ai ha$^{-1}$. Resistant plants were selected in the $M_5$ generation after application of 40 g ai ha$^{-1}$ in the field. $M_5$ seed was homozygous for the trait, as progeny testing detected no segregation for resistance to imazamox.

Example 2

Methods Used to Determine Inheritance and Allelism of IMI genes

To determine the genetic control of resistance to imazamox in the six wheat lines, reciprocal crosses between the six homozygous resistant $M_6$ lines and CDC Teal (susceptible to imazamox) were made. Randomly selected $F_1$ plants from each of the crosses were backcrossed to CDC Teal to form backcross (BC)$F_1$ populations. To investigate allelism, all possible inter-crosses between the six mutants and SWP965001 (Grandin/3*Fidel—FS-4) were made. SWP965001 is a spring wheat line that is homozygous for the FS-4 allele. Parental genotypes were grown in a walk-in growth chamber with a 16 hour photoperiod and a 24° C. day and 16° C. night temperature regime. Spikes that were ¾ emerged from the boot were emasculated and then pollinated 2-3 days after the emasculation date. Randomly selected $F_2$ plants from all segregating crosses were selfed to produce $F_{2:3}$ families. Parental, $F_1$, BCF$_1$, $F_2$ plants and $F_{2:3}$ families were tested for reaction to imazamox. All experiments were conducted in a walk-in growth chamber with a 16 hour photoperiod and a 23° C. day and 16° C. night temperature regime. A completely random design was used for all experiments. In experiments involving $F_{2:3}$ families, effort was taken to randomize both within and among families. The $F_1$ and $F_2$ populations were screened in the same experiment along with parental genotypes and CDC Teal as controls. Both the BCF$_1$ and $F_{2:3}$ populations were screened in two separate experiments along with appropriate parental genotypes as controls.

Herbicide treatments were applied to plants growing in 8×16 cell flats at the two leaf stage using a traveling cable sprayer calibrated to spray 100 L ha$^{-1}$. Imazamox was applied to plants at a rate of 20 g ai ha$^{-1}$ using an 8001 EVS nozzle at a pressure of 275 kPa. Merge surfactant (0.05% v/v) was added to the herbicide solution prior to application. Fifteen days after herbicide application, plants were rated based on parental reactions and were considered as resistant, intermediate, or susceptible. Resistant plants were phenotypically unaffected following herbicide treatment whereas intermediate plants were characterized by halted growth of the first two leaves, darkening (dark-green pigmentation) of the leaves, and the emergence of coleoptilar tillers. Susceptible plants were characterized by failure to develop new leaves, extensive leaf chlorosis, and eventually, plant death. For Mendelian analysis of the segregating populations, plants were scored into resistant and susceptible categories and tested for goodness of fit to various 1 gene, 2 gene and 3 gene models using chi-square analysis. For $F_2$ and BCF$_1$ plant data, intermediate reactions were included in the resistant reaction category. Yates correction for continuity was used to adjust the chi-square value when only a single degree of freedom was used in the chi-square analysis (Steele and Torrie 1980 Principles and procedures of statistics. McGraw-Hill, New York, N.Y. pp 633).

Example 3

Results Regarding Inheritance of IMI Genes

All resistant parents produced a similar phenotype when sprayed with 20 g ai ha$^{-1}$ of imazamox. (FIG. 1). Reciprocal crosses between the resistant lines and the susceptible parent (CDC Teal) resulted in Ft plants that survived application of imazamox (FIG. 1), indicating that resistance to imazamox is a nuclear and not a cytoplasmic trait. With the exception of cross 15A×Teal, the Ft plants resulting from each of the resistant lines crossed with CDC Teal displayed an intermediate reaction (FIG. 1). Since the Ft plants were phenotypically intermediate between the two parents, it was concluded that resistance to imazamox in these lines was a partially dominant trait (FIG. 1). Genetic analysis of resistance to imidazolinones and sulfonylureas in *Arabidopsis thaliana* (Haughn and Somerville, 1986 Mol. Gen. Genet. 204:430-434) *Zea mays* (Newhouse et al., 1991 Theor. Appl. Genet. 83:65-70), *Brassica napus* (Swanson et al., 1989 Theor. Appl. Gen. 78:525-530), and *Glycine max* (Sebastian et al., 1989 Crop Sci. 29:1403-1408) also indicated the presence of a single, partially dominant nuclear gene.

Fourteen $F_1$ plants resulting from the 15A×Teal cross were rated as resistant (FIG. 1). Evaluation of $F_2$ populations from this cross indicated that two independently segregating loci were involved in conferring resistance in this genotype (FIG. 2). Since the $F_1$ would carry two heterozygous resistant loci, one would expect that a resistant reaction would be observed. If each of these loci alone would confer partial dominance, additively, two heterozygous loci would produce a resistant reaction. Swanson et al. (1989) combined two semi-dominant imidazolinone resistance alleles from *Brassica napus*, representing two unlinked genes, to produce a $F_1$ hybrid that was superior in imidazolinone resistance than either of the heterozygous lines alone. The authors concluded that resistance mechanisms are additive, and a higher level of resistance is observed in lines carrying more than one resistance allele.

An analysis of cytoplasmic inheritance was conducted in the $F_2$ generation by testing homogeneity of deviations from segregation ratios between the two reciprocal $F_2$ populations. Chi-square analysis revealed no significant deviations between reciprocal populations, confirming the absence of cytoplasmic inheritance (FIG. 2). Since cytoplasmic inheritance was absent, data from the two reciprocal populations was combined and a total chi-square on pooled $F_2$ data was calculated (FIG. 2).

With the exception of Teal×15A, all $F_2$ populations resulting from resistant x susceptible crosses gave a good fit to a 3:1 resistant susceptible ratio indicating segregation of a single major gene for resistance to imazamox (FIG. 2). When $F_1$ plants were crossed to the susceptible parent, resulting BCF$_1$ populations gave a good fit to a 1:1 resistant:susceptible ratio, confirming the single locus hypothesis (FIG. 2). The $F_2$ population data from the cross 15A×Teal fit a 15:1 resistant:susceptible ratio (P=0.08), indicating segregation of two independent, complementary genes (FIG. 2). The BCFP population gave good fit to a 3:1 resistant:susceptible ratio with a chi-square P value of 0.35, confirming the results of the $F_2$ (FIG. 2).

Since it is speculated from $F_2$ data that resistance in lines 1A, 9A, 10A, 11A, and 16A are controlled by a single major gene, $F_{2:3}$ families should segregate and fit a 1:2:1 homozygous resistance: segregating: homozygous susceptible family ratio. Evaluation of $F_{2:3}$ families indicated that crosses Teal× 1A, Teal×9A, Teal×10A, Teal×11A, and Teal×16A all fit a 1:2:1 resistant: segregating: susceptible $F_{2:3}$ family ratio with chi-square P values of 0.64, 0.66, 0.52, 0.40, and 0.94, respectively (FIG. 3). These results confirm the results of the $F_2$ and $BCF_1$ data that resistance in lines 1A, 10A, 9A, 11A, and resistance in 16A is controlled by a single major gene. This pattern of inheritance is consistent with other findings that have reported the genetic control of resistance to AHAS inhibitor herbicides. To date, nearly all plant mutations conferring resistance to imidazolinones show that a single, partially dominant gene controls the resistance trait. In *Triticum aestivum, Zea mays, Glycine max, Arabidopsis thaliana*, and *Nicotiana tabacum*, resistance to AHAS inhibitors is inherited as a single partially dominant nuclear gene (Newhouse et al. 1991; Newhouse et al. 1992; Chaleff and Ray, 1984 Science 223:1148-1151; Sathasivan et al., 1991 Plant Physiol. 97:1044-1050). Plant resistance to AHAS inhibitor herbicides occurs mostly because of a single point mutation to the gene encoding the AHAS enzyme (Harms et al. 1992, Mol. Gen. Genet. 233:427-435; Winder and Spalding, 1988 Mol. Gen. Genet. 238:394-399).

The $F_2$ data resulting from the cross Teal×15A provided a good fit to a 15:1 resistant:susceptible ratio, suggesting segregation of two, independently segregating loci (FIG. 2). If this is the case, $F_{2:3}$ families should segregate and fit a 7:8:1 resistant:segregating:susceptible $F_{2:3}$ family ratio. $F_{2:3}$ families from the cross 15A×Teal did fit the expected 7:8:1 ratio (FIG. 3), confirming the results of the $F_2$ and $BCF_1$ populations that resistance in 15A is conferred by two, independent loci. To the inventor's knowledge, this is the first reported instance were two independently segregating imidazolinone resistant alleles were identified in a single line following seed mutagenesis.

Example 4

Results Regarding Allelism of IMI genes

To determine the allelic relationships of resistance genes, all possible intercrosses between resistant lines were evaluated. No susceptible plants were observed in the $F_2$ populations resulting from the inter-crosses between lines SWP965001, 1A, 9A, 10A, 15A, and 16A (FIG. 4). Since these populations were not segregating, the resistance genes in these lines are either alleles at the FS-4 locus, or are very tightly linked. Since these populations were not segregating in the $F_2$ generation, $F_{2:3}$ families from these crosses were not evaluated.

All inter-crosses involving line 11A did segregate in the $F_2$ generation, indicating the presence of a unique resistance gene in 11A (FIG. 4). If two independently segregating resistance genes are present as the result of crossing two lines, each carrying a single resistance gene, a 15:1 resistant:susceptible ratio would be expected in the $F_2$ generation. In the $F_2$ generation, crosses SWP965001×11A, 1A×11A, 10A×11A, and 16A×11A fit the expected 15:1 resistant:susceptible ratio suggesting independent segregation of two major resistance genes (FIG. 4). $F_{2:3}$ family ratios from these crosses also gave a good fit to a 7:8:1 resistant:segregating:susceptible ratio, confirming the results obtained in the $F_2$ generation (FIG. 5). Cross 11A×9A did produce a segregating $F_2$ population, but the ratio did not fit a 15:1 segregation ratio due to an excess of susceptible segregants. Various other two gene hypotheses were tested, but all were found to be highly significant (Data not shown). Evaluation of $F_{2:3}$ families from this cross, however did give good fit to a 7:8:1 segregation ratio, indicating segregation of two independent genes (FIG. 5). These results confirm that the resistance gene in 11A is unique from those in lines SWP96001, 1A, 9A, 10A, and 16A.

Cross 11A×15A did produce a segregating $F_2$ population. Since 15A is carrying two resistance genes, one allelic to FS-4, a segregating $F_2$ population in cross 11A×15A would indicate the presence of three segregating genes. Segregating generations resulting from cross 15A×11A were tested for segregation of three independent loci. $F_2$ plants did fit the expected 63:1 resistant:susceptible ratio, indicating the segregation of three independent loci (FIG. 4). These results suggest that the second mutation in 15A is not allelic to the resistance gene in 1A. $F_{2:3}$ families were not screened as over 330 plants within each family would have to be screened in order to ensure an adequate power of test (Hanson, 1959 Agron. J. 51:711-716).

Three independent resistance loci have been identified, each with an allele conferring resistance to imazamox. Recommended rules for gene locus and allele symbolization have been published (McIntosh et al., 1998 Catalogue of Gene Symbols. Volume 5, Proceedings of the 9th International Wheat Genetics Symposium. Saskatoon, Saskatchewan). Non-allelic gene loci of an enzyme that catalyze the same reaction should be given the same symbol, corresponding to the trivial name of the enzyme. The trivial name for AHAS is ALS. Absent data to assign the loci to specific chromosomes and genomes, they should be designated in sequential series. The designation of the phenotype observed when changes occur in the gene resulting in a new allele should reflect that phenotype. Thus, it is proposed that the FS-4 imidazolinone resistance allele be designated as Imi1 and the locus it is at designated as Als1. Imi stands for imidazolinone resistance. This designation indicates that the gene is a dominant trait and it is the first allele identified. Segregating $F_2$ and $F_{2:3}$ population data suggests that 15A and 11A carry two new independent resistance alleles at different loci (FIGS. 2 and 3). The designations for these alleles are Imi2 for the 11A mutation at the Als2 locus and Imi3 for the second 15A mutation at the Als3 locus.

Identified herein are three independently segregating alleles conferring resistance to imazainox, namely Imi1 (1A, 9A, 10A, 15A and 16A), Imi2 (11A), and Imi3 (15A). It is proposed that each of the three identified alleles are associated with a different structural gene coding for herbicide-insensitive forms of AHAS. Since wheat is a hexaploid, multiple AHAS loci would be expected. Other polyploid species have been found to have more than one copy of AHAS. In Nicotiana tabacum, an allotetraploid, two AHAS genes have been identified and characterized (Mazur et al. 1987). Chaleff and Ray (1984) identified two independently segregating sulfonylurea resistance alleles in *Nicotiana tabacum*, each coding for an altered form of AHAS. *Zea mays* possesses two constitutively expressed identical AHAS genes (Fang et al., 1992 Plant Mol. Biol. 18:1185-1187). In allotetraploid *Brassica napus* and *Gossypium hirsutum*, an AHAS multi-gene family consisting of five and six members, respectively, is present (Rutledge et al., 1991 Mol Gen. Genet. 229:31-40; Grula et al., 1995 Plant Mol. Biol. 28:837-846). Higher levels of resistance to herbicides have been observed in polyploid species when multiple resistance alleles are present. Swanson et al.

(1989 Theor. Appl. Gen. 78:525-530) combined two unique imidazolinone resistance alleles from two homozygous *Brassica napus* lines resulting in progeny with a higher level of resistance than either homozygous line alone. Creason and Chaleff (1988 Theor. Appl. Genet. 76:177-182) identified Nicotiana tabacum plants homozygous for two mutations that conferred resistance to sulfonylureas. Plants homozygous for both mutations were five-fold more resistant to foliar applications of chlorsulfuron than were plants homozygous for each single mutation. The present invention proposes producing increased levels of resistance to an imidazolinone herbicide in wheat by combining any two or all three resistance alleles.

Example 5

Tolerance to Imidazoliizoize Herbicides in Teal11A, Teal15A and Teal11A/15A Hybrid The increased tolerance exhibited by Teal 11A and Teal 15A to 20 grams per hectare of imazamox has been exemplified in previous examples by the ability to distinguish tolerant from susceptible parental and segregant plants in inheritance studies. Teal 11A has been shown to confer similar levels of tolerance to imidazolinone herbicides to that conferred by the FS4 mutation in Fidel in various greenhouse and field comparisons. The similarity in tolerance is also reflected in comparing the in vitro activity of AHAS extracted from tolerant plants. This is possible because the tolerance in Teal 11A, Teal 15A, and FS4 is due to a mutation in the AHAS enzyme rendering it resistant to inhibition by imidazolinone herbicides. FIG. 6 indicates that the activity of AHAS enzyme extracted from Teal 11A and BW755, a line containing FS4, changes similarly as the rate of imazamox increases, and both have a higher percentage of active (resistant) enzyme at the highest concentration of imazamox than does the wild type check, Teal.

The presence of two IMI nucleic acids in Teal 15A provides increased tolerance to imidazolinone herbicides compared to a line such as BW755 carrying only one IMI nucleic acid. This increased tolerance is reflected both in less injury at higher herbicide rates, but in having more uninhibited AHAS enzyme activity. FIG. 7 illustrates that a 10× rate of imazamox (200 g/ha), all treated one gene plants were injured, while no two gene plants were injured. At all concentrations of imazamox in an in vitro assay of AHAS activity (FIG. 6), but particularly at the highest concentrations, Teal15A had a higher percentage of active (resistant) enzyme than did either of the single gene lines, Teal11A and BW755.

Combining three non-allelic genes each conferring tolerance to imidazolinone herbicides results in greater tolerance than with only two non-allelic genes (FIG. 7). At a 30× rate, or 600 g/ha of imazamox, over half of plants sustained no injury in a still-segregating selfed population of Teal15A crossed with Teal11A, while all plants of the homozygous population of Teal15A sustained injury.

We claim:

1. A wheat plant comprising multiple IMI nucleic acids, wherein the nucleic acids are from different genomes; wherein the wheat plant has increased resistance to an imidazolinone herbicide as compared to a wild-type variety of the plant; wherein said wheat plant is a plant of the line TealIMI 15A, or a hyrbid progeny thereof, a representative sample of seed of the line having been deposited under ATCC Patent Deposit Designation Number PTA-3955; wherein a first IMI nucleic acid, of the multiple IMI nucleic acids is a polynucleotide comprising SEQ ID NO:1 or a polynucleotide encoding a polypeptide comprising SEQ ID NO:2.

2. The wheat plant of claim 1, wherein the multiple IMI nucleic acids are selected from the group consisting of an Imi1 nucleic acid, an Imi2 nucleic acid, and an Imi3 nucleic acid.

3. The wheat plant of claim 1, wherein the multiple IMI nucleic acids encode proteins comprising a mutation in a conserved amino acid sequence selected from the group consisting of a Domain A, a Domain B, a Domain C, a Domain D and a Domain E.

4. The wheat plant of claim 3, wherein the conserved amino acid sequence is a Domain E.

5. The wheat plant of claim 4, wherein the mutation results in a serine to asparagine substitution in the IMI protein as compared to a wild-type AHAS protein.

6. The wheat plant of claim 1, wherein a second IMI nucleic acid of the multiple nucleic acids is selected from the group consisting of:
  i) polynucleotides comprising SEQ ID NO:3;
  ii) polynucleotides encoding polypeptides comprising SEQ ID NO:4; and
  iii) polynucleotides encoding IMI polypeptides comprising at least 90% amino acid sequence identity to SEQ ID NO:4, wherein the polypeptides comprise a serine to asparagine substitution in Domain E.

7. The wheat plant of claim 1, wherein one of the IMI nucleic acids comprises a polynucleotide sequence encoding the polypeptide of SEQ ID NO:2.

8. The wheat plant of claim 1, comprising two IMI nucleic acids.

9. The wheat plant of claim 8, comprising an Imi1 nucleic acid and an Imi2 nucleic acid.

10. The wheat plant of claim 9, wherein the Imi1 nucleic acid comprises a polynucleotide sequence encoding the polypeptide of SEQ ID NO:2.

11. The wheat plant of claim 1, comprising three IMI nucleic acids.

12. The wheat plant of any one of claims 1-5, wherein the plant is not transgenic.

13. The wheat plant of claim 1, wherein a second IMI nucleic acid of the multiple nucleic acids comprises the Imi3 gene of TealIMI 15A.

14. A wheat plant comprising multiple IMI nucleic acids, wherein the nucleic acids are from different genomes; wherein the wheat plant has increased resistance to an imidazolinone herbicide as compared to a wild-type variety of the plant; wherein said wheat plant is a hybrid of plants of the lines TealIMI 11A and TealIMI 15A wherein a representative sample of seed of the line TealIMI 15A was deposited under ATCC Patent Deposit Designation Number PTA-3955 and a representative sample of seed of the line TealIMI 11 A was deposited under ATCC Patent Deposit Designation Number PTA-3953; and wherein a first IMI nucleic acid, of the multiple IMI nucleic acids is a polynucleotide comprising SEQ ID NO: 1 or a polynucleotide encoding a polypeptide comprising SEQ ID NO:2.

15. The wheat plant of claim 1, wherein the imidazolinone herbicide is selected from the group consisting of 2-(4-isopropyl-4-methyl-5-oxo-2-imidazolin-2-yl)- nicotinic acid, 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate.

16. The wheat plant of claim 1, wherein the imidazolinone herbicide is 5-ethyl-2-(4-isopropyl-4-methyl-5-oxo-2-imidazolin-2-yl) -nicotinic acid.

17. The wheat plant of claim 1, wherein the imidazolinone herbicide is 2-(4-isopropyl-4-methyl-5-oxo-2-imidazolin-2-yl)-5-(methoxymethyl)-nicotinic acid.

18. A plant part of the wheat plant of claim 1.

19. A plant cell of the wheat plant of claim 1.

20. A wheat plant comprising multiple IMI nucleic acids, wherein the nucleic acids are from different genomes; wherein the wheat plant has increased resistance to an imidazolinone herbicide as compared to a wild-type variety of the plant; wherein said wheat plant is a plant of the line TealIMI 15A, or a hybrid progeny thereof, a representative sample of seed of the line having been deposited under ATCC Patent Deposit Designation Number PTA-3955; wherein a first IMI nucleic acid of the multiple IMI nucleic acids is a polynucleotide comprising SEQ ID NO:1 or a polynucleotide encoding a polypeptide comprising SEQ ID NO:2; and wherein a second IMI nucleic acid of the multiple IMI nucleic acids comprises the Imi3 gene of TealIMI 15A.

21. A plant part of the wheat plant of claim 20.

22. A plant cell of the wheat plant of claim 20.

* * * * *

SEQUENCE LISTING

```
<160> NUMBER OF SEQ ID NOS: 35

<210> SEQ ID NO 1
<211> LENGTH: 1675
<212> TYPE: DNA
<213> ORGANISM: Triticum aestivum
<220> FEATURE:
<221> NAME/KEY: CDS
<222> LOCATION: (2)..(1672)
<220> FEATURE:
<221> NAME/KEY: modified_base
<222> LOCATION: (764)
<223> OTHER INFORMATION: unknown nucleotide
<220> FEATURE:
<221> NAME/KEY: modified_base
<222> LOCATION: (1003)
<223> OTHER INFORMATION: unknown nucleotide
<220> FEATURE:
<221> NAME/KEY: modified_base
<222> LOCATION: (1006)
<223> OTHER INFORMATION: unknown nucleotide

<400> SEQUENCE: 1 c gac gtc ttc gcc tac ccc ggc ggc gcc tcc atg gag atc cac cag gcg      49
  Asp Val Phe Ala Tyr Pro Gly Gly Ala Ser Met Glu Ile His Gln Ala
   1               5                  10                  15 ctg acg cgc tcg ccc gtc atc acc aac cac ctc ttc cgc cac gag cag         97
Leu Thr Arg Ser Pro Val Ile Thr Asn His Leu Phe Arg His Glu Gln
             20                  25                  30 ggg gag gcg ttc gcg gcg tcc ggc tac gcc cgc gcg tcc ggc cgc gtc        145
Gly Glu Ala Phe Ala Ala Ser Gly Tyr Ala Arg Ala Ser Gly Arg Val
         35                  40                  45 ggc gtc tgc gtc gcc acc tcc ggc ccg ggg gcc acc aac ctc gtc tcc        193
Gly Val Cys Val Ala Thr Ser Gly Pro Gly Ala Thr Asn Leu Val Ser
     50                  55                  60 gcg ctc gcc gac gcc ctc ctc gac tcc atc ccc atg gtc gcc atc acg        241
```

```
                Ala Leu Ala Asp Ala Leu Leu Asp Ser Ile Pro Met Val Ala Ile Thr
                 65                  70                  75                  80 ggc cag gtc ccc cgc cgc atg atc ggc acg gac gcg ttc cag gag acg              289
Gly Gln Val Pro Arg Arg Met Ile Gly Thr Asp Ala Phe Gln Glu Thr
                 85                  90                  95 ccc ata gtg gag gtc acg cgc tcc atc acc aag cac aac tac ctg gtc              337
Pro Ile Val Glu Val Thr Arg Ser Ile Thr Lys His Asn Tyr Leu Val
                100                 105                 110 ctt gac gtg gag gat atc ccc cgc gtc atc cag gaa gcc ttc ttc ctt              385
Leu Asp Val Glu Asp Ile Pro Arg Val Ile Gln Glu Ala Phe Phe Leu
                115                 120                 125 gca tcc tct ggc cgc ccg ggg ccg gtg cta gtt gat atc ccc aag gac              433
Ala Ser Ser Gly Arg Pro Gly Pro Val Leu Val Asp Ile Pro Lys Asp
            130                 135                 140 atc cag cag cag atg gct gtg ccc gtc tgg gac act cca atg agt ttg              481
Ile Gln Gln Gln Met Ala Val Pro Val Trp Asp Thr Pro Met Ser Leu
145                 150                 155                 160 cca ggg tac atc gcc cgc ctg ccc aag cca cca tct act gaa tcg ctt              529
Pro Gly Tyr Ile Ala Arg Leu Pro Lys Pro Pro Ser Thr Glu Ser Leu
                165                 170                 175 gag cag gtc ctg cgt ctg gtt ggc gag tca cgg cgc cca att ctg tat              577
Glu Gln Val Leu Arg Leu Val Gly Glu Ser Arg Arg Pro Ile Leu Tyr
                180                 185                 190 gtt ggt ggt ggc tgc gct gcg tct ggc gag gag ttg cgc cgc ttt gtt              625
Val Gly Gly Gly Cys Ala Ala Ser Gly Glu Glu Leu Arg Arg Phe Val
            195                 200                 205 gag ctt act ggg att cca gtt aca act act ctg atg ggc ctt ggc aac              673
Glu Leu Thr Gly Ile Pro Val Thr Thr Thr Leu Met Gly Leu Gly Asn
210                 215                 220 ttc ccc agc gac gac cca ctg tct ctg cgc atg ctt ggg atg cat ggc              721
Phe Pro Ser Asp Asp Pro Leu Ser Leu Arg Met Leu Gly Met His Gly
225                 230                 235                 240 act gtg tat gca aat tat gca gta gat aag gct gac ctg ttg ntc gca              769
Thr Val Tyr Ala Asn Tyr Ala Val Asp Lys Ala Asp Leu Leu Ile Ala
                245                 250                 255 ttt ggt gtg cgg ttt gat gat cgt gtg act ggg aaa atc gag gct ttt              817
Phe Gly Val Arg Phe Asp Asp Arg Val Thr Gly Lys Ile Glu Ala Phe
            260                 265                 270 gca agc agg tcc aag att gng cac att gac att gac cca gct gag att              865
Ala Ser Arg Ser Lys Ile Glu His Ile Asp Ile Asp Pro Ala Glu Ile
            275                 280                 285 ggc aag aac aag cag cca cat gtc tcc att tgt gca gat gtt aan ctt              913
Gly Lys Asn Lys Gln Pro His Val Ser Ile Cys Ala Asp Val Lys Leu
290                 295                 300 gct tta cag ggg ttg aat gat cta tta aat ggg agc aaa gca caa cag              961
Ala Leu Gln Gly Leu Asn Asp Leu Leu Asn Gly Ser Lys Ala Gln Gln
305                 310                 315                 320 ggt ctg gat ttt ggt cca tgg cac aag gag ttg gat cag can aan agg             1009
Gly Leu Asp Phe Gly Pro Trp His Lys Glu Leu Asp Gln Gln Xaa Arg
                325                 330                 335 gag ttt cct cta gga ttc aag act ttt ggc gag gcc atc ccg ccg caa             1057
Glu Phe Pro Leu Gly Phe Lys Thr Phe Gly Glu Ala Ile Pro Pro Gln
                340                 345                 350 tat gct atc cag gta ctg gat gag ctg aca aaa ggg gag gcg atc att             1105
Tyr Ala Ile Gln Val Leu Asp Glu Leu Thr Lys Gly Glu Ala Ile Ile
                355                 360                 365 gcc act ggt gtt ggg cag cac cag atg tgg gcg gct cag tat tac act             1153
Ala Thr Gly Val Gly Gln His Gln Met Trp Ala Ala Gln Tyr Tyr Thr
            370                 375                 380 tac aag cgg cca cgg cag tgg ctg tct tcg tct ggt ttg ggg gca atg             1201
```

```
Tyr Lys Arg Pro Arg Gln Trp Leu Ser Ser Gly Leu Gly Ala Met
385                 390                 395                 400 gga ttt ggg tta cca gct gca gct ggc gct gct gtg gcc aac cca ggt    1249
Gly Phe Gly Leu Pro Ala Ala Ala Gly Ala Ala Val Ala Asn Pro Gly
                    405                 410                 415 gtt aca gtt gtt gac att gat ggt gat ggt agt ttc ctc atg aac att    1297
Val Thr Val Val Asp Ile Asp Gly Asp Gly Ser Phe Leu Met Asn Ile
                420                 425                 430 cag gag ttg gcg ttg atc cgc att gag aac ctc cca gtg aag gtg atg    1345
Gln Glu Leu Ala Leu Ile Arg Ile Glu Asn Leu Pro Val Lys Val Met
            435                 440                 445 ata ttg aac aac cag cat ctg gga atg gtg gtg cag tgg gag gat agg    1393
Ile Leu Asn Asn Gln His Leu Gly Met Val Val Gln Trp Glu Asp Arg
        450                 455                 460 ttt tac aag gcc aat cgg gcg cac aca tac ctt ggc aac cca gaa aat    1441
Phe Tyr Lys Ala Asn Arg Ala His Thr Tyr Leu Gly Asn Pro Glu Asn
465                 470                 475                 480 gag agt gag ata tat cca gat ttt gtg acg att gct aaa gga ttc aac    1489
Glu Ser Glu Ile Tyr Pro Asp Phe Val Thr Ile Ala Lys Gly Phe Asn
                    485                 490                 495 gtt cca gca gtt cga gtg acg aag aag agc gaa gtc act gca gca atc    1537
Val Pro Ala Val Arg Val Thr Lys Lys Ser Glu Val Thr Ala Ala Ile
                500                 505                 510 aag aag atg ctt gag acc cca ggg cca tac ttg ttg gat atc ata gtc    1585
Lys Lys Met Leu Glu Thr Pro Gly Pro Tyr Leu Leu Asp Ile Ile Val
            515                 520                 525 ccg cat cag gag cac gtg ctg cct atg atc cca aac ggt ggt gct ttc    1633
Pro His Gln Glu His Val Leu Pro Met Ile Pro Asn Gly Gly Ala Phe
        530                 535                 540 aag gac atg atc atg gag ggt gat ggc agg acc tcg tac tga            1675
Lys Asp Met Ile Met Glu Gly Asp Gly Arg Thr Ser Tyr
545                 550                 555

<210> SEQ ID NO 2
<211> LENGTH: 557
<212> TYPE: PRT
<213> ORGANISM: Triticum aestivum

<400> SEQUENCE: 2

Asp Val Phe Ala Tyr Pro Gly Gly Ala Ser Met Glu Ile His Gln Ala
1               5                   10                  15

Leu Thr Arg Ser Pro Val Ile Thr Asn His Leu Phe Arg His Glu Gln
                20                  25                  30

Gly Glu Ala Phe Ala Ala Ser Gly Tyr Ala Arg Ala Ser Gly Arg Val
            35                  40                  45

Gly Val Cys Val Ala Thr Ser Gly Pro Gly Ala Thr Asn Leu Val Ser
        50                  55                  60

Ala Leu Ala Asp Ala Leu Leu Asp Ser Ile Pro Met Val Ala Ile Thr
65                  70                  75                  80

Gly Gln Val Pro Arg Arg Met Ile Gly Thr Asp Ala Phe Gln Glu Thr
                85                  90                  95

Pro Ile Val Glu Val Thr Arg Ser Ile Thr Lys His Asn Tyr Leu Val
            100                 105                 110

Leu Asp Val Glu Asp Ile Pro Arg Val Ile Gln Glu Ala Phe Phe Leu
        115                 120                 125

Ala Ser Ser Gly Arg Pro Gly Pro Val Leu Val Asp Ile Pro Lys Asp
    130                 135                 140

Ile Gln Gln Gln Met Ala Val Pro Val Trp Asp Thr Pro Met Ser Leu
145                 150                 155                 160
```

Pro Gly Tyr Ile Ala Arg Leu Pro Lys Pro Ser Thr Glu Ser Leu
            165                 170                 175

Glu Gln Val Leu Arg Leu Val Gly Glu Ser Arg Arg Pro Ile Leu Tyr
        180                 185                 190

Val Gly Gly Cys Ala Ala Ser Gly Glu Glu Leu Arg Arg Phe Val
            195                 200                 205

Glu Leu Thr Gly Ile Pro Val Thr Thr Thr Leu Met Gly Leu Gly Asn
    210                 215                 220

Phe Pro Ser Asp Asp Pro Leu Ser Leu Arg Met Leu Gly Met His Gly
225                 230                 235                 240

Thr Val Tyr Ala Asn Tyr Ala Val Asp Lys Ala Asp Leu Leu Ile Ala
                245                 250                 255

Phe Gly Val Arg Phe Asp Asp Arg Val Thr Gly Lys Ile Glu Ala Phe
            260                 265                 270

Ala Ser Arg Ser Lys Ile Glu His Ile Asp Ile Asp Pro Ala Glu Ile
        275                 280                 285

Gly Lys Asn Lys Gln Pro His Val Ser Ile Cys Ala Asp Val Lys Leu
    290                 295                 300

Ala Leu Gln Gly Leu Asn Asp Leu Leu Asn Gly Ser Lys Ala Gln Gln
305                 310                 315                 320

Gly Leu Asp Phe Gly Pro Trp His Lys Glu Leu Asp Gln Gln Lys Arg
                325                 330                 335

Glu Phe Pro Leu Gly Phe Lys Thr Phe Gly Glu Ala Ile Pro Pro Gln
            340                 345                 350

Tyr Ala Ile Gln Val Leu Asp Glu Leu Thr Lys Gly Glu Ala Ile Ile
        355                 360                 365

Ala Thr Gly Val Gly Gln His Gln Met Trp Ala Ala Gln Tyr Tyr Thr
    370                 375                 380

Tyr Lys Arg Pro Arg Gln Trp Leu Ser Ser Gly Leu Gly Ala Met
385                 390                 395                 400

Gly Phe Gly Leu Pro Ala Ala Gly Ala Ala Val Ala Asn Pro Gly
                405                 410                 415

Val Thr Val Val Asp Ile Asp Gly Asp Gly Ser Phe Leu Met Asn Ile
            420                 425                 430

Gln Glu Leu Ala Leu Ile Arg Ile Glu Asn Leu Pro Val Lys Val Met
        435                 440                 445

Ile Leu Asn Asn Gln His Leu Gly Met Val Val Gln Trp Glu Asp Arg
    450                 455                 460

Phe Tyr Lys Ala Asn Arg Ala His Thr Tyr Leu Gly Asn Pro Glu Asn
465                 470                 475                 480

Glu Ser Glu Ile Tyr Pro Asp Phe Val Thr Ile Ala Lys Gly Phe Asn
                485                 490                 495

Val Pro Ala Val Arg Val Thr Lys Lys Ser Glu Val Thr Ala Ala Ile
            500                 505                 510

Lys Lys Met Leu Glu Thr Pro Gly Pro Tyr Leu Leu Asp Ile Ile Val
        515                 520                 525

Pro His Gln Glu His Val Leu Pro Met Ile Pro Asn Gly Gly Ala Phe
    530                 535                 540

Lys Asp Met Ile Met Glu Gly Asp Gly Arg Thr Ser Tyr
545                 550                 555

<210> SEQ ID NO 3
<211> LENGTH: 1672
<212> TYPE: DNA

<213> ORGANISM: Triticum aestivum
<220> FEATURE:
<221> NAME/KEY: CDS
<222> LOCATION: (2)..(1669)

<400> SEQUENCE: 3

```
c gac gtc ttc gcc tac cct ggc ggc gcg tcc atg gag atc cac cag gcg        49
  Asp Val Phe Ala Tyr Pro Gly Gly Ala Ser Met Glu Ile His Gln Ala
    1               5                  10                  15 ctg acg cgc tcg cca gtc atc acc aac cac ctc ttc cgc cac gag cag          97
Leu Thr Arg Ser Pro Val Ile Thr Asn His Leu Phe Arg His Glu Gln
             20                  25                  30 ggg gag gcg ttc gcg gcg tcc ggg tac gcc cgc gcg tcc ggc cgc gtc         145
Gly Glu Ala Phe Ala Ala Ser Gly Tyr Ala Arg Ala Ser Gly Arg Val
         35                  40                  45 ggc gtc tgc gtc gcc acc tcc ggc ccg ggg gcc acc aac ctc gtc tcc         193
Gly Val Cys Val Ala Thr Ser Gly Pro Gly Ala Thr Asn Leu Val Ser
 50                  55                  60 gcg ctc gcc gac gct ctc ctc gac tcc atc ccc atg gtc gcc atc acg         241
Ala Leu Ala Asp Ala Leu Leu Asp Ser Ile Pro Met Val Ala Ile Thr
 65                  70                  75                  80 ggc cag gtc ccc cgc cgc atg atc ggc acg gat gcg ttc cag gag acg         289
Gly Gln Val Pro Arg Arg Met Ile Gly Thr Asp Ala Phe Gln Glu Thr
                 85                  90                  95 ccc atc gtg gag gtc acg cgc tcc atc acc aag cac aac tac ctg gtc         337
Pro Ile Val Glu Val Thr Arg Ser Ile Thr Lys His Asn Tyr Leu Val
            100                 105                 110 ctt gac gtg gag gat atc ccc cgc gtc atc cag gaa gcc ttc ttc ctc         385
Leu Asp Val Glu Asp Ile Pro Arg Val Ile Gln Glu Ala Phe Phe Leu
        115                 120                 125 gca tcc tct ggc cgc ccg ggg ccg gtg ctg gtt gat atc ccc aag gac         433
Ala Ser Ser Gly Arg Pro Gly Pro Val Leu Val Asp Ile Pro Lys Asp
    130                 135                 140 atc cag cag cag atg gct gtg cct gtc tgg gac acg ccg atg agt ttg         481
Ile Gln Gln Gln Met Ala Val Pro Val Trp Asp Thr Pro Met Ser Leu
145                 150                 155                 160 cca ggg tac atc gcc cgc ctg ccc aag cca cca tct act gaa tcg ctt         529
Pro Gly Tyr Ile Ala Arg Leu Pro Lys Pro Pro Ser Thr Glu Ser Leu
                165                 170                 175 gag cag gtc ctg cgt ctg gtt ggc gag tca cgg cgc cca att ctg tat         577
Glu Gln Val Leu Arg Leu Val Gly Glu Ser Arg Arg Pro Ile Leu Tyr
            180                 185                 190 gtt ggt ggt ggc tgc gct gca tct ggt gag gag ttg cgc cgc ttt gtt         625
Val Gly Gly Gly Cys Ala Ala Ser Gly Glu Glu Leu Arg Arg Phe Val
        195                 200                 205 gag ctc act ggg att cca gtt aca act act ctt atg ggc ctt ggc aac         673
Glu Leu Thr Gly Ile Pro Val Thr Thr Thr Leu Met Gly Leu Gly Asn
    210                 215                 220 ttc ccc agt gac gac cca ctg tct ctg cgc atg ctg ggg atg cat ggc         721
Phe Pro Ser Asp Asp Pro Leu Ser Leu Arg Met Leu Gly Met His Gly
225                 230                 235                 240 act gtg tat gca aat tat gca gta gat aag gct gac ctg ttg ctt gca         769
Thr Val Tyr Ala Asn Tyr Ala Val Asp Lys Ala Asp Leu Leu Leu Ala
                245                 250                 255 ttt ggt gtg cgg ttt gat gat cgt gtg acc ggg aaa atc gag gct ttt         817
Phe Gly Val Arg Phe Asp Asp Arg Val Thr Gly Lys Ile Glu Ala Phe
            260                 265                 270 gca agc agg tcc aag att gtg cac att gac att gac cca gct gag att         865
Ala Ser Arg Ser Lys Ile Val His Ile Asp Ile Asp Pro Ala Glu Ile
        275                 280                 285 ggc aag aac aag cag cca cat gtc tcc att tgt gca gat gtt aag ctt         913
```

```
gct tta cag ggg ttg aat gct cta tta aat ggg agc aaa gca caa cag      961
Ala Leu Gln Gly Leu Asn Ala Leu Leu Asn Gly Ser Lys Ala Gln Gln
305                 310                 315                 320 ggt ctg gat ttt ggt cca tgg cac aag gag ttg gat cag cag aag agg     1009
Gly Leu Asp Phe Gly Pro Trp His Lys Glu Leu Asp Gln Gln Lys Arg
                325                 330                 335 gag ttt cct cta gga ttc aag act ttt ggt gag gcc atc ccg ccg caa     1057
Glu Phe Pro Leu Gly Phe Lys Thr Phe Gly Glu Ala Ile Pro Pro Gln
            340                 345                 350 tat gct atc cag gta ctg gat gag ctg aca aaa ggg gag gcg atc att     1105
Tyr Ala Ile Gln Val Leu Asp Glu Leu Thr Lys Gly Glu Ala Ile Ile
        355                 360                 365 gcc acc ggt gtt ggg cag cat cag atg tgg gcg gct cag tat tac act     1153
Ala Thr Gly Val Gly Gln His Gln Met Trp Ala Ala Gln Tyr Tyr Thr
    370                 375                 380 tac aag cgg cca cgg cag tgg ctg tct tca tcc ggt ttg ggt gca atg     1201
Tyr Lys Arg Pro Arg Gln Trp Leu Ser Ser Ser Gly Leu Gly Ala Met
385                 390                 395                 400 gga ttt ggg ttg cca gct gca gct ggc gct gct gtg gcc aac cca ggt     1249
Gly Phe Gly Leu Pro Ala Ala Ala Gly Ala Ala Val Ala Asn Pro Gly
                405                 410                 415 gtt aca gtt gtt gac att gat ggg gat ggt agt ttc ctc atg aac att     1297
Val Thr Val Val Asp Ile Asp Gly Asp Gly Ser Phe Leu Met Asn Ile
            420                 425                 430 cag gag ttg gcg ttg atc cgt att gag aac ctc cca gtg aag gtg atg     1345
Gln Glu Leu Ala Leu Ile Arg Ile Glu Asn Leu Pro Val Lys Val Met
        435                 440                 445 ata ttg aac aac cag cat ctg gga atg gtg gtg cag tgg gag gat agg     1393
Ile Leu Asn Asn Gln His Leu Gly Met Val Val Gln Trp Glu Asp Arg
    450                 455                 460 ttt tac aag gcc aac cgg gcg cac aca tac ctt ggc aac cca gaa aat     1441
Phe Tyr Lys Ala Asn Arg Ala His Thr Tyr Leu Gly Asn Pro Glu Asn
465                 470                 475                 480 gag agt gag ata tat cca gat ttt gtg acg att gct aaa gga ttc aac     1489
Glu Ser Glu Ile Tyr Pro Asp Phe Val Thr Ile Ala Lys Gly Phe Asn
                485                 490                 495 gtt ccg gca gtt cgt gtg acg aag aag agc gaa gtc act gca gca atc     1537
Val Pro Ala Val Arg Val Thr Lys Lys Ser Glu Val Thr Ala Ala Ile
            500                 505                 510 aag aag atg ctt gag acc cca ggg cca tac ttg ttg gat atc att gtc     1585
Lys Lys Met Leu Glu Thr Pro Gly Pro Tyr Leu Leu Asp Ile Ile Val
        515                 520                 525 ccg cat cag gag cac gtg ctg cct atg atc cca aac ggt ggt gct ttt     1633
Pro His Gln Glu His Val Leu Pro Met Ile Pro Asn Gly Gly Ala Phe
    530                 535                 540 aag gac atg atc atg gag ggt gat ggc agg acc tcg tac                 1672
Lys Asp Met Ile Met Glu Gly Asp Gly Arg Thr Ser Tyr
545                 550                 555

<210> SEQ ID NO 4
<211> LENGTH: 556
<212> TYPE: PRT
<213> ORGANISM: Triticum aestivum

<400> SEQUENCE: 4

Asp Val Phe Ala Tyr Pro Gly Gly Ala Ser Met Glu Ile His Gln Ala
 1               5                  10                  15

Leu Thr Arg Ser Pro Val Ile Thr Asn His Leu Phe Arg His Glu Gln
            20                  25                  30
```

(First partial row at top of page:)

```
Gly Lys Asn Lys Gln Pro His Val Ser Ile Cys Ala Asp Val Lys Leu
            290                 295                 300
```

```
Gly Glu Ala Phe Ala Ala Ser Gly Tyr Ala Arg Ala Ser Gly Arg Val
             35                  40                  45

Gly Val Cys Val Ala Thr Ser Gly Pro Gly Ala Thr Asn Leu Val Ser
         50                  55                  60

Ala Leu Ala Asp Ala Leu Leu Asp Ser Ile Pro Met Val Ala Ile Thr
 65                  70                  75                  80

Gly Gln Val Pro Arg Arg Met Ile Gly Thr Asp Ala Phe Gln Glu Thr
                 85                  90                  95

Pro Ile Val Glu Val Thr Arg Ser Ile Thr Lys His Asn Tyr Leu Val
             100                 105                 110

Leu Asp Val Glu Asp Ile Pro Arg Val Ile Gln Glu Ala Phe Phe Leu
             115                 120                 125

Ala Ser Ser Gly Arg Pro Gly Pro Val Leu Val Asp Ile Pro Lys Asp
         130                 135                 140

Ile Gln Gln Gln Met Ala Val Pro Val Trp Asp Thr Pro Met Ser Leu
145                 150                 155                 160

Pro Gly Tyr Ile Ala Arg Leu Pro Lys Pro Pro Ser Thr Glu Ser Leu
                 165                 170                 175

Glu Gln Val Leu Arg Leu Val Gly Glu Ser Arg Arg Pro Ile Leu Tyr
             180                 185                 190

Val Gly Gly Gly Cys Ala Ala Ser Gly Glu Glu Leu Arg Arg Phe Val
         195                 200                 205

Glu Leu Thr Gly Ile Pro Val Thr Thr Thr Leu Met Gly Leu Gly Asn
         210                 215                 220

Phe Pro Ser Asp Asp Pro Leu Ser Leu Arg Met Leu Gly Met His Gly
225                 230                 235                 240

Thr Val Tyr Ala Asn Tyr Ala Val Asp Lys Ala Asp Leu Leu Leu Ala
                 245                 250                 255

Phe Gly Val Arg Phe Asp Asp Arg Val Thr Gly Lys Ile Glu Ala Phe
             260                 265                 270

Ala Ser Arg Ser Lys Ile Val His Ile Asp Ile Asp Pro Ala Glu Ile
         275                 280                 285

Gly Lys Asn Lys Gln Pro His Val Ser Ile Cys Ala Asp Val Lys Leu
         290                 295                 300

Ala Leu Gln Gly Leu Asn Ala Leu Leu Asn Gly Ser Lys Ala Gln Gln
305                 310                 315                 320

Gly Leu Asp Phe Gly Pro Trp His Lys Glu Leu Asp Gln Gln Lys Arg
                 325                 330                 335

Glu Phe Pro Leu Gly Phe Lys Thr Phe Gly Glu Ala Ile Pro Pro Gln
             340                 345                 350

Tyr Ala Ile Gln Val Leu Asp Glu Leu Thr Lys Gly Glu Ala Ile Ile
             355                 360                 365

Ala Thr Gly Val Gly Gln His Gln Met Trp Ala Ala Gln Tyr Tyr Thr
         370                 375                 380

Tyr Lys Arg Pro Arg Gln Trp Leu Ser Ser Ser Gly Leu Gly Ala Met
385                 390                 395                 400

Gly Phe Gly Leu Pro Ala Ala Ala Gly Ala Ala Val Ala Asn Pro Gly
                 405                 410                 415

Val Thr Val Val Asp Ile Asp Gly Asp Gly Ser Phe Leu Met Asn Ile
             420                 425                 430

Gln Glu Leu Ala Leu Ile Arg Ile Glu Asn Leu Pro Val Lys Val Met
             435                 440                 445

Ile Leu Asn Asn Gln His Leu Gly Met Val Val Gln Trp Glu Asp Arg
```

```
                450              455              460
Phe Tyr Lys Ala Asn Arg Ala His Thr Tyr Leu Gly Asn Pro Glu Asn
465              470              475              480

Glu Ser Glu Ile Tyr Pro Asp Phe Val Thr Ile Ala Lys Gly Phe Asn
                 485              490              495

Val Pro Ala Val Arg Val Thr Lys Lys Ser Glu Val Thr Ala Ala Ile
             500              505              510

Lys Lys Met Leu Glu Thr Pro Gly Pro Tyr Leu Leu Asp Ile Ile Val
         515              520              525

Pro His Gln Glu His Val Leu Pro Met Ile Pro Asn Gly Gly Ala Phe
     530              535              540

Lys Asp Met Ile Met Glu Gly Asp Gly Arg Thr Ser
545              550              555

<210> SEQ ID NO 5
<211> LENGTH: 1524
<212> TYPE: DNA
<213> ORGANISM: Triticum aestivum

<400> SEQUENCE: 5
gtctgcgtcg ccacctccgg cccgggggcc accaacctcg tctccgcgct cgccgacgcc      60
ctcctcgact ccatccccat ggtcgccatc acgggccagg tccccgccg catgatcggc      120 acggacgcgt tccaggagac gcccatagtg gaggtcacgc gctccatcac caagcacaac      180
tacctggtcc ttgacgtgga ggatatcccc cgcgtcatcc aggaagcctt cttccttgca      240
tcctctggcc gccgggggcc ggtgctagtt gatatcccca ggacatcca gcagcagatg      300 gctgtgcccg tctgggacac tccaatgagt ttgccagggt acatcgcccg cctgcccaag      360
ccaccatcta ctgaatcgct tgagcaggtc ctgcgtctgg ttggcgagtc acggcgccca      420
attctgtatg ttggtggtgg ctgcgctgcg tctggcgagg agttgcgccg ctttgttgag      480
cttactggga ttccagttac aactactctg atgggccttg caacttccc cagcgacgac      540 ccactgtctc tgcgcatgct tgggatgcat ggcactgtgt atgcaaatta tgcagtagat      600
aaggctgacc tgttgctcgc atttggtgtg cggtttgatg atcgtgtgac tgggaaaatc      660
gaggcttttg caagcaggtc caagattgtg cacattgaca ttgacccagc tgagattggc      720
aagaacaagc agccacatgt ctccatttgt gcagatgtta agcttgcttt acaggggttg      780
aatgatctat taaatgggag caaagcacaa cagggtctgg attttggtcc atggcacaag      840
gagttggatc agcagaagag ggagtttcct ctaggattca agacttttgg cgaggccatc      900
ccgccgcaat atgctatcca ggtactggat gagctgacaa aggggaggc gatcattgcc      960 actggtgttg gcagcaccaa gatgtgggcg gctcagtatt acacttacaa gcggccacgg     1020
cagtggctgt cttcgtctgg tttgggggca atgggatttg ggttaccagc tgcagctggc     1080
gctgctgtgg ccaacccagg tgttacagtt gttgacattg atggtgatgg tagttttcctc    1140 atgaacattc aggagttggc gttgatccgc attgagaacc tcccagtgaa ggtgatgata     1200
ttgaacaacc agcatctggg aatggtggtg cagtgggagg ataggtttta caaggccaat     1260
cgggcgcaca catacctcgg caacccagaa atgagagtg agatatatcc agattttgtg     1320
acgattgcta aaggattcaa cgttccagca gttcgagtga cgaagaagag cgaagtcact     1380
gcagcaatca agaagatgct tgagacccca gggccatact tgttggatat catagtcccg     1440
catcaggagc acgtgctgcc tatgatccca agcggtggtg ctttcaagga catgatcatg     1500
gagggtgatg gcaggaccct cgtac                                           1524
```

<210> SEQ ID NO 6
<211> LENGTH: 1524
<212> TYPE: DNA
<213> ORGANISM: Triticum aestivum

<400> SEQUENCE: 6

| | | | | | |
|---|---|---|---|---|---|
| gtctgcgtcg | ccacctccgg | cccgggggcc | accaacctcg | tctccgcgct | cgccgacgct | 60 |
| ctcctcgact | ccatccccat | ggtcgccatc | acgggccagg | tccccgccg | catgatcggc | 120 |
| acggatgcgt | tccaggagac | gcccatcgtg | gaggtcacgc | gctccatcac | caagcacaac | 180 |
| tacctggtcc | ttgacgtgga | ggatatcccc | cgcgtcatcc | aggaagcctt | cttcctcgca | 240 |
| tcctctggcc | gcccggggcc | ggtgctggtt | gatatcccca | aggacatcca | gcagcagatg | 300 |
| gctgtgcctg | tctgggacac | gccgatgagt | ttgccagggt | acatcgcccg | cctgcccaag | 360 |
| ccaccatcta | ctgaatcgct | tgagcaggtc | ctgcgtctgg | ttggcgagtc | acggcgccca | 420 |
| attctgtatg | ttggtggtgg | ctgcgctgca | tctggtgagg | agttgcgccg | ctttgttgag | 480 |
| ctcactggga | ttccagttac | aactactctt | atgggccttg | gcaacttccc | cagtgacgac | 540 |
| ccactgtctc | tgcgcatgct | ggggatgcat | ggcactgtgt | atgcaaatta | tgcagtagat | 600 |
| aaggctgacc | tgttgcttgc | atttggtgtg | cggtttgatg | atcgtgtgac | cgggaaaatc | 660 |
| gaggcttttg | caagcaggtc | caagattgtg | cacattgaca | ttgacccagc | tgagattggc | 720 |
| aagaacaagc | agccacatgt | ctccatttgt | gcagatgtta | agcttgcttt | acaggggttg | 780 |
| aatgctctat | taaatgggag | caaagcacaa | caggtctgg | attttggtcc | atggcacaag | 840 |
| gagttggatc | agcagaagag | ggagtttcct | ctaggattca | agacttttgg | tgaggccatc | 900 |
| ccgccgcaat | atgctatcca | ggtactggat | gagctgacaa | aaggggaggc | gatcattgcc | 960 |
| accggtgttg | gcagcatca | gatgtgggcg | gctcagtatt | acacttacaa | gcggccacgg | 1020 |
| cagtggctgt | cttcatccgg | tttggtgca | atgggatttg | ggttgccagc | tgcagctggc | 1080 |
| gctgctgtgg | ccaacccagg | tgttacagtt | gttgacatta | tggggatgg | tagtttcctc | 1140 |
| atgaacattc | aggagttggc | gttgatccgt | attgagaacc | tcccagtgaa | ggtgatgata | 1200 |
| ttgaacaacc | agcatctggg | aatggtggtg | cagtgggagg | ataggtttta | caaggccaac | 1260 |
| cgggcgcaca | cataccttgg | caacccagaa | aatgagagtg | agatatatcc | agattttgtg | 1320 |
| acgattgcta | aaggattcaa | cgttccggca | gttcgtgtga | cgaagaagag | cgaagtcact | 1380 |
| gcagcaatca | agaagatgct | tgagacccca | gggccatact | tgttggatat | cattgtcccg | 1440 |
| catcaggagc | acgtgctgcc | tatgatccca | agcggtggtg | cttttaagga | catgatcatg | 1500 |
| gagggtgatg | gcaggacctc | gtac | | | | 1524 |

<210> SEQ ID NO 7
<211> LENGTH: 1524
<212> TYPE: DNA
<213> ORGANISM: Triticum aestivum

<400> SEQUENCE: 7

| | | | | | |
|---|---|---|---|---|---|
| gtctgcgtcg | ccacctccgg | cccgggggcc | accaacctcg | tctccgcgct | cgctgacgcc | 60 |
| ctcctcgact | ccatccccat | ggtcgccatc | acgggccagg | tccccgccg | catgatcggc | 120 |
| acggacgcgt | tccaggagac | gcccatagtg | gaggtcacgc | gctccatcac | caagcacaac | 180 |
| tacctggtcc | ttgacgtgga | ggatatcccc | cgcgtcatcc | aggaagcctt | cttcctcgcg | 240 |
| tcctctggcc | gcccggggcc | ggtgctggtt | gatatcccca | aggatatcca | gcagcagatg | 300 |
| gccgtgccta | tctgggacac | gccgatgagt | ttgccagggt | acatcgcccg | cctgcccaag | 360 |

-continued

```
ccaccatcta ctgaatcgct tgagcaggtc ctgcgtctgg ttggcgagtc acggcgccca     420
attctgtatg ttggtggtgg ctgcgctgca tccggcgagg agttgcgccg ctttgttgag     480
ctcactggga ttccggttac aactactctg atgggccttg caacttccc cagcgacgac      540
ccactgtctc tgcgcatgct tgggatgcat ggcactgtgt atgcaaatta tgcagtcgat     600
aaggctgacc tgttgcttgc atttggtgtg cggtttgatg atcgcgtgac tgggaaaatc     660
gaggccttg caagcaggtc caagattgtg cacattgaca ttgacccagc tgagattggc      720
aagaacaagc agccacatgt ctccatttgt gcagatgtta agcttgcttt acaggggttg     780
aatgctctat taaatgggag caaagcacaa caggtctgg atttggtcc atggcacaag       840
gagttggatc agcagaagag ggagtttcct ctaggattca agacttttgg cgaggccatc     900
ccgccgcaat atgctatcca ggtactggat gagctgacaa aagggaggc gatcattgct      960
actggtgttg gcagcacca gatgtgggcg gctcagtatt acacttacaa gcggccacgg    1020
cagtggctgt cttcgtctgg tttgggggca atggggatttg ggttaccagc tgcagctggc   1080
gctgctgtgg ccaacccagg tgttacagtt gttgacattg atggagatgg tagtttcctc   1140
atgaacattc aggagttggc attgatccgt attgagaacc tccctgtgaa ggtgatgata   1200
ttgaacaacc agcatctggg aatggtggtg caatgggagg ataggtttta caaggccaat   1260
cgggcgcaca catacctggg caacccagaa aatgagagtg agatatatcc agattttgtg   1320
acgattgcta aaggattcaa cgttccggca gttcgtgtga cgaagaagag cgaagtcact   1380
gcagcaatca gaagatgct tgagacccca gggccatact tgttggatat catcgtcccg    1440
catcaggagc acgtgctgcc tatgatccca agcggtggtg ctttcaagga catgatcatg   1500
gagggtgatg gcaggacctc gtac                                            1524
```

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 8

Ala Ile Thr Gly Gln Val Pro Arg Arg Met Ile Gly Thr
 1               5                  10

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 9

Gln Trp Glu Asp
 1

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 10

Val Phe Ala Tyr Pro Gly Gly Ala Ser Met Glu Ile His Gln Ala Leu

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 11

Ala Phe Gln Glu Thr Pro
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 12

Ile Pro Ser Gly Gly
 1               5

<210> SEQ ID NO 13
<211> LENGTH: 1935
<212> TYPE: DNA
<213> ORGANISM: Oryza sp.
<220> FEATURE:
<221> NAME/KEY: CDS
<222> LOCATION: (1)..(1932)

<400> SEQUENCE: 13

```
atg gct acg acc gcc gcg gcc gcg gcc gcc ctg tcc gcc gcc gcg       48
Met Ala Thr Thr Ala Ala Ala Ala Ala Ala Leu Ser Ala Ala Ala
 1               5                  10                  15 acg gcc aag acc ggc cgt aag aac cac cag cga cac cac gtc ctt ccc   96
Thr Ala Lys Thr Gly Arg Lys Asn His Gln Arg His His Val Leu Pro
                 20                  25                  30 gct cga ggc cgg gtg ggg gcg gcg gcg gtc agg tgc tcg gcg gtg tcc  144
Ala Arg Gly Arg Val Gly Ala Ala Ala Val Arg Cys Ser Ala Val Ser
             35                  40                  45 ccg gtc acc ccg ccg tcc ccg gcg ccg ccg gcc acg ccg ctc cgg ccg  192
Pro Val Thr Pro Pro Ser Pro Ala Pro Pro Ala Thr Pro Leu Arg Pro
         50                  55                  60 tgg ggg ccg gcc gag ccc cgc aag ggc gcg gac atc ctc gtg gag gcg  240
Trp Gly Pro Ala Glu Pro Arg Lys Gly Ala Asp Ile Leu Val Glu Ala
 65                  70                  75                  80 ctg gag cgg tgc ggc gtc agc gac gtg ttc gcc tac ccg ggc ggc gcg  288
Leu Glu Arg Cys Gly Val Ser Asp Val Phe Ala Tyr Pro Gly Gly Ala
                 85                  90                  95 tcc atg gag atc cac cag gcg ctg acg cgc tcc ccg gtc atc acc aac  336
Ser Met Glu Ile His Gln Ala Leu Thr Arg Ser Pro Val Ile Thr Asn
                100                 105                 110 cac ctc ttc cgc cac gag cag ggc gag gcg ttc gcg gcg tcc ggg tac  384
His Leu Phe Arg His Glu Gln Gly Glu Ala Phe Ala Ala Ser Gly Tyr
             115                 120                 125 gcg cgc gcg tcc ggc cgc gtc ggg gtc tgc gtc gcc acc tcc ggc ccc  432
Ala Arg Ala Ser Gly Arg Val Gly Val Cys Val Ala Thr Ser Gly Pro
         130                 135                 140 ggg gca acc aac ctc gtg tcc gcg ctc gcc gac gcg ctg ctc gac tcc  480
```

```
Gly Ala Thr Asn Leu Val Ser Ala Leu Ala Asp Ala Leu Leu Asp Ser
145                 150                 155                 160 gtc ccg atg gtc gcc atc acg ggc cag gtc ccc cgc cgc atg atc ggc      528
Val Pro Met Val Ala Ile Thr Gly Gln Val Pro Arg Arg Met Ile Gly
                    165                 170                 175 acc gac gcc ttc cag gag acg ccc ata gtc gag gtc acc cgc tcc atc      576
Thr Asp Ala Phe Gln Glu Thr Pro Ile Val Glu Val Thr Arg Ser Ile
                180                 185                 190 acc aag cac aat tac ctt gtc ctt gat gtg gag gac atc ccc cgc gtc      624
Thr Lys His Asn Tyr Leu Val Leu Asp Val Glu Asp Ile Pro Arg Val
            195                 200                 205 ata cag gaa gcc ttc ttc ctc gcg tcc tcg ggc cgt cct ggc ccg gtg      672
Ile Gln Glu Ala Phe Phe Leu Ala Ser Ser Gly Arg Pro Gly Pro Val
210                 215                 220 ctg gtc gac atc ccc aag gac atc cag cag cag atg gcc gtg ccg gtc      720
Leu Val Asp Ile Pro Lys Asp Ile Gln Gln Gln Met Ala Val Pro Val
225                 230                 235                 240 tgg gac acc tcg atg aat cta cca ggg tac atc gca cgc ctg ccc aag      768
Trp Asp Thr Ser Met Asn Leu Pro Gly Tyr Ile Ala Arg Leu Pro Lys
                245                 250                 255 cca ccc gcg aca gaa ttg ctt gag cag gtc ttg cgt ctg gtt ggc gag      816
Pro Pro Ala Thr Glu Leu Leu Glu Gln Val Leu Arg Leu Val Gly Glu
                260                 265                 270 tca cgg cgc ccg att ctc tat gtc ggt ggt ggc tgc tct gca tct ggt      864
Ser Arg Arg Pro Ile Leu Tyr Val Gly Gly Gly Cys Ser Ala Ser Gly
                275                 280                 285 gac gaa ttg cgc tgg ttt gtt gag ctg act ggt atc cca gtt aca acc      912
Asp Glu Leu Arg Trp Phe Val Glu Leu Thr Gly Ile Pro Val Thr Thr
290                 295                 300 act ctg atg ggc ctc ggc aat ttc ccc agt gac gac ccg ttg tcc ctg      960
Thr Leu Met Gly Leu Gly Asn Phe Pro Ser Asp Asp Pro Leu Ser Leu
305                 310                 315                 320 cgc atg ctt ggg atg cat ggc acg gta tac gca aat tat gcc gtg gat     1008
Arg Met Leu Gly Met His Gly Thr Val Tyr Ala Asn Tyr Ala Val Asp
                325                 330                 335 aag gct gac ctg ttg ctt gcg ttt ggt gtg cgg ttt gat gat cgt gtg     1056
Lys Ala Asp Leu Leu Leu Ala Phe Gly Val Arg Phe Asp Asp Arg Val
                340                 345                 350 aca ggg aaa att gag gct ttt gca agc agg gcc aag att gtg cac att     1104
Thr Gly Lys Ile Glu Ala Phe Ala Ser Arg Ala Lys Ile Val His Ile
            355                 360                 365 gac att gat cca gca gag att gga aag aac aag caa cca cat gtg tca     1152
Asp Ile Asp Pro Ala Glu Ile Gly Lys Asn Lys Gln Pro His Val Ser
370                 375                 380 att tgc gca gat gtt aag ctt gct tta cag ggc ttg aat gct ctg cta     1200
Ile Cys Ala Asp Val Lys Leu Ala Leu Gln Gly Leu Asn Ala Leu Leu
385                 390                 395                 400 caa cag agc aca aca aag aca agt tct gat ttt agt gca tgg cac aat     1248
Gln Gln Ser Thr Thr Lys Thr Ser Ser Asp Phe Ser Ala Trp His Asn
                405                 410                 415 gag ttg gac cag cag aag agg gag ttt cct ctg ggg tac aaa act ttt     1296
Glu Leu Asp Gln Gln Lys Arg Glu Phe Pro Leu Gly Tyr Lys Thr Phe
                420                 425                 430 ggt gaa gag atc cca ccg caa tat gcc att cag gtg ctg gat gag ctg     1344
Gly Glu Glu Ile Pro Pro Gln Tyr Ala Ile Gln Val Leu Asp Glu Leu
            435                 440                 445 acg aaa ggt gag gca atc atc gct act ggt gtt ggg cag cac cag atg     1392
Thr Lys Gly Glu Ala Ile Ile Ala Thr Gly Val Gly Gln His Gln Met
450                 455                 460 tgg gcg gca caa tat tac acc tac aag cgg cca cgg cag tgg ctg tct     1440
```

```
Trp Ala Ala Gln Tyr Tyr Thr Tyr Lys Arg Pro Arg Gln Trp Leu Ser
465                 470                 475                 480 tcg gct ggt ctg ggc gca atg gga ttt ggg ctg cct gct gca gct ggt        1488
Ser Ala Gly Leu Gly Ala Met Gly Phe Gly Leu Pro Ala Ala Ala Gly
                485                 490                 495 gct tct gtg gct aac cca ggt gtc aca gtt gtt gat att gat ggg gat        1536
Ala Ser Val Ala Asn Pro Gly Val Thr Val Val Asp Ile Asp Gly Asp
            500                 505                 510 ggt agc ttc ctc atg aac att cag gag ctg gca ttg atc cgc att gag        1584
Gly Ser Phe Leu Met Asn Ile Gln Glu Leu Ala Leu Ile Arg Ile Glu
        515                 520                 525 aac ctc cct gtg aag gtg atg gtg ttg aac aac caa cat ttg ggt atg        1632
Asn Leu Pro Val Lys Val Met Val Leu Asn Asn Gln His Leu Gly Met
    530                 535                 540 gtg gtg caa tgg gag gat agg ttt tac aag gcg aat agg gcg cat aca        1680
Val Val Gln Trp Glu Asp Arg Phe Tyr Lys Ala Asn Arg Ala His Thr
545                 550                 555                 560 tac ttg ggc aac ccg gaa tgt gag agc gag ata tat cca gat ttt gtg        1728
Tyr Leu Gly Asn Pro Glu Cys Glu Ser Glu Ile Tyr Pro Asp Phe Val
                565                 570                 575 act att gct aag ggg ttc aat att cct gca gtc cgt gta aca aag aag        1776
Thr Ile Ala Lys Gly Phe Asn Ile Pro Ala Val Arg Val Thr Lys Lys
            580                 585                 590 agt gaa gtc cgt gcc gcc atc aag aag atg ctc gag act cca ggg cca        1824
Ser Glu Val Arg Ala Ala Ile Lys Lys Met Leu Glu Thr Pro Gly Pro
        595                 600                 605 tac ttg ttg gat atc atc gtc ccg cac cag gag cat gtg ctg cct atg        1872
Tyr Leu Leu Asp Ile Ile Val Pro His Gln Glu His Val Leu Pro Met
    610                 615                 620 atc cca agt ggg ggc gca ttc aag gac atg atc ctg gat ggt gat ggc        1920
Ile Pro Ser Gly Gly Ala Phe Lys Asp Met Ile Leu Asp Gly Asp Gly
625                 630                 635                 640 agg act gtg tat taa                                                     1935
Arg Thr Val Tyr <210> SEQ ID NO 14
<211> LENGTH: 644
<212> TYPE: PRT
<213> ORGANISM: Oryza sp.

<400> SEQUENCE: 14

Met Ala Thr Thr Ala Ala Ala Ala Ala Ala Leu Ser Ala Ala
 1               5                  10                  15

Thr Ala Lys Thr Gly Arg Lys Asn His Gln Arg His His Val Leu Pro
                20                  25                  30

Ala Arg Gly Arg Val Gly Ala Ala Val Arg Cys Ser Ala Val Ser
            35                  40                  45

Pro Val Thr Pro Pro Ser Pro Ala Pro Pro Ala Thr Pro Leu Arg Pro
        50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
                100                 105                 110

His Leu Phe Arg His Glu Gln Gly Glu Ala Phe Ala Ala Ser Gly Tyr
            115                 120                 125

Ala Arg Ala Ser Gly Arg Val Gly Val Cys Val Ala Thr Ser Gly Pro
        130                 135                 140
```

```
Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Cys Ser Ala Ser Gly
        275                 280                 285

Asp Glu Leu Arg Trp Phe Val Glu Leu Thr Gly Ile Pro Val Thr Thr
    290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
    370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
    450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
        515                 520                 525

Asn Leu Pro Val Lys Val Met Val Leu Asn Asn Gln His Leu Gly Met
    530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
```

```
                  565                 570                 575
Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
    610                 615                 620

Ile Pro Ser Gly Gly Ala Phe Lys Asp Met Ile Leu Asp Gly Asp Gly
625                 630                 635                 640

Arg Thr Val Tyr

<210> SEQ ID NO 15
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (681)
<223> OTHER INFORMATION: unknown nucleotide

<400> SEQUENCE: 15 gtc gac gtc ttc gcc tac ccc ggc ggc gcc tcc atg gag atc cac cag       48
Val Asp Val Phe Ala Tyr Pro Gly Gly Ala Ser Met Glu Ile His Gln
  1               5                  10                  15 gcg ctg acg cgc tcg ccc gtc atc acc aac cac ctc ttc cgc cac gag       96
Ala Leu Thr Arg Ser Pro Val Ile Thr Asn His Leu Phe Arg His Glu
             20                  25                  30 cag ggg gag gcg ttc gcg gcg tcc ggc tac gcc cgc gcg tcc ggc cgc      144
Gln Gly Glu Ala Phe Ala Ala Ser Gly Tyr Ala Arg Ala Ser Gly Arg
         35                  40                  45 gtc ggc gtc tgc gtc gcc acc tcc ggc ccg ggg gcc acc aac ctc gtc      192
Val Gly Val Cys Val Ala Thr Ser Gly Pro Gly Ala Thr Asn Leu Val
     50                  55                  60 tcc gcg ctc gcc gac gcc ctc ctc gac tcc atc ccc atg gtc gcc atc      240
Ser Ala Leu Ala Asp Ala Leu Leu Asp Ser Ile Pro Met Val Ala Ile
 65                  70                  75                  80 acg ggc cag gtc ccc cgc cgc atg atc ggc acg gac gcg ttc cag gag      288
Thr Gly Gln Val Pro Arg Arg Met Ile Gly Thr Asp Ala Phe Gln Glu
                 85                  90                  95 acg ccc ata gtg gag gtc acg cgc tcc atc acc aag cac aac tac ctg      336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc      384
Val Leu Asp Val Glu Asp Ile Pro Arg Val Ile Gln Glu Ala Phe Phe
        115                 120                 125 ctt gca tcc tct ggc cgc ccg ggg ccg gtg cta gtt gat atc ccc aag      432
Leu Ala Ser Ser Gly Arg Pro Gly Pro Val Leu Val Asp Ile Pro Lys
    130                 135                 140 gac atc cag cag cag atg gct gtg ccc gtc tgg gac act cca atg agt      480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg      528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg      576
Leu Glu Gln Val Leu Arg Leu Val Gly Glu Ser Arg Arg Pro Ile Leu
            180                 185                 190 tat gtt ggt ggt ggc tgc gct gcg tct ggc gag gag ttg cgc cgc ttt      624
```

-continued

```
Tyr Val Gly Gly Cys Ala Ala Ser Gly Glu Glu Leu Arg Arg Phe
        195                 200                 205 gtt gag ctt act ggg att cca gtt aca act act ctg atg ggc ctt ggc      672
Val Glu Leu Thr Gly Ile Pro Val Thr Thr Thr Leu Met Gly Leu Gly
    210                 215                 220 aac ttc ccn agc gac gac cca ctg tct ctg cgc atg ctt ggg atg cat      720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ctc      768
Gly Thr Val Tyr Ala Asn Tyr Ala Val Asp Lys Ala Asp Leu Leu Leu
                245                 250                 255 gca ttt ggt gtg cgg ttt gat gat cgt gtg act ggg aaa atc gag gct      816
Ala Phe Gly Val Arg Phe Asp Asp Arg Val Thr Gly Lys Ile Glu Ala
            260                 265                 270 ttt gca agc agg tcc aag att gtg cac att gac att gac cca gct gag      864
Phe Ala Ser Arg Ser Lys Ile Val His Ile Asp Ile Asp Pro Ala Glu
        275                 280                 285 att ggc aag aac aag cag cca cat gtc tcc att tgt gca gat gtt aag      912
Ile Gly Lys Asn Lys Gln Pro His Val Ser Ile Cys Ala Asp Val Lys
    290                 295                 300 ctt gct tta cag ggg ttg aat gat cta tta aat ggg agc aaa gca caa      960
Leu Ala Leu Gln Gly Leu Asn Asp Leu Leu Asn Gly Ser Lys Ala Gln
305                 310                 315                 320 cag ggt ctg gat ttt ggt cca tgg cac aag gag ttg gat cag cag aag     1008
Gln Gly Leu Asp Phe Gly Pro Trp His Lys Glu Leu Asp Gln Gln Lys
                325                 330                 335 agg gag ttt cct cta gga ttc aag act ttt ggc gag gcc atc ccg ccg     1056
Arg Glu Phe Pro Leu Gly Phe Lys Thr Phe Gly Glu Ala Ile Pro Pro
            340                 345                 350 caa tat gct atc cag gta ctg gat gag ctg aca aaa ggg gag gcg atc     1104
Gln Tyr Ala Ile Gln Val Leu Asp Glu Leu Thr Lys Gly Glu Ala Ile
        355                 360                 365 att gcc act ggt gtt ggg cag cac cag atg tgg gcg gct cag tat tac     1152
Ile Ala Thr Gly Val Gly Gln His Gln Met Trp Ala Ala Gln Tyr Tyr
    370                 375                 380 act tac aag cgg cca cgg cag tgg ctg tct tcg tct ggt ttg ggg gca     1200
Thr Tyr Lys Arg Pro Arg Gln Trp Leu Ser Ser Ser Gly Leu Gly Ala
385                 390                 395                 400 atg gga ttt ggg tta cca gct gca gct ggc gct gct gtg gcc aac cca     1248
Met Gly Phe Gly Leu Pro Ala Ala Ala Gly Ala Ala Val Ala Asn Pro
                405                 410                 415 ggt gtt aca gtt gtt gac att gat ggt gat ggt agt ttc ctc atg aac     1296
Gly Val Thr Val Val Asp Ile Asp Gly Asp Gly Ser Phe Leu Met Asn
            420                 425                 430 att cag gag ttg gcg ttg atc cgc att gag aac ctc cca gtg aag gtg     1344
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat     1392
Met Ile Leu Asn Asn Gln His Leu Gly Met Val Val Gln Trp Glu Asp
    450                 455                 460 agg ttt tac aag gcc aat cgg gcg cac aca tac ctt ggc aac cca gaa     1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc     1488
Asn Glu Ser Glu Ile Tyr Pro Asp Phe Val Thr Ile Ala Lys Gly Phe
                485                 490                 495 aac gtt cca gca gtt cga gtg acg aag aag agc gaa gtc act gca gca     1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc ata     1584
```

-continued

```
Ile Lys Lys Met Leu Glu Thr Pro Gly Pro Tyr Leu Leu Asp Ile Ile
        515                 520                 525 gtc ccg cat cag gag cac gtg ctg cct atg atc cca agc ggt ggt gct    1632
Val Pro His Gln Glu His Val Leu Pro Met Ile Pro Ser Gly Gly Ala
        530                 535                 540 ttc aag gac atg atc atg gag ggt gat ggc agg acc tcg tac            1674
Phe Lys Asp Met Ile Met Glu Gly Asp Gly Arg Thr Ser
545                 550                 555
```

<210> SEQ ID NO 16
<211> LENGTH: 557
<212> TYPE: PRT
<213> ORGANISM: Triticum aestivum

<400> SEQUENCE: 16

```
Val Asp Val Phe Ala Tyr Pro Gly Gly Ala Ser Met Glu Ile His Gln
  1               5                  10                  15

Ala Leu Thr Arg Ser Pro Val Ile Thr Asn His Leu Phe Arg His Glu
             20                  25                  30

Gln Gly Glu Ala Phe Ala Ala Ser Gly Tyr Ala Arg Ala Ser Gly Arg
         35                  40                  45

Val Gly Val Cys Val Ala Thr Ser Gly Pro Gly Ala Thr Asn Leu Val
     50                  55                  60

Ser Ala Leu Ala Asp Ala Leu Leu Asp Ser Ile Pro Met Val Ala Ile
 65                  70                  75                  80

Thr Gly Gln Val Pro Arg Arg Met Ile Gly Thr Asp Ala Phe Gln Glu
                 85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
            180                 185                 190

Tyr Val Gly Gly Gly Cys Ala Ala Ser Gly Glu Glu Leu Arg Arg Phe
        195                 200                 205

Val Glu Leu Thr Gly Ile Pro Val Thr Thr Thr Leu Met Gly Leu Gly
    210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Leu
                245                 250                 255

Ala Phe Gly Val Arg Phe Asp Asp Arg Val Thr Gly Lys Ile Glu Ala
            260                 265                 270

Phe Ala Ser Arg Ser Lys Ile Val His Ile Asp Ile Asp Pro Ala Glu
        275                 280                 285

Ile Gly Lys Asn Lys Gln Pro His Val Ser Ile Cys Ala Asp Val Lys
    290                 295                 300

Leu Ala Leu Gln Gly Leu Asn Asp Leu Leu Asn Gly Ser Lys Ala Gln
305                 310                 315                 320

Gln Gly Leu Asp Phe Gly Pro Trp His Lys Glu Leu Asp Gln Gln Lys
```

```
                    325                 330                 335
Arg Glu Phe Pro Leu Gly Phe Lys Thr Phe Gly Glu Ala Ile Pro Pro
                340                 345                 350

Gln Tyr Ala Ile Gln Val Leu Asp Glu Leu Thr Lys Gly Glu Ala Ile
            355                 360                 365

Ile Ala Thr Gly Val Gly Gln His Gln Met Trp Ala Ala Gln Tyr Tyr
        370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Ala Gly Ala Ala Val Ala Asn Pro
                405                 410                 415

Gly Val Thr Val Val Asp Ile Asp Gly Asp Gly Ser Phe Leu Met Asn
                420                 425                 430

Ile Gln Glu Leu Ala Leu Ile Arg Ile Glu Asn Leu Pro Val Lys Val
            435                 440                 445

Met Ile Leu Asn Asn Gln His Leu Gly Met Val Val Gln Trp Glu Asp
        450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
                485                 490                 495

Asn Val Pro Ala Val Arg Val Thr Lys Lys Ser Glu Val Thr Ala Ala
                500                 505                 510

Ile Lys Lys Met Leu Glu Thr Pro Gly Pro Tyr Leu Leu Asp Ile Ile
            515                 520                 525

Val Pro His Gln Glu His Val Leu Pro Met Ile Pro Ser Gly Gly Ala
        530                 535                 540

Phe Lys Asp Met Ile Met Glu Gly Asp Gly Arg Thr Ser
545                 550                 555

<210> SEQ ID NO 17
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (718)..(719)
<223> OTHER INFORMATION: unknown nucleotide

<400> SEQUENCE: 17 gtc gac gtc ttc gcc tac ccc ggc ggc gcc tcc atg gag atc cac cag    48
Val Asp Val Phe Ala Tyr Pro Gly Gly Ala Ser Met Glu Ile His Gln
1               5                   10                  15 gcg ctg acg cgc tcg ccc gtc atc acc aac cac ctc ttc cgc cac gag    96
Ala Leu Thr Arg Ser Pro Val Ile Thr Asn His Leu Phe Arg His Glu
            20                  25                  30 cag ggg gag gcg ttc gcg gcg tcc ggc tac gcc cgc gcg tcc ggc cgc   144
Gln Gly Glu Ala Phe Ala Ala Ser Gly Tyr Ala Arg Ala Ser Gly Arg
        35                  40                  45 gtc ggc gtc tgc gtc gcc acc tcc ggc ccg ggg gcc acc aac ctc gtc   192
Val Gly Val Cys Val Ala Thr Ser Gly Pro Gly Ala Thr Asn Leu Val
    50                  55                  60 tcc gcg ctc gcc gac gcc ctc ctc gac tcc atc ccc atg gtc gcc atc   240
Ser Ala Leu Ala Asp Ala Leu Leu Asp Ser Ile Pro Met Val Ala Ile
65                  70                  75                  80 acg ggc cag gtc ccc cgc cgc atg atc ggc acg gac gcg ttc cag gag   288
```

|     |     |     |     |     |     |     |     |     |     |     |     |     |
|---|---|---|---|---|---|---|---|---|---|---|---|---|
| Thr | Gly | Gln | Val | Pro | Arg | Arg | Met | Ile | Gly | Thr | Asp | Ala | Phe | Gln | Glu |
|     |     |     |     | 85  |     |     |     |     | 90  |     |     |     |     | 95  |     |

```
acg ccc ata gtg gag gtc acg cgc tcc atc acc aag cac aac tac ctg      336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc      384
Val Leu Asp Val Glu Asp Ile Pro Arg Val Ile Gln Glu Ala Phe Phe
            115                 120                 125 ctt gca tcc tct ggc cgc ccg ggg ccg gtg cta gtt gat atc ccc aag      432
Leu Ala Ser Ser Gly Arg Pro Gly Pro Val Leu Val Asp Ile Pro Lys
            130                 135                 140 gac atc cag cag cag atg gct gtg ccc gtc tgg gac act cca atg agt      480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg      528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg      576
Leu Glu Gln Val Leu Arg Leu Val Gly Glu Ser Arg Arg Pro Ile Leu
            180                 185                 190 tat gtt ggt ggt ggc tgc gct gcg tct ggc gag gag ttg cgc cgc ttt      624
Tyr Val Gly Gly Gly Cys Ala Ala Ser Gly Glu Glu Leu Arg Arg Phe
            195                 200                 205 gtt gag ctt act ggg att cca gtt aca act act ctg atg ggc ctt ggc      672
Val Glu Leu Thr Gly Ile Pro Val Thr Thr Thr Leu Met Gly Leu Gly
210                 215                 220 aac ttc ccc agc gac gac cca ctg tct ctg cgc atg ctt ggg atg nnt      720
Asn Phe Pro Ser Asp Asp Pro Leu Ser Leu Arg Met Leu Gly Met Asn
225                 230                 235                 240 ggc act gtg tat gca aat tat gca gta gat aag gct gac ctg ttg ctc      768
Gly Thr Val Tyr Ala Asn Tyr Ala Val Asp Lys Ala Asp Leu Leu Leu
                245                 250                 255 gca ttt ggt gtg cgg ttt gat gat cgt gtg act ggg aaa atc gag gct      816
Ala Phe Gly Val Arg Phe Asp Asp Arg Val Thr Gly Lys Ile Glu Ala
            260                 265                 270 ttt gca agc agg tcc aag att gtg cac att gac att gac cca gct gag      864
Phe Ala Ser Arg Ser Lys Ile Val His Ile Asp Ile Asp Pro Ala Glu
            275                 280                 285 att ggc aag aac aag cag cca cat gtc tcc att tgt gca gat gtt aag      912
Ile Gly Lys Asn Lys Gln Pro His Val Ser Ile Cys Ala Asp Val Lys
            290                 295                 300 ctt gct tta cag ggg ttg aat gat cta tta aat ggg agc aaa gca caa      960
Leu Ala Leu Gln Gly Leu Asn Asp Leu Leu Asn Gly Ser Lys Ala Gln
305                 310                 315                 320 cag ggt ctg gat ttt ggt cca tgg cac aag gag ttg gat cag cag aag     1008
Gln Gly Leu Asp Phe Gly Pro Trp His Lys Glu Leu Asp Gln Gln Lys
                325                 330                 335 agg gag ttt cct cta gga ttc aag act ttt ggc gag gcc atc ccg ccg     1056
Arg Glu Phe Pro Leu Gly Phe Lys Thr Phe Gly Glu Ala Ile Pro Pro
            340                 345                 350 caa tat gct atc cag gta ctg gat gag ctg aca aaa ggg gag gcg atc     1104
Gln Tyr Ala Ile Gln Val Leu Asp Glu Leu Thr Lys Gly Glu Ala Ile
            355                 360                 365 att gcc act ggt gtt ggg cag cac cag atg tgg gcg gct cag tat tac     1152
Ile Ala Thr Gly Val Gly Gln His Gln Met Trp Ala Ala Gln Tyr Tyr
370                 375                 380 act tac aag cgg cca cgg cag tgg ctg tct tcg tct ggt ttg ggg gca     1200
Thr Tyr Lys Arg Pro Arg Gln Trp Leu Ser Ser Ser Gly Leu Gly Ala
385                 390                 395                 400 atg gga ttt ggg tta cca gct gca gct ggc gct gct gtg gcc aac cca     1248
```

```
Met Gly Phe Gly Leu Pro Ala Ala Ala Gly Ala Ala Val Ala Asn Pro
                405                 410                 415 ggt gtt aca gtt gtt gac att gat ggt gat ggt agt ttc ctc atg aac      1296
Gly Val Thr Val Val Asp Ile Asp Gly Asp Gly Ser Phe Leu Met Asn
            420                 425                 430 att cag gag ttg gcg ttg atc cgc att gag aac ctc cca gtg aag gtg      1344
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat      1392
Met Ile Leu Asn Asn Gln His Leu Gly Met Val Val Gln Trp Glu Asp
    450                 455                 460 agg ttt tac aag gcc aat cgg gcg cac aca tac ctt ggc aac cca gaa      1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc      1488
Asn Glu Ser Glu Ile Tyr Pro Asp Phe Val Thr Ile Ala Lys Gly Phe
                485                 490                 495 aac gtt cca gca gtt cga gtg acg aag aag agc gaa gtc act gca gca      1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc ata      1584
Ile Lys Lys Met Leu Glu Thr Pro Gly Pro Tyr Leu Leu Asp Ile Ile
        515                 520                 525 gtc ccg cat cag gag cac gtg ctg cct atg atc cca aac ggt ggt gct      1632
Val Pro His Gln Glu His Val Leu Pro Met Ile Pro Asn Gly Gly Ala
    530                 535                 540 ttc aag gac atg atc atg gag ggt gat ggc agg acc tcg tac              1674
Phe Lys Asp Met Ile Met Glu Gly Asp Gly Arg Thr Ser Tyr
545                 550                 555

<210> SEQ ID NO 18
<211> LENGTH: 557
<212> TYPE: PRT
<213> ORGANISM: Triticum aestivum

<400> SEQUENCE: 18

Val Asp Val Phe Ala Tyr Pro Gly Gly Ala Ser Met Glu Ile His Gln
  1               5                  10                  15

Ala Leu Thr Arg Ser Pro Val Ile Thr Asn His Leu Phe Arg His Glu
             20                  25                  30

Gln Gly Glu Ala Phe Ala Ala Ser Gly Tyr Ala Arg Ala Ser Gly Arg
         35                  40                  45

Val Gly Val Cys Val Ala Thr Ser Gly Pro Gly Ala Thr Asn Leu Val
     50                  55                  60

Ser Ala Leu Ala Asp Ala Leu Leu Asp Ser Ile Pro Met Val Ala Ile
 65                  70                  75                  80

Thr Gly Gln Val Pro Arg Arg Met Ile Gly Thr Asp Ala Phe Gln Glu
                 85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175
```

```
Leu Glu Gln Val Leu Arg Leu Val Gly Glu Ser Arg Arg Pro Ile Leu
            180                 185                 190

Tyr Val Gly Gly Cys Ala Ala Ser Gly Glu Glu Leu Arg Arg Phe
        195                 200                 205

Val Glu Leu Thr Gly Ile Pro Val Thr Thr Leu Met Gly Leu Gly
210                 215                 220

Asn Phe Pro Ser Asp Asp Pro Leu Ser Leu Arg Met Leu Gly Met Asn
225                 230                 235                 240

Gly Thr Val Tyr Ala Asn Tyr Ala Val Asp Lys Ala Asp Leu Leu Leu
                245                 250                 255

Ala Phe Gly Val Arg Phe Asp Asp Arg Val Thr Gly Lys Ile Glu Ala
            260                 265                 270

Phe Ala Ser Arg Ser Lys Ile Val His Ile Asp Ile Asp Pro Ala Glu
        275                 280                 285

Ile Gly Lys Asn Lys Gln Pro His Val Ser Ile Cys Ala Asp Val Lys
    290                 295                 300

Leu Ala Leu Gln Gly Leu Asn Asp Leu Leu Asn Gly Ser Lys Ala Gln
305                 310                 315                 320

Gln Gly Leu Asp Phe Gly Pro Trp His Lys Glu Leu Asp Gln Gln Lys
                325                 330                 335

Arg Glu Phe Pro Leu Gly Phe Lys Thr Phe Gly Glu Ala Ile Pro Pro
            340                 345                 350

Gln Tyr Ala Ile Gln Val Leu Asp Glu Leu Thr Lys Gly Glu Ala Ile
        355                 360                 365

Ile Ala Thr Gly Val Gly Gln His Gln Met Trp Ala Ala Gln Tyr Tyr
    370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Gly Ala Val Ala Asn Pro
                405                 410                 415

Gly Val Thr Val Val Asp Ile Asp Gly Asp Gly Ser Phe Leu Met Asn
            420                 425                 430

Ile Gln Glu Leu Ala Leu Ile Arg Ile Glu Asn Leu Pro Val Lys Val
        435                 440                 445

Met Ile Leu Asn Asn Gln His Leu Gly Met Val Val Gln Trp Glu Asp
    450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
                485                 490                 495

Asn Val Pro Ala Val Arg Val Thr Lys Lys Ser Glu Val Thr Ala Ala
            500                 505                 510

Ile Lys Lys Met Leu Glu Thr Pro Gly Pro Tyr Leu Leu Asp Ile Ile
        515                 520                 525

Val Pro His Gln Glu His Val Leu Pro Met Ile Pro Asn Gly Gly Ala
    530                 535                 540

Phe Lys Asp Met Ile Met Glu Gly Asp Gly Arg Thr Ser
545                 550                 555

<210> SEQ ID NO 19
<211> LENGTH: 1674
<212> TYPE: DNA
<213> ORGANISM: Triticum aestivum
<220> FEATURE:
<221> NAME/KEY: CDS
<222> LOCATION: (1)..(1671)
```

```
<220> FEATURE:
<221> NAME/KEY: modified_base
<222> LOCATION: (643)
<223> OTHER INFORMATION: unknown nucleotide
<220> FEATURE:
<221> NAME/KEY: modified_base
<222> LOCATION: (776)
<223> OTHER INFORMATION: unknown nucleotide
<220> FEATURE:
<221> NAME/KEY: modified_base
<222> LOCATION: (873)
<223> OTHER INFORMATION: unknown nucleotide
<220> FEATURE:
<221> NAME/KEY: modified_base
<222> LOCATION: (879)
<223> OTHER INFORMATION: unknown nucleotide

<400> SEQUENCE: 19 gtc gac gtc ttc gcc tac ccc ggc ggc gcc tcc atg gag atc cac cag      48
Val Asp Val Phe Ala Tyr Pro Gly Gly Ala Ser Met Glu Ile His Gln
 1               5                  10                  15 gcg ctg acg cgc tcg ccc gtc atc acc aac cac ctc ttc cgc cac gag      96
Ala Leu Thr Arg Ser Pro Val Ile Thr Asn His Leu Phe Arg His Glu
             20                  25                  30 cag ggg gag gcg ttc gcg gcg tcc ggc tac gcc cgc gcg tcc ggc cgc     144
Gln Gly Glu Ala Phe Ala Ala Ser Gly Tyr Ala Arg Ala Ser Gly Arg
         35                  40                  45 gtc ggc gtc tgc gtc gcc acc tcc ggc ccg ggg gcc acc aac ctc gtc     192
Val Gly Val Cys Val Ala Thr Ser Gly Pro Gly Ala Thr Asn Leu Val
     50                  55                  60 tcc gcg ctc gcc gac gcc ctc ctc gac tcc atc ccc atg gtc gcc atc     240
Ser Ala Leu Ala Asp Ala Leu Leu Asp Ser Ile Pro Met Val Ala Ile
 65                  70                  75                  80 acg ggc cag gtc ccc cgc cgc atg atc ggc acg gac gcg ttc cag gag     288
Thr Gly Gln Val Pro Arg Arg Met Ile Gly Thr Asp Ala Phe Gln Glu
                 85                  90                  95 acg ccc ata gtg gag gtc acg cgc tcc atc acc aag cac aac tac ctg     336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc     384
Val Leu Asp Val Glu Asp Ile Pro Arg Val Ile Gln Glu Ala Phe Phe
        115                 120                 125 ctt gca tcc tct ggc cgc ccg ggg ccg gtg cta gtt gat atc ccc aag     432
Leu Ala Ser Ser Gly Arg Pro Gly Pro Val Leu Val Asp Ile Pro Lys
    130                 135                 140 gac atc cag cag cag atg gct gtg ccc gtc tgg gac act cca atg agt     480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg     528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg     576
Leu Glu Gln Val Leu Arg Leu Val Gly Glu Ser Arg Arg Pro Ile Leu
            180                 185                 190 tat gtt ggt ggt ggc tgc gct gcg tct ggc gag gag ttg cgc cgc ttt     624
Tyr Val Gly Gly Gly Cys Ala Ala Ser Gly Glu Glu Leu Arg Arg Phe
        195                 200                 205 gtt gag ctt act ggg att nca gtt aca act act ctg atg ggc ctt ggc     672
Val Glu Leu Thr Gly Ile Thr Val Thr Thr Thr Leu Met Gly Leu Gly
    210                 215                 220 aac ttc ccc agc gac gac cca ctg tct ctg cgc atg ctt ggg atg cat     720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ctc     768
```

```
                Gly Thr Val Tyr Ala Asn Tyr Ala Val Asp Lys Ala Asp Leu Leu Leu
                                    245                 250                 255 gca ttt gnt gtg cgg ttt gat gat cgt gtg act ggg aaa atc gag gct            816
Ala Phe Asp Val Arg Phe Asp Asp Arg Val Thr Gly Lys Ile Glu Ala
                    260                 265                 270 ttt gca agc agg tcc aag att gtg cac att gac att gac cca gct gag            864
Phe Ala Ser Arg Ser Lys Ile Val His Ile Asp Ile Asp Pro Ala Glu
                    275                 280                 285 att ggc aan aac aan cag cca cat gtc tcc att tgt gca gat gtt aag            912
Ile Gly Lys Asn Lys Gln Pro His Val Ser Ile Cys Ala Asp Val Lys
                290                 295                 300 ctt gct tta cag ggg ttg aat gat cta tta aat ggg agc aaa gca caa            960
Leu Ala Leu Gln Gly Leu Asn Asp Leu Leu Asn Gly Ser Lys Ala Gln
305                 310                 315                 320 cag ggt ctg gat ttt ggt cca tgg cac aag gag ttg gat cag cag aag           1008
Gln Gly Leu Asp Phe Gly Pro Trp His Lys Glu Leu Asp Gln Gln Lys
                    325                 330                 335 agg gag ttt cct cta gga ttc aag act ttt ggc gag gcc atc ccg ccg           1056
Arg Glu Phe Pro Leu Gly Phe Lys Thr Phe Gly Glu Ala Ile Pro Pro
                    340                 345                 350 caa tat gct atc cag gta ctg gat gag ctg aca aaa ggg gag gcg atc           1104
Gln Tyr Ala Ile Gln Val Leu Asp Glu Leu Thr Lys Gly Glu Ala Ile
                355                 360                 365 att gcc act ggt gtt ggg cag cac cag atg tgg gcg gct cag tat tac           1152
Ile Ala Thr Gly Val Gly Gln His Gln Met Trp Ala Ala Gln Tyr Tyr
                370                 375                 380 act tac aag cgg cca cgg cag tgg ctg tct tcg tct ggt ttg ggg gca           1200
Thr Tyr Lys Arg Pro Arg Gln Trp Leu Ser Ser Ser Gly Leu Gly Ala
385                 390                 395                 400 atg gga ttt ggg tta cca gct gca gct ggc gct gct gtg gcc aac cca           1248
Met Gly Phe Gly Leu Pro Ala Ala Ala Gly Ala Ala Val Ala Asn Pro
                    405                 410                 415 ggt gtt aca gtt gtt gac att gat ggt gat ggt agt ttc ctc atg aac           1296
Gly Val Thr Val Val Asp Ile Asp Gly Asp Gly Ser Phe Leu Met Asn
                    420                 425                 430 att cag gag ttg gcg ttg atc cgc att gag aac ctc cca gtg aag gtg           1344
Ile Gln Glu Leu Ala Leu Ile Arg Ile Glu Asn Leu Pro Val Lys Val
                435                 440                 445 atg ata ttg aac aac cag cat ctg gga atg gtg gtg cag tgg gag gat           1392
Met Ile Leu Asn Asn Gln His Leu Gly Met Val Val Gln Trp Glu Asp
450                 455                 460 agg ttt tac aag gcc aat cgg gcg cac aca tac ctt ggc aac cca gaa           1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc           1488
Asn Glu Ser Glu Ile Tyr Pro Asp Phe Val Thr Ile Ala Lys Gly Phe
                    485                 490                 495 aac gtt cca gca gtt cga gtg acg aag aag agc gaa gtc act gca gca           1536
Asn Val Pro Ala Val Arg Val Thr Lys Lys Ser Glu Val Thr Ala Ala
                    500                 505                 510 atc aag aag atg ctt gag acc cca ggg cca tac ttg ttg gat atc ata           1584
Ile Lys Lys Met Leu Glu Thr Pro Gly Pro Tyr Leu Leu Asp Ile Ile
                515                 520                 525 gtc ccg cat cag gag cac gtg ctg cct atg atc cca aac ggt ggt gct           1632
Val Pro His Gln Glu His Val Leu Pro Met Ile Pro Asn Gly Gly Ala
530                 535                 540 ttc aag gac atg atc atg gag ggt gat ggc agg acc tcg tac                   1674
Phe Lys Asp Met Ile Met Glu Gly Asp Gly Arg Thr Ser Tyr
545                 550                 555
```

```
<210> SEQ ID NO 20
<211> LENGTH: 557
<212> TYPE: PRT
<213> ORGANISM: Triticum aestivum

<400> SEQUENCE: 20

Val Asp Val Phe Ala Tyr Pro Gly Gly Ala Ser Met Glu Ile His Gln
 1               5                  10                  15

Ala Leu Thr Arg Ser Pro Val Ile Thr Asn His Leu Phe Arg His Glu
            20                  25                  30

Gln Gly Glu Ala Phe Ala Ala Ser Gly Tyr Ala Arg Ala Ser Gly Arg
        35                  40                  45

Val Gly Val Cys Val Ala Thr Ser Gly Pro Gly Ala Thr Asn Leu Val
    50                  55                  60

Ser Ala Leu Ala Asp Ala Leu Leu Asp Ser Ile Pro Met Val Ala Ile
65                  70                  75                  80

Thr Gly Gln Val Pro Arg Arg Met Ile Gly Thr Asp Ala Phe Gln Glu
                85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
            180                 185                 190

Tyr Val Gly Gly Gly Cys Ala Ala Ser Gly Glu Glu Leu Arg Arg Phe
        195                 200                 205

Val Glu Leu Thr Gly Ile Thr Val Thr Thr Thr Leu Met Gly Leu Gly
    210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Leu
                245                 250                 255

Ala Phe Asp Val Arg Phe Asp Asp Arg Val Thr Gly Lys Ile Glu Ala
            260                 265                 270

Phe Ala Ser Arg Ser Lys Ile Val His Ile Asp Ile Asp Pro Ala Glu
        275                 280                 285

Ile Gly Lys Asn Lys Gln Pro His Val Ser Ile Cys Ala Asp Val Lys
    290                 295                 300

Leu Ala Leu Gln Gly Leu Asn Asp Leu Leu Asn Gly Ser Lys Ala Gln
305                 310                 315                 320

Gln Gly Leu Asp Phe Gly Pro Trp His Lys Glu Leu Asp Gln Gln Lys
                325                 330                 335

Arg Glu Phe Pro Leu Gly Phe Lys Thr Phe Gly Glu Ala Ile Pro Pro
            340                 345                 350

Gln Tyr Ala Ile Gln Val Leu Asp Glu Leu Thr Lys Gly Glu Ala Ile
        355                 360                 365

Ile Ala Thr Gly Val Gly Gln His Gln Met Trp Ala Ala Gln Tyr Tyr
    370                 375                 380

Thr Tyr Lys Arg Pro Arg Gln Trp Leu Ser Ser Ser Gly Leu Gly Ala
```

```
                385                 390                 395                 400
        Met Gly Phe Gly Leu Pro Ala Ala Gly Ala Ala Val Ala Asn Pro
                        405                 410                 415

Gly Val Thr Val Val Asp Ile Asp Gly Asp Ser Phe Leu Met Asn
                        420                 425                 430

Ile Gln Glu Leu Ala Leu Ile Arg Ile Glu Asn Leu Pro Val Lys Val
                        435                 440                 445

Met Ile Leu Asn Asn Gln His Leu Gly Met Val Val Gln Trp Glu Asp
                        450                 455                 460

Arg Phe Tyr Lys Ala Asn Arg Ala His Thr Tyr Leu Gly Asn Pro Glu
        465                 470                 475                 480

Asn Glu Ser Glu Ile Tyr Pro Asp Phe Val Thr Ile Ala Lys Gly Phe
                        485                 490                 495

Asn Val Pro Ala Val Arg Val Thr Lys Lys Ser Glu Val Thr Ala Ala
                        500                 505                 510

Ile Lys Lys Met Leu Glu Thr Pro Gly Pro Tyr Leu Leu Asp Ile Ile
                        515                 520                 525

Val Pro His Gln Glu His Val Leu Pro Met Ile Pro Asn Gly Gly Ala
                        530                 535                 540

Phe Lys Asp Met Ile Met Glu Gly Asp Gly Arg Thr Ser
        545                 550                 555

<210> SEQ ID NO 21
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (766)
<223> OTHER INFORMATION: unknown nucleotide
<220> FEATURE:
<221> NAME/KEY: modified_base
<222> LOCATION: (769)
<223> OTHER INFORMATION: unknown nucleotide

<400> SEQUENCE: 21 gtc gac gtc ttc gcc tac ccc ggc ggc gcc tcc atg gag atc cac cag      48
Val Asp Val Phe Ala Tyr Pro Gly Gly Ala Ser Met Glu Ile His Gln
  1               5                  10                  15 gcg ctg acg cgc tcg ccc gtc atc acc aac cac ctc ttc cgc cac gag      96
Ala Leu Thr Arg Ser Pro Val Ile Thr Asn His Leu Phe Arg His Glu
                 20                  25                  30 cag ggg gag gcg ttc gcg gcg tcc ggc tac gcc cgc gcg tcc ggc cgc     144
Gln Gly Glu Ala Phe Ala Ala Ser Gly Tyr Ala Arg Ala Ser Gly Arg
             35                  40                  45 gtc ggc gtc tgc gtc gcc acc tcc ggc ccg ggg gcc acc aac ctc gtc     192
Val Gly Val Cys Val Ala Thr Ser Gly Pro Gly Ala Thr Asn Leu Val
         50                  55                  60 tcc gcg ctc gcc gac gcc ctc ctc gac tcc atc ccc atg gtc gcc atc     240
Ser Ala Leu Ala Asp Ala Leu Leu Asp Ser Ile Pro Met Val Ala Ile
 65                  70                  75                  80 acg ggc cag gtc ccc cgc cgc atg atc ggc acg gac gcg ttc cag gag     288
Thr Gly Gln Val Pro Arg Arg Met Ile Gly Thr Asp Ala Phe Gln Glu
                 85                  90                  95 acg ccc ata gtg gag gtc acg cgc tcc atc acc aag cac aac tac ctg     336
Thr Pro Ile Val Glu Val Thr Arg Ser Ile Thr Lys His Asn Tyr Leu
            100                 105                 110 gtc ctt gac gtg gag gat atc ccc gcg gtc atc cag gaa gcc ttc ttc     384
```

```
                Val Leu Asp Val Glu Asp Ile Pro Arg Val Ile Gln Glu Ala Phe Phe
                                115                 120                 125 cct gca tcc tct ggc cgc ccg ggg ccg gtg cta gtt gat atc ccc aag           432
Leu Ala Ser Ser Gly Arg Pro Gly Pro Val Leu Val Asp Ile Pro Lys
            130                 135                 140 gac atc cag cag cag atg gct gtg ccc gtc tgg gac act cca atg agt           480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg           528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg           576
Leu Glu Gln Val Leu Arg Leu Val Gly Glu Ser Arg Arg Pro Ile Leu
            180                 185                 190 tat gtt ggt ggt ggc tgc gct gcg tct ggc gag gag ttg cgc cgc ttt           624
Tyr Val Gly Gly Gly Cys Ala Ala Ser Gly Glu Glu Leu Arg Arg Phe
                195                 200                 205 gtt gag ctt act ggg att cca gtt aca act ctg atg ggc ctt ggc               672
Val Glu Leu Thr Gly Ile Pro Val Thr Thr Thr Leu Met Gly Leu Gly
210                 215                 220 aac ttc ccc agc gac gac cca ctg tct ctg cgc atg ctt ggg atg cat           720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ntc           768
Gly Thr Val Tyr Ala Asn Tyr Ala Val Asp Lys Ala Asp Leu Leu Ile
                245                 250                 255 nca ttt ggt gtg cgg ttt gat gat cgt gtg act ggg aaa atc gag gct           816
Thr Phe Gly Val Arg Phe Asp Asp Arg Val Thr Gly Lys Ile Glu Ala
                260                 265                 270 ttt gca agc agg tcc aag att gtg cac att gac att gac cca gct gag           864
Phe Ala Ser Arg Ser Lys Ile Val His Ile Asp Ile Asp Pro Ala Glu
                275                 280                 285 att ggc aag aac aag cag cca cat gtc tcc att tgt gcc gat gtt aag           912
Ile Gly Lys Asn Lys Gln Pro His Val Ser Ile Cys Ala Asp Val Lys
            290                 295                 300 ctt gct tta cag ggg ttg aat gat cta tta aat ggg agc aaa gca caa           960
Leu Ala Leu Gln Gly Leu Asn Asp Leu Leu Asn Gly Ser Lys Ala Gln
305                 310                 315                 320 cag ggt ctg gat ttt ggt cca tgg cac aag gag ttg gat cag cag aag          1008
Gln Gly Leu Asp Phe Gly Pro Trp His Lys Glu Leu Asp Gln Gln Lys
                325                 330                 335 agg gag ttt cct cta gga ttc aag act ttt ggc gag gcc atc ccg ccg          1056
Arg Glu Phe Pro Leu Gly Phe Lys Thr Phe Gly Glu Ala Ile Pro Pro
            340                 345                 350 caa tat gct atc cag gta ctg gat gag ctg aca aaa ggg gag gcg atc          1104
Gln Tyr Ala Ile Gln Val Leu Asp Glu Leu Thr Lys Gly Glu Ala Ile
                355                 360                 365 att gcc act ggt gtt ggg cag cac cag atg tgg gcg gct cag tat tac          1152
Ile Ala Thr Gly Val Gly Gln His Gln Met Trp Ala Ala Gln Tyr Tyr
            370                 375                 380 act tac aag cgg cca cgg cag tgg ctg tct tcg tct ggt ttg ggg gca          1200
Thr Tyr Lys Arg Pro Arg Gln Trp Leu Ser Ser Ser Gly Leu Gly Ala
385                 390                 395                 400 atg gga ttt ggg tta cca gct gca gct ggc gct gct gtg gcc aac cca          1248
Met Gly Phe Gly Leu Pro Ala Ala Ala Gly Ala Ala Val Ala Asn Pro
                405                 410                 415 ggt gtt aca gtt gtt gac att gat ggt gat ggt agt ttc ctc atg aac          1296
Gly Val Thr Val Val Asp Ile Asp Gly Asp Gly Ser Phe Leu Met Asn
            420                 425                 430 att cag gag ttg gcg ttg atc cgc att gag aac ctc cca gtg aag gtg          1344
```

```
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat      1392
Met Ile Leu Asn Asn Gln His Leu Gly Met Val Val Gln Trp Glu Asp
    450                 455                 460 agg ttt tac aag gcc aat cgg gcg cac aca tac ctt ggc aac cca gaa      1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc      1488
Asn Glu Ser Glu Ile Tyr Pro Asp Phe Val Thr Ile Ala Lys Gly Phe
                485                 490                 495 aac gtt cca gca gtt cga gtg acg aag aag agc gaa gtc act gca gca      1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc ata      1584
Ile Lys Lys Met Leu Glu Thr Pro Gly Pro Tyr Leu Leu Asp Ile Ile
        515                 520                 525 gtc ccg cat cag gag cac gtg ctg cct atg atc cca agc ggt ggt gct      1632
Val Pro His Gln Glu His Val Leu Pro Met Ile Pro Ser Gly Gly Ala
    530                 535                 540 ttc aag gac atg atc atg gag ggt gat ggc agg acc tcg tac              1674
Phe Lys Asp Met Ile Met Glu Gly Asp Gly Arg Thr Ser
545                 550                 555

<210> SEQ ID NO 22
<211> LENGTH: 557
<212> TYPE: PRT
<213> ORGANISM: Triticum aestivum

<400> SEQUENCE: 22

Val Asp Val Phe Ala Tyr Pro Gly Gly Ala Ser Met Glu Ile His Gln
  1               5                  10                  15

Ala Leu Thr Arg Ser Pro Val Ile Thr Asn His Leu Phe Arg His Glu
             20                  25                  30

Gln Gly Glu Ala Phe Ala Ala Ser Gly Tyr Ala Arg Ala Ser Gly Arg
         35                  40                  45

Val Gly Val Cys Val Ala Thr Ser Gly Pro Gly Ala Thr Asn Leu Val
     50                  55                  60

Ser Ala Leu Ala Asp Ala Leu Leu Asp Ser Ile Pro Met Val Ala Ile
 65                  70                  75                  80

Thr Gly Gln Val Pro Arg Arg Met Ile Gly Thr Asp Ala Phe Gln Glu
                 85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
            180                 185                 190

Tyr Val Gly Gly Gly Cys Ala Ala Ser Gly Glu Glu Leu Arg Arg Phe
        195                 200                 205

Val Glu Leu Thr Gly Ile Pro Val Thr Thr Thr Leu Met Gly Leu Gly
    210                 215                 220
```

```
Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Ile
            245                 250                 255

Thr Phe Gly Val Arg Phe Asp Asp Arg Val Thr Gly Lys Ile Glu Ala
        260                 265                 270

Phe Ala Ser Arg Ser Lys Ile Val His Ile Asp Ile Asp Pro Ala Glu
    275                 280                 285

Ile Gly Lys Asn Lys Gln Pro His Val Ser Ile Cys Ala Asp Val Lys
290                 295                 300

Leu Ala Leu Gln Gly Leu Asn Asp Leu Leu Asn Gly Ser Lys Ala Gln
305                 310                 315                 320

Gln Gly Leu Asp Phe Gly Pro Trp His Lys Glu Leu Asp Gln Gln Lys
            325                 330                 335

Arg Glu Phe Pro Leu Gly Phe Lys Thr Phe Gly Glu Ala Ile Pro Pro
        340                 345                 350

Gln Tyr Ala Ile Gln Val Leu Asp Glu Leu Thr Lys Gly Glu Ala Ile
    355                 360                 365

Ile Ala Thr Gly Val Gly Gln His Gln Met Trp Ala Ala Gln Tyr Tyr
370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Gly Ala Ala Val Ala Asn Pro
            405                 410                 415

Gly Val Thr Val Val Asp Ile Asp Gly Asp Gly Ser Phe Leu Met Asn
        420                 425                 430

Ile Gln Glu Leu Ala Leu Ile Arg Ile Glu Asn Leu Pro Val Lys Val
    435                 440                 445

Met Ile Leu Asn Asn Gln His Leu Gly Met Val Val Gln Trp Glu Asp
450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
            485                 490                 495

Asn Val Pro Ala Val Arg Val Thr Lys Lys Ser Glu Val Thr Ala Ala
        500                 505                 510

Ile Lys Lys Met Leu Glu Thr Pro Gly Pro Tyr Leu Leu Asp Ile Ile
    515                 520                 525

Val Pro His Gln Glu His Val Leu Pro Met Ile Pro Ser Gly Gly Ala
530                 535                 540

Phe Lys Asp Met Ile Met Glu Gly Asp Gly Arg Thr Ser
545                 550                 555

<210> SEQ ID NO 23
<211> LENGTH: 1677
<212> TYPE: DNA
<213> ORGANISM: Triticum aestivum
<220> FEATURE:
<221> NAME/KEY: CDS
<222> LOCATION: (1)..(1674)
<220> FEATURE:
<221> NAME/KEY: modified_base
<222> LOCATION: (766)
<223> OTHER INFORMATION: unknown nucleotide
<220> FEATURE:
<221> NAME/KEY: modified_base
<222> LOCATION: (839)
<223> OTHER INFORMATION: unknown nucleotide
```

```
<220> FEATURE:
<221> NAME/KEY: modified_base
<222> LOCATION: (912)
<223> OTHER INFORMATION: unknown nucleotide
<220> FEATURE:
<221> NAME/KEY: modified_base
<222> LOCATION: (1008)
<223> OTHER INFORMATION: unknown nucleotide

<400> SEQUENCE: 23 gtc gac gtc ttc gcc tac ccc ggc ggc gcc tcc atg gag atc cac cag        48
Val Asp Val Phe Ala Tyr Pro Gly Gly Ala Ser Met Glu Ile His Gln
 1               5                  10                  15 gcg ctg acg cgc tcg ccc gtc atc acc aac cac ctc ttc cgc cac gag        96
Ala Leu Thr Arg Ser Pro Val Ile Thr Asn His Leu Phe Arg His Glu
             20                  25                  30 cag ggg gag gcg ttc gcg gcg tcc ggc tac gcc cgc gcg tcc ggc cgc       144
Gln Gly Glu Ala Phe Ala Ala Ser Gly Tyr Ala Arg Ala Ser Gly Arg
         35                  40                  45 gtc ggc gtc tgc gtc gcc acc tcc ggc ccg ggg gcc acc aac ctc gtc       192
Val Gly Val Cys Val Ala Thr Ser Gly Pro Gly Ala Thr Asn Leu Val
 50                  55                  60 tcc gcg ctc gcc gac gcc ctc ctc gac tcc atc ccc atg gtc gcc atc       240
Ser Ala Leu Ala Asp Ala Leu Leu Asp Ser Ile Pro Met Val Ala Ile
 65                  70                  75                  80 acg ggc cag gtc ccc cgc cgc atg atc ggc acg gac gcg ttc cag gag       288
Thr Gly Gln Val Pro Arg Arg Met Ile Gly Thr Asp Ala Phe Gln Glu
             85                  90                  95 acg ccc ata gtg gag gtc acg cgc tcc atc acc aag cac aac tac ctg       336
Thr Pro Ile Val Glu Val Thr Arg Ser Ile Thr Lys His Asn Tyr Leu
        100                 105                 110 gtc ctt gac gtg gag gat atc ccc cgc gtc atc cag gaa gcc ttc ttc       384
Val Leu Asp Val Glu Asp Ile Pro Arg Val Ile Gln Glu Ala Phe Phe
        115                 120                 125 ctt gca tcc tct ggc cgc ccg ggg ccg gtg cta gtt gat atc ccc aag       432
Leu Ala Ser Ser Gly Arg Pro Gly Pro Val Leu Val Asp Ile Pro Lys
        130                 135                 140 gac atc cag cag cag atg gct gtg ccc gtc tgg gac act cca atg agt       480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg       528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg       576
Leu Glu Gln Val Leu Arg Leu Val Gly Glu Ser Arg Arg Pro Ile Leu
            180                 185                 190 tat gtt ggt ggt ggc tgc gct gcg tct ggc gag gag ttg cgc cgc ttt       624
Tyr Val Gly Gly Gly Cys Ala Ala Ser Gly Glu Glu Leu Arg Arg Phe
        195                 200                 205 gtt gag ctt act ggg att cca gtt aca act act ctg atg ggc ctt ggc       672
Val Glu Leu Thr Gly Ile Pro Val Thr Thr Thr Leu Met Gly Leu Gly
        210                 215                 220 aac ttc ccc agc gac gac cca ctg tct ctg cgc atg ctt ggg atg cat       720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ntc       768
Gly Thr Val Tyr Ala Asn Tyr Ala Val Asp Lys Ala Asp Leu Leu Ile
                245                 250                 255 gca ttt ggt gtg cgg ttt gat gat cgt gtg act ggg aaa atc gag gct       816
Ala Phe Gly Val Arg Phe Asp Asp Arg Val Thr Gly Lys Ile Glu Ala
            260                 265                 270 ttt gca agc agg tcc aag att gng cac att gac att gac cca gct gag       864
```

```
att ggc aag aac aag cag cca cat gtc tcc att tgt gca gat gtt aan    912
Ile Gly Lys Asn Lys Gln Pro His Val Ser Ile Cys Ala Asp Val Lys
        290                 295                 300 ctt gct tta cag ggg ttg aat gat cta tta aat ggg agc aaa gca caa    960
Leu Ala Leu Gln Gly Leu Asn Asp Leu Leu Asn Gly Ser Lys Ala Gln
305                 310                 315                 320 cag ggt ctg gat ttt ggt cca tgg cac aag gag ttg gat cag can aan   1008
Gln Gly Leu Asp Phe Gly Pro Trp His Lys Glu Leu Asp Gln Thr Lys
                325                 330                 335 agg gag ttt cct cta gga ttc aag act ttt ggc gag gcc atc ccg ccg   1056
Arg Glu Phe Pro Leu Gly Phe Lys Thr Phe Gly Glu Ala Ile Pro Pro
            340                 345                 350 caa tat gct atc cag gta ctg gat gag ctg aca aaa ggg gag gcg atc   1104
Gln Tyr Ala Ile Gln Val Leu Asp Glu Leu Thr Lys Gly Glu Ala Ile
        355                 360                 365 att gcc act ggt gtt ggg cag cac cag atg tgg gcg gct cag tat tac   1152
Ile Ala Thr Gly Val Gly Gln His Gln Met Trp Ala Ala Gln Tyr Tyr
370                 375                 380 act tac aag cgg cca cgg cag tgg ctg tct tcg tct ggt ttg ggg gca   1200
Thr Tyr Lys Arg Pro Arg Gln Trp Leu Ser Ser Ser Gly Leu Gly Ala
385                 390                 395                 400 atg gga ttt ggg tta cca gct gca gct ggc gct gct gtg gcc aac cca   1248
Met Gly Phe Gly Leu Pro Ala Ala Ala Gly Ala Ala Val Ala Asn Pro
                405                 410                 415 ggt gtt aca gtt gtt gac att gat ggt gat ggt agt ttc ctc atg aac   1296
Gly Val Thr Val Val Asp Ile Asp Gly Asp Gly Ser Phe Leu Met Asn
            420                 425                 430 att cag gag ttg gcg ttg atc cgc att gag aac ctc cca gtg aag gtg   1344
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat   1392
Met Ile Leu Asn Asn Gln His Leu Gly Met Val Val Gln Trp Glu Asp
450                 455                 460 agg ttt tac aag gcc aat cgg gcg cac aca tac ctt ggc aac cca gaa   1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc   1488
Asn Glu Ser Glu Ile Tyr Pro Asp Phe Val Thr Ile Ala Lys Gly Phe
                485                 490                 495 aac gtt cca gca gtt cga gtg acg aag aag agc gaa gtc act gca gca   1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc ata   1584
Ile Lys Lys Met Leu Glu Thr Pro Gly Pro Tyr Leu Leu Asp Ile Ile
        515                 520                 525 gtc ccg cat cag gag cac gtg ctg cct atg atc cca aac ggt ggt gct   1632
Val Pro His Gln Glu His Val Leu Pro Met Ile Pro Asn Gly Gly Ala
530                 535                 540 ttc aag gac atg atc atg gag ggt gat ggc agg acc tcg tac tga       1677
Phe Lys Asp Met Ile Met Glu Gly Asp Gly Arg Thr Ser Tyr
545                 550                 555

<210> SEQ ID NO 24
<211> LENGTH: 558
<212> TYPE: PRT
<213> ORGANISM: Triticum aestivum

<400> SEQUENCE: 24

Val Asp Val Phe Ala Tyr Pro Gly Gly Ala Ser Met Glu Ile His Gln
```

```
              1               5              10              15
            Ala Leu Thr Arg Ser Pro Val Ile Thr Asn His Leu Phe Arg His Glu
                             20                  25                  30

Gln Gly Glu Ala Phe Ala Ala Ser Gly Tyr Ala Arg Ala Ser Gly Arg
                         35                  40                  45

Val Gly Val Cys Val Ala Thr Ser Gly Pro Gly Ala Thr Asn Leu Val
                     50                  55                  60

Ser Ala Leu Ala Asp Ala Leu Leu Asp Ser Ile Pro Met Val Ala Ile
             65                  70                  75                  80

Thr Gly Gln Val Pro Arg Arg Met Ile Gly Thr Asp Ala Phe Gln Glu
                             85                  90                  95

Thr Pro Ile Val Glu Val Thr Arg Ser Ile Thr Lys His Asn Tyr Leu
                        100                 105                 110

Val Leu Asp Val Glu Asp Ile Pro Arg Val Ile Gln Glu Ala Phe Phe
                        115                 120                 125

Leu Ala Ser Ser Gly Arg Pro Gly Pro Val Leu Val Asp Ile Pro Lys
                        130                 135                 140

Asp Ile Gln Gln Gln Met Ala Val Pro Val Trp Asp Thr Pro Met Ser
            145                 150                 155                 160

Leu Pro Gly Tyr Ile Ala Arg Leu Pro Lys Pro Pro Ser Thr Glu Ser
                            165                 170                 175

Leu Glu Gln Val Leu Arg Leu Val Gly Glu Ser Arg Arg Pro Ile Leu
                        180                 185                 190

Tyr Val Gly Gly Gly Cys Ala Ala Ser Gly Glu Glu Leu Arg Arg Phe
                        195                 200                 205

Val Glu Leu Thr Gly Ile Pro Val Thr Thr Thr Leu Met Gly Leu Gly
                        210                 215                 220

Asn Phe Pro Ser Asp Asp Pro Leu Ser Leu Arg Met Leu Gly Met His
            225                 230                 235                 240

Gly Thr Val Tyr Ala Asn Tyr Ala Val Asp Lys Ala Asp Leu Leu Ile
                            245                 250                 255

Ala Phe Gly Val Arg Phe Asp Asp Arg Val Thr Gly Lys Ile Glu Ala
                        260                 265                 270

Phe Ala Ser Arg Ser Lys Ile Glu His Ile Asp Ile Asp Pro Ala Glu
                        275                 280                 285

Ile Gly Lys Asn Lys Gln Pro His Val Ser Ile Cys Ala Asp Val Lys
                        290                 295                 300

Leu Ala Leu Gln Gly Leu Asn Asp Leu Leu Asn Gly Ser Lys Ala Gln
            305                 310                 315                 320

Gln Gly Leu Asp Phe Gly Pro Trp His Lys Glu Leu Asp Gln Thr Lys
                            325                 330                 335

Arg Glu Phe Pro Leu Gly Phe Lys Thr Phe Gly Glu Ala Ile Pro Pro
                        340                 345                 350

Gln Tyr Ala Ile Gln Val Leu Asp Glu Leu Thr Lys Gly Glu Ala Ile
                        355                 360                 365

Ile Ala Thr Gly Val Gly Gln His Gln Met Trp Ala Ala Gln Tyr Tyr
                        370                 375                 380

Thr Tyr Lys Arg Pro Arg Gln Trp Leu Ser Ser Gly Leu Gly Ala
            385                 390                 395                 400

Met Gly Phe Gly Leu Pro Ala Ala Gly Ala Ala Val Ala Asn Pro
                            405                 410                 415

Gly Val Thr Val Val Asp Ile Asp Gly Asp Gly Ser Phe Leu Met Asn
                        420                 425                 430
```

-continued

```
Ile Gln Glu Leu Ala Leu Ile Arg Ile Glu Asn Leu Pro Val Lys Val
            435                 440                 445
Met Ile Leu Asn Asn Gln His Leu Gly Met Val Val Gln Trp Glu Asp
    450                 455                 460
Arg Phe Tyr Lys Ala Asn Arg Ala His Thr Tyr Leu Gly Asn Pro Glu
465                 470                 475                 480
Asn Glu Ser Glu Ile Tyr Pro Asp Phe Val Thr Ile Ala Lys Gly Phe
                    485                 490                 495
Asn Val Pro Ala Val Arg Val Thr Lys Lys Ser Glu Val Thr Ala Ala
                500                 505                 510
Ile Lys Lys Met Leu Glu Thr Pro Gly Pro Tyr Leu Leu Asp Ile Ile
            515                 520                 525
Val Pro His Gln Glu His Val Leu Pro Met Ile Pro Asn Gly Gly Ala
    530                 535                 540
Phe Lys Asp Met Ile Met Glu Gly Asp Gly Arg Thr Ser Tyr
545                 550                 555
```

```
<210> SEQ ID NO 25
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (681)
<223> OTHER INFORMATION: unknown nucleotide
<220> FEATURE:
<221> NAME/KEY: modified_base
<222> LOCATION: (766)
<223> OTHER INFORMATION: unknown nucleotide

<400> SEQUENCE: 25
```

```
gtc gac gtc ttc gcc tac cct ggc ggc gcg tcc atg gag atc cac cag      48
Val Asp Val Phe Ala Tyr Pro Gly Gly Ala Ser Met Glu Ile His Gln
 1               5                  10                  15 gcg ctg acg cgc tcg cca gtc atc acc aac cac ctc ttc cgc cac gag      96
Ala Leu Thr Arg Ser Pro Val Ile Thr Asn His Leu Phe Arg His Glu
             20                  25                  30 cag ggg gag gcg ttc gcg gcg tcc ggg tac gcc cgc gcg tcc ggc cgc     144
Gln Gly Glu Ala Phe Ala Ala Ser Gly Tyr Ala Arg Ala Ser Gly Arg
         35                  40                  45 gtc ggc gtc tgc gtc gcc acc tcc ggc ccg ggg gcc acc aac ctc gtc     192
Val Gly Val Cys Val Ala Thr Ser Gly Pro Gly Ala Thr Asn Leu Val
     50                  55                  60 tcc gcg ctc gcc gac gct ctc ctc gac tcc atc ccc atg gtc gcc atc     240
Ser Ala Leu Ala Asp Ala Leu Leu Asp Ser Ile Pro Met Val Ala Ile
 65                  70                  75                  80 acg ggc cag gtc ccc cgc cgc atg atc ggc acg gat gcg ttc cag gag     288
Thr Gly Gln Val Pro Arg Arg Met Ile Gly Thr Asp Ala Phe Gln Glu
                 85                  90                  95 acg ccc atc gtg gag gtc acg cgc tcc atc acc aag cac aac tac ctg     336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc     384
Val Leu Asp Val Glu Asp Ile Pro Arg Val Ile Gln Glu Ala Phe Phe
        115                 120                 125 ctc gca tcc tct ggc cgc ccg ggg ccg gtg ctg gtt gat atc ccc aag     432
Leu Ala Ser Ser Gly Arg Pro Gly Pro Val Leu Val Asp Ile Pro Lys
    130                 135                 140 gac atc cag cag cag atg gct gtg cct gtc tgg gac acg ccg atg agt     480
```

```
                Asp Ile Gln Gln Gln Met Ala Val Pro Val Trp Asp Thr Pro Met Ser
                145                 150                 155                 160 ttg cca ggg tac atc gcc cgc ctg ccc aag cca cca tct act gaa tcg                  528
Leu Pro Gly Tyr Ile Ala Arg Leu Pro Lys Pro Pro Ser Thr Glu Ser
            165                 170                 175 ctt gag cag gtc ctg cgt ctg gtt ggc gag tca cgg cgc cca att ctg                  576
Leu Glu Gln Val Leu Arg Leu Val Gly Glu Ser Arg Arg Pro Ile Leu
        180                 185                 190 tat gtt ggt ggt ggc tgc gct gca tct ggt gag gag ttg cgc cgc ttt                  624
Tyr Val Gly Gly Gly Cys Ala Ala Ser Gly Glu Glu Leu Arg Arg Phe
        195                 200                 205 gtt gag ctc act ggg att cca gtt aca act act ctt atg ggc ctt ggc                  672
Val Glu Leu Thr Gly Ile Pro Val Thr Thr Thr Leu Met Gly Leu Gly
    210                 215                 220 aac ttc ccn agt gac gac cca ctg tct ctg cgc atg ctg ggg atg cat                  720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ntt                  768
Gly Thr Val Tyr Ala Asn Tyr Ala Val Asp Lys Ala Asp Leu Leu Ile
                245                 250                 255 gca ttt ggt gtg cgg ttt gat gat cgt gtg acc ggg aaa atc gag gct                  816
Ala Phe Gly Val Arg Phe Asp Asp Arg Val Thr Gly Lys Ile Glu Ala
            260                 265                 270 ttt gca agc agg tcc aag att gtg cac att gac att gac cca gct gag                  864
Phe Ala Ser Arg Ser Lys Ile Val His Ile Asp Ile Asp Pro Ala Glu
        275                 280                 285 att ggc aag aac aag cag cca cat gtc tcc att tgt gca gat gtt aag                  912
Ile Gly Lys Asn Lys Gln Pro His Val Ser Ile Cys Ala Asp Val Lys
        290                 295                 300 ctt gct tta cag ggg ttg aat gct cta tta aat ggg agc aaa gca caa                  960
Leu Ala Leu Gln Gly Leu Asn Ala Leu Leu Asn Gly Ser Lys Ala Gln
305                 310                 315                 320 cag ggt ctg gat ttt ggt cca tgg cac aag gag ttg gat cag cag aag                 1008
Gln Gly Leu Asp Phe Gly Pro Trp His Lys Glu Leu Asp Gln Gln Lys
                325                 330                 335 agg gag ttt cct cta gga ttc aag act ttt ggt gag gcc atc ccg ccg                 1056
Arg Glu Phe Pro Leu Gly Phe Lys Thr Phe Gly Glu Ala Ile Pro Pro
            340                 345                 350 caa tat gct atc cag gta ctg gat gag ctg aca aaa ggg gag gcg atc                 1104
Gln Tyr Ala Ile Gln Val Leu Asp Glu Leu Thr Lys Gly Glu Ala Ile
        355                 360                 365 att gcc acc ggt gtt ggg cag cat cag atg tgg gcg gct cag tat tac                 1152
Ile Ala Thr Gly Val Gly Gln His Gln Met Trp Ala Ala Gln Tyr Tyr
    370                 375                 380 act tac aag cgg cca cgg cag tgg ctg tct tca tcc ggt ttg ggt gca                 1200
Thr Tyr Lys Arg Pro Arg Gln Trp Leu Ser Ser Ser Gly Leu Gly Ala
385                 390                 395                 400 atg gga ttt ggg ttg cca gct gca gct ggc gct gct gtg gcc aac cca                 1248
Met Gly Phe Gly Leu Pro Ala Ala Ala Gly Ala Ala Val Ala Asn Pro
                405                 410                 415 ggt gtt aca gtt gtt gac att gat ggg gat ggt agt ttc ctc atg aac                 1296
Gly Val Thr Val Val Asp Ile Asp Gly Asp Gly Ser Phe Leu Met Asn
            420                 425                 430 att cag gag ttg gcg ttg atc cgt att gag aac ctc cca gtg aag gtg                 1344
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat                 1392
Met Ile Leu Asn Asn Gln His Leu Gly Met Val Val Gln Trp Glu Asp
    450                 455                 460 agg ttt tac aag gcc aac cgg gcg cac aca tac ctt ggc aac cca gaa                 1440
```

```
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc    1488
Asn Glu Ser Glu Ile Tyr Pro Asp Phe Val Thr Ile Ala Lys Gly Phe
                485                 490                 495 aac gtt ccg gca gtt cgt gtg acg aag aag agc gaa gtc act gca gca    1536
Asn Val Pro Ala Val Arg Val Thr Lys Lys Ser Glu Val Thr Ala Ala
        500                 505                 510 atc aag aag atg ctt gag acc cca ggg cca tac ttg ttg gat atc att    1584
Ile Lys Lys Met Leu Glu Thr Pro Gly Pro Tyr Leu Leu Asp Ile Ile
    515                 520                 525 gtc ccg cat cag gag cac gtg ctg cct atg atc cca agc ggt ggt gct    1632
Val Pro His Gln Glu His Val Leu Pro Met Ile Pro Ser Gly Gly Ala
530                 535                 540 ttt aag gac atg atc atg gag ggt gat ggc agg acc tcg tac             1674
Phe Lys Asp Met Ile Met Glu Gly Asp Gly Arg Thr Ser Tyr
545                 550                 555

<210> SEQ ID NO 26
<211> LENGTH: 557
<212> TYPE: PRT
<213> ORGANISM: Triticum aestivum

<400> SEQUENCE: 26

Val Asp Val Phe Ala Tyr Pro Gly Gly Ala Ser Met Glu Ile His Gln
1               5                   10                  15

Ala Leu Thr Arg Ser Pro Val Ile Thr Asn His Leu Phe Arg His Glu
            20                  25                  30

Gln Gly Glu Ala Phe Ala Ala Ser Gly Tyr Ala Arg Ala Ser Gly Arg
        35                  40                  45

Val Gly Val Cys Val Ala Thr Ser Gly Pro Gly Ala Thr Asn Leu Val
    50                  55                  60

Ser Ala Leu Ala Asp Ala Leu Leu Asp Ser Ile Pro Met Val Ala Ile
65                  70                  75                  80

Thr Gly Gln Val Pro Arg Arg Met Ile Gly Thr Asp Ala Phe Gln Glu
                85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
            180                 185                 190

Tyr Val Gly Gly Gly Cys Ala Ala Ser Gly Glu Glu Leu Arg Arg Phe
        195                 200                 205

Val Glu Leu Thr Gly Ile Pro Val Thr Thr Thr Leu Met Gly Leu Gly
    210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Ile
                245                 250                 255

Ala Phe Gly Val Arg Phe Asp Asp Arg Val Thr Gly Lys Ile Glu Ala
```

-continued

```
                    260                 265                 270
Phe Ala Ser Arg Ser Lys Ile Val His Ile Asp Ile Asp Pro Ala Glu
                275                 280                 285
Ile Gly Lys Asn Lys Gln Pro His Val Ser Ile Cys Ala Asp Val Lys
            290                 295                 300
Leu Ala Leu Gln Gly Leu Asn Ala Leu Leu Asn Gly Ser Lys Ala Gln
305                 310                 315                 320
Gln Gly Leu Asp Phe Gly Pro Trp His Lys Glu Leu Asp Gln Gln Lys
                325                 330                 335
Arg Glu Phe Pro Leu Gly Phe Lys Thr Phe Gly Glu Ala Ile Pro Pro
            340                 345                 350
Gln Tyr Ala Ile Gln Val Leu Asp Glu Leu Thr Lys Gly Glu Ala Ile
        355                 360                 365
Ile Ala Thr Gly Val Gly Gln His Gln Met Trp Ala Ala Gln Tyr Tyr
    370                 375                 380
Thr Tyr Lys Arg Pro Arg Gln Trp Leu Ser Ser Gly Leu Gly Ala
385                 390                 395                 400
Met Gly Phe Gly Leu Pro Ala Ala Ala Gly Ala Ala Val Ala Asn Pro
                405                 410                 415
Gly Val Thr Val Val Asp Ile Asp Gly Asp Gly Ser Phe Leu Met Asn
            420                 425                 430
Ile Gln Glu Leu Ala Leu Ile Arg Ile Glu Asn Leu Pro Val Lys Val
        435                 440                 445
Met Ile Leu Asn Asn Gln His Leu Gly Met Val Val Gln Trp Glu Asp
    450                 455                 460
Arg Phe Tyr Lys Ala Asn Arg Ala His Thr Tyr Leu Gly Asn Pro Glu
465                 470                 475                 480
Asn Glu Ser Glu Ile Tyr Pro Asp Phe Val Thr Ile Ala Lys Gly Phe
                485                 490                 495
Asn Val Pro Ala Val Arg Val Thr Lys Lys Ser Glu Val Thr Ala Ala
            500                 505                 510
Ile Lys Lys Met Leu Glu Thr Pro Gly Pro Tyr Leu Leu Asp Ile Ile
        515                 520                 525
Val Pro His Gln Glu His Val Leu Pro Met Ile Pro Ser Gly Gly Ala
    530                 535                 540
Phe Lys Asp Met Ile Met Glu Gly Asp Gly Arg Thr Ser
545                 550                 555
```

```
<210> SEQ ID NO 27
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (644)
<223> OTHER INFORMATION: unknown nucleotide

<400> SEQUENCE: 27
```

```
gtc gac gtc ttc gcc tac cct ggc ggc gcg tcc atg gag atc cac cag      48
Val Asp Val Phe Ala Tyr Pro Gly Gly Ala Ser Met Glu Ile His Gln
  1               5                  10                  15 gcg ctg acg cgc tcg cca gtc atc acc aac cac ctc ttc cgc cac gag      96
Ala Leu Thr Arg Ser Pro Val Ile Thr Asn His Leu Phe Arg His Glu
             20                  25                  30 cag ggg gag gcg ttc gcg gcg tcc ggg tac gcc cgc gcg tcc ggc cgc     144
```

|     |     |     |     |     |     |     |     |     |     |     |     |     |
| --- | --- | --- | --- | --- | --- | --- | --- | --- | --- | --- | --- | --- |
|     | Gln | Gly | Glu | Ala | Phe | Ala | Ala | Ser | Gly | Tyr | Ala | Arg | Ala | Ser | Gly | Arg |
|     |     | 35  |     |     |     | 40  |     |     |     |     | 45  |     |

```
gtc ggc gtc tgc gtc gcc acc tcc ggc ccg ggg gcc acc aac ctc gtc      192
Val Gly Val Cys Val Ala Thr Ser Gly Pro Gly Ala Thr Asn Leu Val
     50                  55                  60 tcc gcg ctc gcc gac gct ctc ctc gac tcc atc ccc atg gtc gcc atc      240
Ser Ala Leu Ala Asp Ala Leu Leu Asp Ser Ile Pro Met Val Ala Ile
 65                  70                  75                  80 acg ggc cag gtc ccc cgc cgc atg atc ggc acg gat gcg ttc cag gag      288
Thr Gly Gln Val Pro Arg Arg Met Ile Gly Thr Asp Ala Phe Gln Glu
                 85                  90                  95 acg ccc atc gtg gag gtc acg cgc tcc atc acc aag cac aac tac ctg      336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc      384
Val Leu Asp Val Glu Asp Ile Pro Arg Val Ile Gln Glu Ala Phe Phe
        115                 120                 125 ctc gca tcc tct ggc cgc ccg ggg ccg gtg ctg gtt gat atc ccc aag      432
Leu Ala Ser Ser Gly Arg Pro Gly Pro Val Leu Val Asp Ile Pro Lys
    130                 135                 140 gac atc cag cag cag atg gct gtg cct gtc tgg gac acg ccg atg agt      480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg      528
Leu Pro Gly Tyr Ile Ala Arg Leu Pro Lys Pro Pro Ser Thr Glu Ser
                    165                 170                 175 ctt gag cag gtc ctg cgt ctg gtt ggc gag tca cgg cgc cca att ctg      576
Leu Glu Gln Val Leu Arg Leu Val Gly Glu Ser Arg Arg Pro Ile Leu
                180                 185                 190 tat gtt ggt ggt ggc tgc gct gca tct ggt gag gag ttg cgc cgc ttt      624
Tyr Val Gly Gly Gly Cys Ala Ala Ser Gly Glu Glu Leu Arg Arg Phe
            195                 200                 205 gtt gag ctc act ggg att cna gtt aca act act ctt atg ggc ctt ggc      672
Val Glu Leu Thr Gly Ile Xaa Val Thr Thr Thr Leu Met Gly Leu Gly
        210                 215                 220 aac ttc ccc agt gac gac cca ctg tct ctg cgc atg ctg ggg atg cat      720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ctt      768
Gly Thr Val Tyr Ala Asn Tyr Ala Val Asp Lys Ala Asp Leu Leu Leu
                    245                 250                 255 gca ttt ggt gtg cgg ttt gat gat cgt gtg acc ggg aaa atc gag gct      816
Ala Phe Gly Val Arg Phe Asp Asp Arg Val Thr Gly Lys Ile Glu Ala
                260                 265                 270 ttt gca agc agg tcc aag att gtg cac att gac att gac cca gct gag      864
Phe Ala Ser Arg Ser Lys Ile Val His Ile Asp Ile Asp Pro Ala Glu
            275                 280                 285 att ggc aag aac aag cag cca cat gtc tcc att tgt gca gat gtt aag      912
Ile Gly Lys Asn Lys Gln Pro His Val Ser Ile Cys Ala Asp Val Lys
        290                 295                 300 ctt gct tta cag ggg ttg aat gct cta tta aat ggg agc aaa gca caa      960
Leu Ala Leu Gln Gly Leu Asn Ala Leu Leu Asn Gly Ser Lys Ala Gln
305                 310                 315                 320 cag ggt ctg gat ttt ggt cca tgg cac aag gag ttg gat cag cag aag     1008
Gln Gly Leu Asp Phe Gly Pro Trp His Lys Glu Leu Asp Gln Gln Lys
                    325                 330                 335 agg gag ttt cct cta gga ttc aag act ttt ggt gag gcc atc ccg ccg     1056
Arg Glu Phe Pro Leu Gly Phe Lys Thr Phe Gly Glu Ala Ile Pro Pro
                340                 345                 350 caa tat gct atc cag gta ctg gat gag ctg aca aaa ggg gag gcg atc     1104
```

```
                                                                        1152
att gcc acc ggt gtt ggg cag cat cag atg tgg gcg gct cag tat tac
Ile Ala Thr Gly Val Gly Gln His Gln Met Trp Ala Ala Gln Tyr Tyr
370             375                 380

1200
act tac aag cgg cca cgg cag tgg ctg tct tca tcc ggt ttg ggt gca
Thr Tyr Lys Arg Pro Arg Gln Trp Leu Ser Ser Ser Gly Leu Gly Ala
385             390                 395                 400

1248
atg gga ttt ggg ttg cca gct gca ggc gct gct gtg gcc aac cca
Met Gly Phe Gly Leu Pro Ala Ala Gly Ala Ala Val Ala Asn Pro
                405                 410                 415

1296
ggt gtt aca gtt gtt gac att gat ggg gat ggt agt ttc ctc atg aac
Gly Val Thr Val Val Asp Ile Asp Gly Asp Gly Ser Phe Leu Met Asn
                420                 425                 430

1344
att cag gag ttg gcg ttg atc cgt att gag aac ctc cca gtg aag gtg
Ile Gln Glu Leu Ala Leu Ile Arg Ile Glu Asn Leu Pro Val Lys Val
                435                 440                 445

1392
atg ata ttg aac aac cag cat ctg gga atg gtg gtg cag tgg gag gat
Met Ile Leu Asn Asn Gln His Leu Gly Met Val Val Gln Trp Glu Asp
450                 455                 460

1440
agg ttt tac aag gcc aac cgg gcg cac aca tac ctt ggc aac cca gaa
Arg Phe Tyr Lys Ala Asn Arg Ala His Thr Tyr Leu Gly Asn Pro Glu
465                 470                 475                 480

1488
aat gag agt gag ata tat cca gat ttt gtg acg att gct aaa gga ttc
Asn Glu Ser Glu Ile Tyr Pro Asp Phe Val Thr Ile Ala Lys Gly Phe
                485                 490                 495

1536
aac gtt ccg gca gtt cgt gtg acg aag aag agc gaa gtc act gca gca
Asn Val Pro Ala Val Arg Val Thr Lys Lys Ser Glu Val Thr Ala Ala
                500                 505                 510

1584
atc aag aag atg ctt gag acc cca ggg cca tac ttg ttg gat atc att
Ile Lys Lys Met Leu Glu Thr Pro Gly Pro Tyr Leu Leu Asp Ile Ile
                515                 520                 525

1632
gtc ccg cat cag gag cac gtg ctg cct atg atc cca agc ggt ggt gct
Val Pro His Gln Glu His Val Leu Pro Met Ile Pro Ser Gly Gly Ala
                530                 535                 540

1674
ttt aag gac atg atc atg gag ggt gat ggc agg acc tcg tac
Phe Lys Asp Met Ile Met Glu Gly Asp Gly Arg Thr Ser
545                 550                 555

<210> SEQ ID NO 28
<211> LENGTH: 557
<212> TYPE: PRT
<213> ORGANISM: Triticum aestivum
<220> FEATURE:
<221> NAME/KEY: MOD_RES
<222> LOCATION: (215)
<223> OTHER INFORMATION: unknown amino acid

<400> SEQUENCE: 28

Val Asp Val Phe Ala Tyr Pro Gly Gly Ala Ser Met Glu Ile His Gln
1               5                   10                  15

Ala Leu Thr Arg Ser Pro Val Ile Thr Asn His Leu Phe Arg His Glu
                20                  25                  30

Gln Gly Glu Ala Phe Ala Ala Ser Gly Tyr Ala Arg Ala Ser Gly Arg
            35                  40                  45

Val Gly Val Cys Val Ala Thr Ser Gly Pro Gly Ala Thr Asn Leu Val
        50                  55                  60

Ser Ala Leu Ala Asp Ala Leu Leu Asp Ser Ile Pro Met Val Ala Ile
65                  70                  75                  80

Thr Gly Gln Val Pro Arg Arg Met Ile Gly Thr Asp Ala Phe Gln Glu
                85                  90                  95
```

```
Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
            115                 120                 125

Leu Ala Ser Ser Gly Arg Pro Gly Pro Val Leu Val Asp Ile Pro Lys
        130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
            180                 185                 190

Tyr Val Gly Gly Gly Cys Ala Ala Ser Gly Glu Glu Leu Arg Arg Phe
            195                 200                 205

Val Glu Leu Thr Gly Ile Xaa Val Thr Thr Thr Leu Met Gly Leu Gly
        210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Leu
                245                 250                 255

Ala Phe Gly Val Arg Phe Asp Asp Arg Val Thr Gly Lys Ile Glu Ala
            260                 265                 270

Phe Ala Ser Arg Ser Lys Ile Val His Ile Asp Ile Asp Pro Ala Glu
        275                 280                 285

Ile Gly Lys Asn Lys Gln Pro His Val Ser Ile Cys Ala Asp Val Lys
        290                 295                 300

Leu Ala Leu Gln Gly Leu Asn Ala Leu Leu Asn Gly Ser Lys Ala Gln
305                 310                 315                 320

Gln Gly Leu Asp Phe Gly Pro Trp His Lys Glu Leu Asp Gln Gln Lys
                325                 330                 335

Arg Glu Phe Pro Leu Gly Phe Lys Thr Phe Gly Glu Ala Ile Pro Pro
            340                 345                 350

Gln Tyr Ala Ile Gln Val Leu Asp Glu Leu Thr Lys Gly Glu Ala Ile
        355                 360                 365

Ile Ala Thr Gly Val Gly Gln His Gln Met Trp Ala Ala Gln Tyr Tyr
        370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Gly Ala Ala Val Ala Asn Pro
                405                 410                 415

Gly Val Thr Val Val Asp Ile Asp Gly Asp Gly Ser Phe Leu Met Asn
            420                 425                 430

Ile Gln Glu Leu Ala Leu Ile Arg Ile Glu Asn Leu Pro Val Lys Val
        435                 440                 445

Met Ile Leu Asn Asn Gln His Leu Gly Met Val Val Gln Trp Glu Asp
        450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
                485                 490                 495

Asn Val Pro Ala Val Arg Val Thr Lys Lys Ser Glu Val Thr Ala Ala
            500                 505                 510

Ile Lys Lys Met Leu Glu Thr Pro Gly Pro Tyr Leu Leu Asp Ile Ile
```

```
                515                 520                 525
Val Pro His Gln Glu His Val Leu Pro Met Ile Pro Ser Gly Gly Ala
    530                 535                 540

Phe Lys Asp Met Ile Met Glu Gly Asp Gly Arg Thr Ser
545                 550                 555

<210> SEQ ID NO 29
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (782)
<223> OTHER INFORMATION: unknown nucleotide
<220> FEATURE:
<221> NAME/KEY: modified_base
<222> LOCATION: (800)
<223> OTHER INFORMATION: unknown nucleotide
<220> FEATURE:
<221> NAME/KEY: modified_base
<222> LOCATION: (813)
<223> OTHER INFORMATION: unknown nucleotide
<220> FEATURE:
<221> NAME/KEY: modified_base
<222> LOCATION: (839)
<223> OTHER INFORMATION: unknown nucleotide
<220> FEATURE:
<221> NAME/KEY: modified_base
<222> LOCATION: (887)
<223> OTHER INFORMATION: unknown nucleotide
<220> FEATURE:
<221> NAME/KEY: modified_base
<222> LOCATION: (912)
<223> OTHER INFORMATION: unknown nucleotide
<220> FEATURE:
<221> NAME/KEY: modified_base
<222> LOCATION: (936)
<223> OTHER INFORMATION: unknown nucleotide
<220> FEATURE:
<221> NAME/KEY: modified_base
<222> LOCATION: (966)
<223> OTHER INFORMATION: unknown nucleotide
<220> FEATURE:
<221> NAME/KEY: modified_base
<222> LOCATION: (986)
<223> OTHER INFORMATION: unknown nucleotide
<220> FEATURE:
<221> NAME/KEY: modified_base
<222> LOCATION: (1010)
<223> OTHER INFORMATION: unknown nucleotide
<220> FEATURE:
<221> NAME/KEY: modified_base
<222> LOCATION: (1032)
<223> OTHER INFORMATION: unknown nucleotide
<220> FEATURE:
<221> NAME/KEY: modified_base
<222> LOCATION: (1042)
<223> OTHER INFORMATION: unknown nucleotide
<220> FEATURE:
<221> NAME/KEY: modified_base
<222> LOCATION: (1045)
<223> OTHER INFORMATION: unknown nucleotide
<220> FEATURE:
<221> NAME/KEY: modified_base
<222> LOCATION: (1116)
<223> OTHER INFORMATION: unknown nucleotide
<220> FEATURE:
<221> NAME/KEY: modified_base
<222> LOCATION: (1131)
<223> OTHER INFORMATION: unknown nucleotide
<220> FEATURE:
<221> NAME/KEY: modified_base
<222> LOCATION: (1167)
<223> OTHER INFORMATION: unknown nucleotide
```

<220> FEATURE:
<221> NAME/KEY: modified_base
<222> LOCATION: (1236)
<223> OTHER INFORMATION: unknown nucleotide

<400> SEQUENCE: 29

| | | | | | | | | | | | | | | | | |
|---|---|---|---|---|---|---|---|---|---|---|---|---|---|---|---|---|
| gtc | gac | gtc | ttc | gcc | tac | cct | ggc | ggc | gcg | tcc | atg | gag | atc | cac | cag | 48 |
| Val | Asp | Val | Phe | Ala | Tyr | Pro | Gly | Gly | Ala | Ser | Met | Glu | Ile | His | Gln | |
| 1 | | | | 5 | | | | | 10 | | | | | 15 | | |
| gcg | ctg | acg | cgc | tcg | cca | gtc | atc | acc | aac | cac | ctc | ttc | cgc | cac | gag | 96 |
| Ala | Leu | Thr | Arg | Ser | Pro | Val | Ile | Thr | Asn | His | Leu | Phe | Arg | His | Glu | |
| | | | 20 | | | | | 25 | | | | | 30 | | | |
| cag | ggg | gag | gcg | ttc | gcg | gcg | tcc | ggg | tac | gcc | cgc | gcg | tcc | ggc | cgc | 144 |
| Gln | Gly | Glu | Ala | Phe | Ala | Ala | Ser | Gly | Tyr | Ala | Arg | Ala | Ser | Gly | Arg | |
| | 35 | | | | | 40 | | | | | 45 | | | | | |
| gtc | ggc | gtc | tgc | gtc | gcc | acc | tcc | ggc | ccg | ggg | gcc | acc | aac | ctc | gtc | 192 |
| Val | Gly | Val | Cys | Val | Ala | Thr | Ser | Gly | Pro | Gly | Ala | Thr | Asn | Leu | Val | |
| 50 | | | | | 55 | | | | | 60 | | | | | | |
| tcc | gcg | ctc | gcc | gac | gct | ctc | ctc | gac | tcc | atc | ccc | atg | gtc | gcc | atc | 240 |
| Ser | Ala | Leu | Ala | Asp | Ala | Leu | Leu | Asp | Ser | Ile | Pro | Met | Val | Ala | Ile | |
| 65 | | | | | 70 | | | | | 75 | | | | | 80 | |
| acg | ggc | cag | gtc | ccc | cgc | cgc | atg | atc | ggc | acg | gat | gcg | ttc | cag | gag | 288 |
| Thr | Gly | Gln | Val | Pro | Arg | Arg | Met | Ile | Gly | Thr | Asp | Ala | Phe | Gln | Glu | |
| | | | | 85 | | | | | 90 | | | | | 95 | | |
| acg | ccc | atc | gtg | gag | gtc | acg | cgc | tcc | atc | acc | aag | cac | aac | tac | ctg | 336 |
| Thr | Pro | Ile | Val | Glu | Val | Thr | Arg | Ser | Ile | Thr | Lys | His | Asn | Tyr | Leu | |
| | | | 100 | | | | | 105 | | | | | 110 | | | |
| gtc | ctt | gac | gtg | gag | gat | atc | ccc | cgc | gtc | atc | cag | gaa | gcc | ttc | ttc | 384 |
| Val | Leu | Asp | Val | Glu | Asp | Ile | Pro | Arg | Val | Ile | Gln | Glu | Ala | Phe | Phe | |
| | | 115 | | | | | 120 | | | | | 125 | | | | |
| ctc | gca | tcc | tct | ggc | cgc | ccg | ggg | ccg | gtg | ctg | gtt | gat | atc | ccc | aag | 432 |
| Leu | Ala | Ser | Ser | Gly | Arg | Pro | Gly | Pro | Val | Leu | Val | Asp | Ile | Pro | Lys | |
| | 130 | | | | | 135 | | | | | 140 | | | | | |
| gac | atc | cag | cag | cag | atg | gct | gtg | cct | gtc | tgg | gac | acg | ccg | atg | agt | 480 |
| Asp | Ile | Gln | Gln | Gln | Met | Ala | Val | Pro | Val | Trp | Asp | Thr | Pro | Met | Ser | |
| 145 | | | | | 150 | | | | | 155 | | | | | 160 | |
| ttg | cca | ggg | tac | atc | gcc | cgc | ctg | ccc | aag | cca | cca | tct | act | gaa | tcg | 528 |
| Leu | Pro | Gly | Tyr | Ile | Ala | Arg | Leu | Pro | Lys | Pro | Pro | Ser | Thr | Glu | Ser | |
| | | | | 165 | | | | | 170 | | | | | 175 | | |
| ctt | gag | cag | gtc | ctg | cgt | ctg | gtt | ggc | gag | tca | cgg | cgc | cca | att | ctg | 576 |
| Leu | Glu | Gln | Val | Leu | Arg | Leu | Val | Gly | Glu | Ser | Arg | Arg | Pro | Ile | Leu | |
| | | | 180 | | | | | 185 | | | | | 190 | | | |
| tat | gtt | ggt | ggt | ggc | tgc | gct | gca | tct | ggt | gag | gag | ttg | cgc | cgc | ttt | 624 |
| Tyr | Val | Gly | Gly | Gly | Cys | Ala | Ala | Ser | Gly | Glu | Glu | Leu | Arg | Arg | Phe | |
| | | 195 | | | | | 200 | | | | | 205 | | | | |
| gtt | gag | ctc | act | ggg | att | cca | gtt | aca | act | act | ctt | atg | ggc | ctt | ggc | 672 |
| Val | Glu | Leu | Thr | Gly | Ile | Pro | Val | Thr | Thr | Thr | Leu | Met | Gly | Leu | Gly | |
| | 210 | | | | | 215 | | | | | 220 | | | | | |
| aac | ttc | ccc | agt | gac | gac | cca | ctg | tct | ctg | cgc | atg | ctg | ggg | atg | cat | 720 |
| Asn | Phe | Pro | Ser | Asp | Asp | Pro | Leu | Ser | Leu | Arg | Met | Leu | Gly | Met | His | |
| 225 | | | | | 230 | | | | | 235 | | | | | 240 | |
| ggc | act | gtg | tat | gca | aat | tat | gca | gta | gat | aag | gct | gac | ctg | ttg | ctt | 768 |
| Gly | Thr | Val | Tyr | Ala | Asn | Tyr | Ala | Val | Asp | Lys | Ala | Asp | Leu | Leu | Leu | |
| | | | | 245 | | | | | 250 | | | | | 255 | | |
| gca | ttt | ggt | gtg | cng | gtt | gat | gat | cgt | gtg | anc | ggg | aaa | atc | gan | gct | 816 |
| Ala | Phe | Gly | Val | Gln | Val | Asp | Asp | Arg | Val | Asn | Gly | Lys | Ile | Glu | Ala | |
| | | | 260 | | | | | 265 | | | | | 270 | | | |
| ttt | gca | agc | agg | tcc | aag | att | gng | cac | att | gac | att | gac | cca | gct | gag | 864 |
| Phe | Ala | Ser | Arg | Ser | Lys | Ile | Glu | His | Ile | Asp | Ile | Asp | Pro | Ala | Glu | |
| | 275 | | | | | 280 | | | | | 285 | | | | | |
| att | ggc | aag | aac | aag | cag | cca | cnt | gtc | tcc | att | tgt | gca | gat | gtt | aan | 912 |

```
Ile Gly Lys Asn Lys Gln Pro His Val Ser Ile Cys Ala Asp Val Xaa
290                 295                 300 ctt gct tta cag ggg ttg aat gcn cta tta aat ggg agc aaa gca caa       960
Leu Ala Leu Gln Gly Leu Asn Ala Leu Leu Asn Gly Ser Lys Ala Gln
305                 310                 315                 320 cag ggn ctg gat ttt ggt cca tgg cnc aag gag ttg gat cag caa aag      1008
Gln Gly Leu Asp Phe Gly Pro Trp His Lys Glu Leu Asp Gln Gln Lys
                325                 330                 335 ang gag ttt cct cta gga ttc aan act ttt ggn gan gcc atc ccg ccg      1056
Lys Glu Phe Pro Leu Gly Phe Lys Thr Phe Gly Glu Ala Ile Pro Pro
            340                 345                 350 cca tat gct atc cag gta ctg gat gag ctg aca aaa ggg gag gcg atc      1104
Pro Tyr Ala Ile Gln Val Leu Asp Glu Leu Thr Lys Gly Glu Ala Ile
        355                 360                 365 att gcc acc ggn gtt ggg cag cat can atg tgg gcg gct cag tat tac      1152
Ile Ala Thr Xaa Val Gly Gln His Thr Met Trp Ala Ala Gln Tyr Tyr
370                 375                 380 act tac aag cgg ccn cgg cag tgg ctg tct tca tcc ggt ttg ggt gca      1200
Thr Tyr Lys Arg Pro Arg Gln Trp Leu Ser Ser Ser Gly Leu Gly Ala
385                 390                 395                 400 atg gga ttt ggg ttg cca gct gca gct ggc ggc nct gtg gcc aac cca      1248
Met Gly Phe Gly Leu Pro Ala Ala Ala Gly Gly Xaa Val Ala Asn Pro
                405                 410                 415 ggt gtt aca gtt gtt gac att gat ggg gat ggt agt ttc ctc atg aac      1296
Gly Val Thr Val Val Asp Ile Asp Gly Asp Gly Ser Phe Leu Met Asn
            420                 425                 430 att cag gag ttg gcg ttg atc cgt att gag aac ctc cca gtg aag gtg      1344
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat      1392
Met Ile Leu Asn Asn Gln His Leu Gly Met Val Val Gln Trp Glu Asp
450                 455                 460 agg ttt tac aag gcc aac cgg gcg cac aca tac ctt ggc aac cca gaa      1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc      1488
Asn Glu Ser Glu Ile Tyr Pro Asp Phe Val Thr Ile Ala Lys Gly Phe
                485                 490                 495 aac gtt ccg gca gtt cgt gtg acg aag aag agc gaa gtc act gca gca      1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc att      1584
Ile Lys Lys Met Leu Glu Thr Pro Gly Pro Tyr Leu Leu Asp Ile Ile
        515                 520                 525 gtc ccg cat cag gag cac gtg ctg cct atg atc cca agc ggt ggt gct      1632
Val Pro His Gln Glu His Val Leu Pro Met Ile Pro Ser Gly Gly Ala
530                 535                 540 ttt aag gac atg atc atg gag ggt gat ggc agg acc tcg tac              1674
Phe Lys Asp Met Ile Met Glu Gly Asp Gly Arg Thr Ser
545                 550                 555

<210> SEQ ID NO 30
<211> LENGTH: 557
<212> TYPE: PRT
<213> ORGANISM: Triticum aestivum
<220> FEATURE:
<221> NAME/KEY: MOD_RES
<222> LOCATION: (412)
<223> OTHER INFORMATION: unknown amino acid

<400> SEQUENCE: 30

Val Asp Val Phe Ala Tyr Pro Gly Gly Ala Ser Met Glu Ile His Gln
```

```
             1               5              10              15
Ala Leu Thr Arg Ser Pro Val Ile Thr Asn His Leu Phe Arg His Glu
                 20                  25                  30

Gln Gly Glu Ala Phe Ala Ala Ser Gly Tyr Ala Arg Ala Ser Gly Arg
                 35                  40                  45

Val Gly Val Cys Val Ala Thr Ser Gly Pro Gly Ala Thr Asn Leu Val
                 50                  55                  60

Ser Ala Leu Ala Asp Ala Leu Leu Asp Ser Ile Pro Met Val Ala Ile
 65                  70                  75                  80

Thr Gly Gln Val Pro Arg Arg Met Ile Gly Thr Asp Ala Phe Gln Glu
                 85                  90                  95

Thr Pro Ile Val Glu Val Thr Arg Ser Ile Thr Lys His Asn Tyr Leu
                100                 105                 110

Val Leu Asp Val Glu Asp Ile Pro Arg Val Ile Gln Glu Ala Phe Phe
                115                 120                 125

Leu Ala Ser Ser Gly Arg Pro Gly Pro Val Leu Val Asp Ile Pro Lys
                130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
                180                 185                 190

Tyr Val Gly Gly Gly Cys Ala Ala Ser Gly Glu Glu Leu Arg Arg Phe
                195                 200                 205

Val Glu Leu Thr Gly Ile Pro Val Thr Thr Thr Leu Met Gly Leu Gly
                210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Leu
                245                 250                 255

Ala Phe Gly Val Gln Val Asp Asp Arg Val Asn Gly Lys Ile Glu Ala
                260                 265                 270

Phe Ala Ser Arg Ser Lys Ile Glu His Ile Asp Ile Asp Pro Ala Glu
                275                 280                 285

Ile Gly Lys Asn Lys Gln Pro His Val Ser Ile Cys Ala Asp Val Lys
                290                 295                 300

Leu Ala Leu Gln Gly Leu Asn Ala Leu Leu Asn Gly Ser Lys Ala Gln
305                 310                 315                 320

Gln Gly Leu Asp Phe Gly Pro Trp His Lys Glu Leu Asp Gln Gln Lys
                325                 330                 335

Lys Glu Phe Pro Leu Gly Phe Lys Thr Phe Gly Glu Ala Ile Pro Pro
                340                 345                 350

Pro Tyr Ala Ile Gln Val Leu Asp Glu Leu Thr Lys Gly Glu Ala Ile
                355                 360                 365

Ile Ala Thr Xaa Val Gly Gln His Thr Met Trp Ala Ala Gln Tyr Tyr
370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Ala Gly Xaa Val Ala Asn Pro
                405                 410                 415

Gly Val Thr Val Val Asp Ile Asp Gly Asp Gly Ser Phe Leu Met Asn
                420                 425                 430
```

```
Ile Gln Glu Leu Ala Leu Ile Arg Ile Glu Asn Leu Pro Val Lys Val
        435                 440                 445

Met Ile Leu Asn Asn Gln His Leu Gly Met Val Val Gln Trp Glu Asp
    450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
                485                 490                 495

Asn Val Pro Ala Val Arg Val Thr Lys Lys Ser Glu Val Thr Ala Ala
                500                 505                 510

Ile Lys Lys Met Leu Glu Thr Pro Gly Pro Tyr Leu Leu Asp Ile Ile
            515                 520                 525

Val Pro His Gln Glu His Val Leu Pro Met Ile Pro Ser Gly Gly Ala
        530                 535                 540

Phe Lys Asp Met Ile Met Glu Gly Asp Gly Arg Thr Ser
545                 550                 555
```

```
<210> SEQ ID NO 31
<211> LENGTH: 1674
<212> TYPE: DNA
<213> ORGANISM: Triticum aestivum
<220> FEATURE:
<221> NAME/KEY: CDS
<222> LOCATION: (1)..(1671)

<400> SEQUENCE: 31
```

```
gtc gac gtc ttc gcc tac cct ggc ggc gcg tcc atg gag atc cac cag      48
Val Asp Val Phe Ala Tyr Pro Gly Gly Ala Ser Met Glu Ile His Gln
 1               5                  10                  15 gcg ctg acg cgc tcg cca gtc atc acc aac cac ctc ttc cgc cac gag      96
Ala Leu Thr Arg Ser Pro Val Ile Thr Asn His Leu Phe Arg His Glu
             20                  25                  30 cag ggg gag gcg ttc gcg gcg tcc ggg tac gcc cgc gcg tcc ggc cgc     144
Gln Gly Glu Ala Phe Ala Ala Ser Gly Tyr Ala Arg Ala Ser Gly Arg
         35                  40                  45 gtc ggc gtc tgc gtc gcc acc tcc ggc ccg ggg gcc acc aac ctc gtc     192
Val Gly Val Cys Val Ala Thr Ser Gly Pro Gly Ala Thr Asn Leu Val
     50                  55                  60 tcc gcg ctc gcc gac gct ctc ctc gac tcc atc ccc atg gtc gcc atc     240
Ser Ala Leu Ala Asp Ala Leu Leu Asp Ser Ile Pro Met Val Ala Ile
 65                  70                  75                  80 acg ggc cag gtc ccc cgc cgc atg atc ggc acg gat gcg ttc cag gag     288
Thr Gly Gln Val Pro Arg Arg Met Ile Gly Thr Asp Ala Phe Gln Glu
                 85                  90                  95 acg ccc atc gtg gag gtc acg cgc tcc atc acc aag cac aac tac ctg     336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc     384
Val Leu Asp Val Glu Asp Ile Pro Arg Val Ile Gln Glu Ala Phe Phe
        115                 120                 125 ctc gca tcc tct ggc cgc ccg ggg ccg gtg ctg gtt gat atc ccc aag     432
Leu Ala Ser Ser Gly Arg Pro Gly Pro Val Leu Val Asp Ile Pro Lys
    130                 135                 140 gac atc cag cag cag atg gct gtg cct gtc tgg gac acg ccg atg agt     480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg     528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg     576
```

```
                Leu Glu Gln Val Leu Arg Leu Val Gly Glu Ser Arg Arg Pro Ile Leu
                                180                 185                 190 tat gtt ggt ggt ggc tgc gct gca tct ggt gag gag ttg cgc cgc ttt       624
Tyr Val Gly Gly Gly Cys Ala Ala Ser Gly Glu Glu Leu Arg Arg Phe
            195                 200                 205 gtt gag ctc act ggg att cca gtt aca act act ctt atg ggc ctt ggc       672
Val Glu Leu Thr Gly Ile Pro Val Thr Thr Thr Leu Met Gly Leu Gly
            210                 215                 220 aac ttc ccc agt gac gac cca ctg tct ctg cgc atg ctg ggg atg cat       720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ctt       768
Gly Thr Val Tyr Ala Asn Tyr Ala Val Asp Lys Ala Asp Leu Leu Leu
                245                 250                 255 gca ttt ggt gtg cgg ttt gat gat cgt gtg acc ggg aaa atc gag gct       816
Ala Phe Gly Val Arg Phe Asp Asp Arg Val Thr Gly Lys Ile Glu Ala
                260                 265                 270 ttt gca agc agg tcc aag att gtg cac att gac att gac cca gct gag       864
Phe Ala Ser Arg Ser Lys Ile Val His Ile Asp Ile Asp Pro Ala Glu
            275                 280                 285 att ggc aag aac aag cag cca cat gtc tcc att tgt gca gat gtt aag       912
Ile Gly Lys Asn Lys Gln Pro His Val Ser Ile Cys Ala Asp Val Lys
            290                 295                 300 ctt gct tta cag ggg ttg aat gct cta tta aat ggg agc aaa gca caa       960
Leu Ala Leu Gln Gly Leu Asn Ala Leu Leu Asn Gly Ser Lys Ala Gln
305                 310                 315                 320 cag ggt ctg gat ttt ggt cca tgg cac aag gag ttg gat cag cag aag      1008
Gln Gly Leu Asp Phe Gly Pro Trp His Lys Glu Leu Asp Gln Gln Lys
                325                 330                 335 agg gag ttt cct cta gga ttc aag act ttt ggt gag gcc atc ccg ccg      1056
Arg Glu Phe Pro Leu Gly Phe Lys Thr Phe Gly Glu Ala Ile Pro Pro
                340                 345                 350 caa tat gct atc cag gta ctg gat gag ctg aca aaa ggg gag gcg atc      1104
Gln Tyr Ala Ile Gln Val Leu Asp Glu Leu Thr Lys Gly Glu Ala Ile
            355                 360                 365 att gcc acc ggt gtt ggg cag cat cag atg tgg gcg gct cag tat tac      1152
Ile Ala Thr Gly Val Gly Gln His Gln Met Trp Ala Ala Gln Tyr Tyr
370                 375                 380 act tac aag cgg cca cgg cag tgg ctg tct tca tcc ggt ttg ggt gca      1200
Thr Tyr Lys Arg Pro Arg Gln Trp Leu Ser Ser Ser Gly Leu Gly Ala
385                 390                 395                 400 atg gga ttt ggg ttg cca gct gca gct ggc gct gct gtg gcc aac cca      1248
Met Gly Phe Gly Leu Pro Ala Ala Ala Gly Ala Ala Val Ala Asn Pro
                405                 410                 415 ggt gtt aca gtt gtt gac att gat ggg gat ggt agt ttc ctc atg aac      1296
Gly Val Thr Val Val Asp Ile Asp Gly Asp Gly Ser Phe Leu Met Asn
            420                 425                 430 att cag gag ttg gcg ttg atc cgt att gag aac ctc cca gtg aag gtg      1344
Ile Gln Glu Leu Ala Leu Ile Arg Ile Glu Asn Leu Pro Val Lys Val
            435                 440                 445 atg ata ttg aac aac cag cat ctg gga atg gtg gtg cag tgg gag gat      1392
Met Ile Leu Asn Asn Gln His Leu Gly Met Val Val Gln Trp Glu Asp
450                 455                 460 agg ttt tac aag gcc aac cgg gcg cac aca tac ctt ggc aac cca gaa      1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc      1488
Asn Glu Ser Glu Ile Tyr Pro Asp Phe Val Thr Ile Ala Lys Gly Phe
                485                 490                 495 aac gtt ccg gca gtt cgt gtg acg aag aag agc gaa gtc act gca gca      1536
```

```
Asn Val Pro Ala Val Arg Val Thr Lys Lys Ser Glu Val Thr Ala Ala
            500                 505                 510 atc aag aag atg ctt gag acc cca ggg cca tac ttg ttg gat atc att    1584
Ile Lys Lys Met Leu Glu Thr Pro Gly Pro Tyr Leu Leu Asp Ile Ile
            515                 520                 525 gtc ccg cat cag gag cac gtg ctg cct atg atc cca aac ggt ggt gct    1632
Val Pro His Gln Glu His Val Leu Pro Met Ile Pro Asn Gly Gly Ala
            530                 535                 540 ttt aag gac atg atc atg gag ggt gat ggc agg acc tcg tac            1674
Phe Lys Asp Met Ile Met Glu Gly Asp Gly Arg Thr Ser
545                 550                 555

<210> SEQ ID NO 32
<211> LENGTH: 557
<212> TYPE: PRT
<213> ORGANISM: Triticum aestivum

<400> SEQUENCE: 32

Val Asp Val Phe Ala Tyr Pro Gly Gly Ala Ser Met Glu Ile His Gln
  1               5                  10                  15

Ala Leu Thr Arg Ser Pro Val Ile Thr Asn His Leu Phe Arg His Glu
             20                  25                  30

Gln Gly Glu Ala Phe Ala Ala Ser Gly Tyr Ala Arg Ala Ser Gly Arg
         35                  40                  45

Val Gly Val Cys Val Ala Thr Ser Gly Pro Gly Ala Thr Asn Leu Val
     50                  55                  60

Ser Ala Leu Ala Asp Ala Leu Leu Asp Ser Ile Pro Met Val Ala Ile
 65                  70                  75                  80

Thr Gly Gln Val Pro Arg Arg Met Ile Gly Thr Asp Ala Phe Gln Glu
                 85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
            180                 185                 190

Tyr Val Gly Gly Gly Cys Ala Ala Ser Gly Glu Glu Leu Arg Arg Phe
        195                 200                 205

Val Glu Leu Thr Gly Ile Pro Val Thr Thr Thr Leu Met Gly Leu Gly
    210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Leu
                245                 250                 255

Ala Phe Gly Val Arg Phe Asp Asp Arg Val Thr Gly Lys Ile Glu Ala
            260                 265                 270

Phe Ala Ser Arg Ser Lys Ile Val His Ile Asp Ile Asp Pro Ala Glu
        275                 280                 285

Ile Gly Lys Asn Lys Gln Pro His Val Ser Ile Cys Ala Asp Val Lys
    290                 295                 300
```

```
Leu Ala Leu Gln Gly Leu Asn Ala Leu Leu Asn Gly Ser Lys Ala Gln
305                 310                 315                 320

Gln Gly Leu Asp Phe Gly Pro Trp His Lys Glu Leu Asp Gln Gln Lys
                325                 330                 335

Arg Glu Phe Pro Leu Gly Phe Lys Thr Phe Gly Glu Ala Ile Pro Pro
            340                 345                 350

Gln Tyr Ala Ile Gln Val Leu Asp Glu Leu Thr Lys Gly Glu Ala Ile
        355                 360                 365

Ile Ala Thr Gly Val Gly Gln His Gln Met Trp Ala Ala Gln Tyr Tyr
370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Ala Gly Ala Ala Val Ala Asn Pro
                405                 410                 415

Gly Val Thr Val Val Asp Ile Asp Gly Asp Gly Ser Phe Leu Met Asn
            420                 425                 430

Ile Gln Glu Leu Ala Leu Ile Arg Ile Glu Asn Leu Pro Val Lys Val
        435                 440                 445

Met Ile Leu Asn Asn Gln His Leu Gly Met Val Val Gln Trp Glu Asp
450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
                485                 490                 495

Asn Val Pro Ala Val Arg Val Thr Lys Lys Ser Glu Val Thr Ala Ala
            500                 505                 510

Ile Lys Lys Met Leu Glu Thr Pro Gly Pro Tyr Leu Leu Asp Ile Ile
        515                 520                 525

Val Pro His Gln Glu His Val Leu Pro Met Ile Pro Asn Gly Gly Ala
530                 535                 540

Phe Lys Asp Met Ile Met Glu Gly Asp Gly Arg Thr Ser
545                 550                 555
```

<210> SEQ ID NO 33
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (723)
<223> OTHER INFORMATION: unknown nucleotide
<220> FEATURE:
<221> NAME/KEY: modified_base
<222> LOCATION: (1089)
<223> OTHER INFORMATION: unknown nucleotide

<400> SEQUENCE: 33

```
gtc gac gtc ttc gcc tac cct ggc ggc gcg tcc atg gag atc cac cag      48
Val Asp Val Phe Ala Tyr Pro Gly Gly Ala Ser Met Glu Ile His Gln
1               5                   10                  15 gcg ctg acg cgc tcg cca gtc atc acc aac cac ctc ttc cgc cac gag      96
Ala Leu Thr Arg Ser Pro Val Ile Thr Asn His Leu Phe Arg His Glu
            20                  25                  30 cag ggg gag gcg ttc gcg gcg tcc ggg tac gcc cgc gcg tcc ggc cgc     144
Gln Gly Glu Ala Phe Ala Ala Ser Gly Tyr Ala Arg Ala Ser Gly Arg
        35                  40                  45 gtc ggc gtc tgc gtc gcc acc tcc ggc ccg ggg gcc acc aac ctc gtc     192
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Val | Gly | Val | Cys | Val | Ala | Thr | Ser | Gly | Pro | Gly | Ala | Thr | Asn | Leu | Val | |
| | 50 | | | | 55 | | | | | 60 | | | | | | |

```
tcc gcg ctc gcc gac gct ctc ctc gac tcc atc ccc atg gtc gcc atc      240
Ser Ala Leu Ala Asp Ala Leu Leu Asp Ser Ile Pro Met Val Ala Ile
 65              70                  75                  80 acg ggc cag gtc ccc cgc cgc atg atc ggc acg gat gcg ttc cag gag      288
Thr Gly Gln Val Pro Arg Arg Met Ile Gly Thr Asp Ala Phe Gln Glu
                 85                  90                  95 acg ccc atc gtg gag gtc acg cgc tcc atc acc aag cac aac tac ctg      336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc      384
Val Leu Asp Val Glu Asp Ile Pro Arg Val Ile Gln Glu Ala Phe Phe
        115                 120                 125 ctc gca tcc tct ggc cgc ccg ggg ccg gtg ctg gtt gat atc ccc aag      432
Leu Ala Ser Ser Gly Arg Pro Gly Pro Val Leu Val Asp Ile Pro Lys
    130                 135                 140 gac atc cag cag cag atg gct gtg cct gtc tgg gac acg ccg atg agt      480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg      528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg      576
Leu Glu Gln Val Leu Arg Leu Val Gly Glu Ser Arg Arg Pro Ile Leu
            180                 185                 190 tat gtt ggt ggt ggc tgc gct gca tct ggt gag gag ttg cgc cgc ttt      624
Tyr Val Gly Gly Gly Cys Ala Ala Ser Gly Glu Glu Leu Arg Arg Phe
        195                 200                 205 gtt gag ctc act ggg att cca gtt aca act act ctt atg ggc ctt ggc      672
Val Glu Leu Thr Gly Ile Pro Val Thr Thr Thr Leu Met Gly Leu Gly
    210                 215                 220 aac ttc ccc agt gac gac cca ctg tct ctg cgc atg ctg ggg atg cat      720
Asn Phe Pro Ser Asp Asp Pro Leu Ser Leu Arg Met Leu Gly Met His
225                 230                 235                 240 ggn act gtg tat gca aat tat gca gta gat aag gct gac ctg ttg ctt      768
Gly Thr Val Tyr Ala Asn Tyr Ala Val Asp Lys Ala Asp Leu Leu Leu
                245                 250                 255 gca ttt ggt gtg cgg ttt gat gat cgt gtg acc ggg aaa atc gag gct      816
Ala Phe Gly Val Arg Phe Asp Asp Arg Val Thr Gly Lys Ile Glu Ala
            260                 265                 270 ttt gca agc agg tcc aag att gtg cac att gac att gac cca gct gag      864
Phe Ala Ser Arg Ser Lys Ile Val His Ile Asp Ile Asp Pro Ala Glu
        275                 280                 285 att ggc aag aac aag cag cca cat gtc tcc att tgt gca gat gtt aag      912
Ile Gly Lys Asn Lys Gln Pro His Val Ser Ile Cys Ala Asp Val Lys
    290                 295                 300 ctt gct tta cag ggg ttg aat gct cta tta aat ggg agc aaa gca caa      960
Leu Ala Leu Gln Gly Leu Asn Ala Leu Leu Asn Gly Ser Lys Ala Gln
305                 310                 315                 320 cag ggt ctg gat ttt ggt cca tgg cac aag gag ttg gat cag cag aag     1008
Gln Gly Leu Asp Phe Gly Pro Trp His Lys Glu Leu Asp Gln Gln Lys
                325                 330                 335 agg gag ttt cct cta gga ttc aag act ttt ggt gag gcc atc ccg ccg     1056
Arg Glu Phe Pro Leu Gly Phe Lys Thr Phe Gly Glu Ala Ile Pro Pro
            340                 345                 350 caa tat gct atc cag gta ctg gat gag ctg acn aaa ggg gag gcg atc     1104
Gln Tyr Ala Ile Gln Val Leu Asp Glu Leu Thr Lys Gly Glu Ala Ile
        355                 360                 365 att gcc acc ggt gtt ggg cag cat cag atg tgg gcg gct cag tat tac     1152
```

```
Ile Ala Thr Gly Val Gly Gln His Gln Met Trp Ala Ala Gln Tyr Tyr
            370                 375                 380 act tac aag cgg cca cgg cag tgg ctg tct tca tcc ggt ttg ggt gca      1200
Thr Tyr Lys Arg Pro Arg Gln Trp Leu Ser Ser Ser Gly Leu Gly Ala
385                 390                 395                 400 atg gga ttt ggg ttg cca gct gca gct ggc gct gct gtg gcc aac cca      1248
Met Gly Phe Gly Leu Pro Ala Ala Ala Gly Ala Ala Val Ala Asn Pro
            405                 410                 415 ggt gtt aca gtt gtt gac att gat ggg gat ggt agt ttc ctc atg aac      1296
Gly Val Thr Val Val Asp Ile Asp Gly Asp Gly Ser Phe Leu Met Asn
            420                 425                 430 att cag gag ttg gcg ttg atc cgt att gag aac ctc cca gtg aag gtg      1344
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat      1392
Met Ile Leu Asn Asn Gln His Leu Gly Met Val Val Gln Trp Glu Asp
    450                 455                 460 agg ttt tac aag gcc aac cgg gcg cac aca tac ctt ggc aac cca gaa      1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc      1488
Asn Glu Ser Glu Ile Tyr Pro Asp Phe Val Thr Ile Ala Lys Gly Phe
            485                 490                 495 aac gtt ccg gca gtt cgt gtg acg aag aag agc gaa gtc act gca gca      1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc att      1584
Ile Lys Lys Met Leu Glu Thr Pro Gly Pro Tyr Leu Leu Asp Ile Ile
        515                 520                 525 gtc ccg cat cag gag cac gtg ctg cct atg atc cca agc ggt ggt gct      1632
Val Pro His Gln Glu His Val Leu Pro Met Ile Pro Ser Gly Gly Ala
    530                 535                 540 ttt aag gac atg atc atg gag ggt gat ggc agg acc tcg tac              1674
Phe Lys Asp Met Ile Met Glu Gly Asp Gly Arg Thr Ser
545                 550                 555

<210> SEQ ID NO 34
<211> LENGTH: 557
<212> TYPE: PRT
<213> ORGANISM: Triticum aestivum

<400> SEQUENCE: 34

Val Asp Val Phe Ala Tyr Pro Gly Gly Ala Ser Met Glu Ile His Gln
1               5                   10                  15

Ala Leu Thr Arg Ser Pro Val Ile Thr Asn His Leu Phe Arg His Glu
            20                  25                  30

Gln Gly Glu Ala Phe Ala Ala Ser Gly Tyr Ala Arg Ala Ser Gly Arg
        35                  40                  45

Val Gly Val Cys Val Ala Thr Ser Gly Pro Gly Ala Thr Asn Leu Val
    50                  55                  60

Ser Ala Leu Ala Asp Ala Leu Leu Asp Ser Ile Pro Met Val Ala Ile
65                  70                  75                  80

Thr Gly Gln Val Pro Arg Arg Met Ile Gly Thr Asp Ala Phe Gln Glu
                85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
```

```
              130                 135                 140
Asp Ile Gln Gln Gln Met Ala Val Pro Val Trp Asp Thr Pro Met Ser
145                 150                 155                 160
Leu Pro Gly Tyr Ile Ala Arg Leu Pro Lys Pro Pro Ser Thr Glu Ser
                    165                 170                 175
Leu Glu Gln Val Leu Arg Leu Val Gly Glu Ser Arg Arg Pro Ile Leu
                180                 185                 190
Tyr Val Gly Gly Gly Cys Ala Ala Ser Gly Glu Glu Leu Arg Arg Phe
                195                 200                 205
Val Glu Leu Thr Gly Ile Pro Val Thr Thr Thr Leu Met Gly Leu Gly
210                 215                 220
Asn Phe Pro Ser Asp Asp Pro Leu Ser Leu Arg Met Leu Gly Met His
225                 230                 235                 240
Gly Thr Val Tyr Ala Asn Tyr Ala Val Asp Lys Ala Asp Leu Leu Leu
                    245                 250                 255
Ala Phe Gly Val Arg Phe Asp Asp Arg Val Thr Gly Lys Ile Glu Ala
                260                 265                 270
Phe Ala Ser Arg Ser Lys Ile Val His Ile Asp Ile Asp Pro Ala Glu
                275                 280                 285
Ile Gly Lys Asn Lys Gln Pro His Val Ser Ile Cys Ala Asp Val Lys
290                 295                 300
Leu Ala Leu Gln Gly Leu Asn Ala Leu Leu Asn Gly Ser Lys Ala Gln
305                 310                 315                 320
Gln Gly Leu Asp Phe Gly Pro Trp His Lys Glu Leu Asp Gln Gln Lys
                    325                 330                 335
Arg Glu Phe Pro Leu Gly Phe Lys Thr Phe Gly Glu Ala Ile Pro Pro
                340                 345                 350
Gln Tyr Ala Ile Gln Val Leu Asp Glu Leu Thr Lys Gly Glu Ala Ile
                355                 360                 365
Ile Ala Thr Gly Val Gly Gln His Gln Met Trp Ala Ala Gln Tyr Tyr
                370                 375                 380
Thr Tyr Lys Arg Pro Arg Gln Trp Leu Ser Ser Gly Leu Gly Ala
385                 390                 395                 400
Met Gly Phe Gly Leu Pro Ala Ala Gly Ala Val Ala Asn Pro
                    405                 410                 415
Gly Val Thr Val Val Asp Ile Asp Gly Asp Gly Ser Phe Leu Met Asn
                420                 425                 430
Ile Gln Glu Leu Ala Leu Ile Arg Ile Glu Asn Leu Pro Val Lys Val
                435                 440                 445
Met Ile Leu Asn Asn Gln His Leu Gly Met Val Val Gln Trp Glu Asp
450                 455                 460
Arg Phe Tyr Lys Ala Asn Arg Ala His Thr Tyr Leu Gly Asn Pro Glu
465                 470                 475                 480
Asn Glu Ser Glu Ile Tyr Pro Asp Phe Val Thr Ile Ala Lys Gly Phe
                    485                 490                 495
Asn Val Pro Ala Val Arg Val Thr Lys Lys Ser Glu Val Thr Ala Ala
                500                 505                 510
Ile Lys Lys Met Leu Glu Thr Pro Gly Pro Tyr Leu Leu Asp Ile Ile
                515                 520                 525
Val Pro His Gln Glu His Val Leu Pro Met Ile Pro Ser Gly Gly Ala
                530                 535                 540
Phe Lys Asp Met Ile Met Glu Gly Asp Gly Arg Thr Ser
545                 550                 555
```

<210> SEQ ID NO 35
<211> LENGTH: 1524
<212> TYPE: DNA
<213> ORGANISM: Artificial Sequence
<220> FEATURE:
<223> OTHER INFORMATION: Description of Artificial Sequence: Consensus
      sequence
<220> FEATURE:
<221> NAME/KEY: modified_base
<222> LOCATION: (1125)
<223> OTHER INFORMATION: a, t, c or g

<400> SEQUENCE: 35

```
gtctgcgtcg ccacctccgg cccgggggcc accaacctcg tctccgcgct cgccgacgcc      60
ctcctcgact ccatccccat ggtcgccatc acgggccagg tcccccgccg catgatcggc     120
acggacgcgt tccaggagac gcccatagtg gaggtcacgc gctccatcac caagcacaac     180
tacctggtcc ttgacgtgga ggatatcccc cgcgtcatcc aggaagcctt cttcctcgca     240
tcctctggcc gcccggggcc ggtgctggtt gatatcccca aggacatcca gcagcagatg     300
gctgtgcctg tctgggacac gccgatgagt ttgccagggt acatcgcccg cctgcccaag     360
ccaccatcta ctgaatcgct tgagcaggtc ctgcgtctgg ttggcgagtc acggcgccca     420
attctgtatg ttggtggtgg ctgcgctgca tctggcgagg agttgcgccg ctttgttgag     480
ctcactggga ttccagttac aactactctg atgggccttg caacttccc cagcgacgac       540 ccactgtctc tgcgcatgct tgggatgcat ggcactgtgt atgcaaatta tgcagtagat     600
aaggctgacc tgttgcttgc atttggtgtg cggtttgatg atcgtgtgac tgggaaaatc     660
gaggcttttg caagcaggtc caagattgtg cacattgaca ttgacccagc tgagattggc     720
aagaacaagc agccacatgt ctccatttgt gcagatgtta agcttgcttt acaggggttg     780
aatgctctat taaatgggag caaagcacaa cagggtctgg attttggtcc atggcacaag     840
gagttggatc agcagaagag ggagtttcct ctaggattca agacttttgg cgaggccatc     900
ccgccgcaat atgctatcca ggtactggat gagctgacaa aggggaggc gatcattgcc      960 actggtgttg gcagcacca gatgtgggcg gctcagtatt acacttacaa gcggccacgg    1020
cagtggctgt cttcgtctgg tttgggggca atgggatttg ggttaccagc tgcagctggc    1080
gctgctgtgg ccaacccagg tgttacagtt gttgacattg atggngatgg tagtttcctc    1140
atgaacattc aggagttggc gttgatccgt attgagaacc tcccagtgaa ggtgatgata    1200
ttgaacaacc agcatctggg aatggtggtg cagtgggagg ataggtttta caaggccaat    1260
cgggcgcaca catacottgg caacccagaa aatgagagtg agatatatcc agattttgtg    1320
acgattgcta aaggattcaa cgttccggca gttcgtgtga cgaagaagag cgaagtcact    1380
gcagcaatca agaagatgct tgagaccccca gggccatact tgttggatat catngtcccg    1440
catcaggagc acgtgctgcc tatgatccca agcggtggtg ctttcaagga catgatcatg    1500
gagggtgatg gcaggacctc gtac                                           1524
```